(12) United States Patent
Khvorova et al.

(10) Patent No.: US 10,799,591 B2
(45) Date of Patent: Oct. 13, 2020

(54) BRANCHED OLIGONUCLEOTIDES

(71) Applicant: UNIVERSITY OF MASSACHUSETTS, Boston, MA (US)

(72) Inventors: Anastasia Khvorova, Westborough, MA (US); Matthew Hassler, Worcester, MA (US); Julia Alterman, Worcester, MA (US); Bruno Miguel da Cruz Godinho, Worcester, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 16/390,712

(22) Filed: Apr. 22, 2019

(65) Prior Publication Data
US 2019/0247507 A1    Aug. 15, 2019

Related U.S. Application Data

(62) Division of application No. 15/419,593, filed on Jan. 30, 2017, now Pat. No. 10,478,503.

(60) Provisional application No. 62/317,113, filed on Apr. 1, 2016, provisional application No. 62/289,268, filed on Jan. 31, 2016.

(51) Int. Cl.
| | |
|---|---|
| *A61K 47/26* | (2006.01) |
| *C12N 15/113* | (2010.01) |
| *C12N 15/11* | (2006.01) |
| *A61K 47/54* | (2017.01) |
| *A61K 47/55* | (2017.01) |
| *A61K 31/7084* | (2006.01) |
| *C07H 3/08* | (2006.01) |
| *C07H 21/04* | (2006.01) |
| *C07H 99/00* | (2006.01) |

(52) U.S. Cl.
CPC .......... *A61K 47/26* (2013.01); *A61K 31/7084* (2013.01); *A61K 47/549* (2017.08); *A61K 47/55* (2017.08); *A61K 47/551* (2017.08); *C07H 3/08* (2013.01); *C07H 21/04* (2013.01); *C07H 99/00* (2013.01); *C12N 15/111* (2013.01); *C12N 15/113* (2013.01); *C12N 2310/11* (2013.01); *C12N 2310/14* (2013.01); *C12N 2310/3513* (2013.01); *C12N 2310/3515* (2013.01); *C12N 2310/52* (2013.01)

(58) Field of Classification Search
CPC .............. A61K 9/0019; C12N 2310/14; C12N 2310/52; C12N 2310/321; C12N 2310/322; C12N 2310/315; C12N 2310/3525; C12N 2310/3515; C12N 15/111; C12N 15/113
USPC ........... 435/6.1, 6.11, 91.1, 91.31, 455, 458; 514/1, 2, 44; 536/23.1, 24.5
See application file for complete search history.

(56) References Cited

U.S. PATENT DOCUMENTS

| | | |
|---|---|---|
| 4,522,811 A | 6/1985 | Eppstein et al. |
| 5,328,470 A | 7/1994 | Nabel et al. |
| 5,684,143 A | 11/1997 | Gryaznov et al. |
| 5,814,014 A | 9/1998 | Elsberry et al. |
| 5,858,988 A | 1/1999 | Wang |
| 6,093,180 A | 7/2000 | Elsberry |
| 6,107,094 A | 8/2000 | Crooke |
| 6,168,587 B1 | 1/2001 | Bellhouse et al. |
| 6,177,403 B1 | 1/2001 | Stedman |
| 6,194,389 B1 | 2/2001 | Johnston et al. |
| 6,291,438 B1 | 9/2001 | Wang |
| 6,471,996 B1 | 10/2002 | Sokoll et al. |
| 6,472,375 B1 | 10/2002 | Hoon et al. |
| 6,489,464 B1 * | 12/2002 | Agrawal ................ C07H 21/00 536/24.5 |
| 7,250,496 B2 | 7/2007 | Bentwich |
| 7,459,547 B2 | 12/2008 | Zamore et al. |
| 7,732,593 B2 | 6/2010 | Zamore et al. |
| 7,750,144 B2 | 7/2010 | Zamore et al. |
| 7,772,203 B2 | 8/2010 | Zamore et al. |
| 8,304,530 B2 | 11/2012 | Zamore et al. |
| 8,309,704 B2 | 11/2012 | Zamore et al. |
| 8,309,705 B2 | 11/2012 | Zamore et al. |
| 8,329,892 B2 | 12/2012 | Zamore et al. |
| 8,431,544 B1 | 4/2013 | Agrawal et al. |
| 8,664,189 B2 | 3/2014 | Khvorova et al. |
| 8,703,731 B2 | 4/2014 | Jimenes Ana Isabel et al. |
| 8,796,443 B2 | 8/2014 | Khvorova et al. |
| 8,815,818 B2 | 8/2014 | Samarsky et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,303,259 B2 | 4/2016 | Khvorova et al. |
| 9,340,786 B2 | 5/2016 | Khvorova et al. |
| 9,493,774 B2 | 11/2016 | Kamens et al. |
| 9,809,817 B2 | 11/2017 | Khvorova et al. |
| 2003/0143732 A1 | 7/2003 | Fosnaugh et al. |
| 2004/0198640 A1 | 10/2004 | Leake et al. |
| 2005/0096284 A1 | 5/2005 | McSwiggen et al. |
| 2005/0220766 A1 | 10/2005 | Amalfitano et al. |

(Continued)

FOREIGN PATENT DOCUMENTS

| | | |
|---|---|---|
| CN | 101199858 A | 6/2008 |
| EP | 2407539 A1 | 1/2012 |

(Continued)

OTHER PUBLICATIONS

Avino et al (J. Nucleic Acids, vol. 2011, Article IC586935. (Year: 2011).*

(Continued)

*Primary Examiner* — Jane J Zara
(74) *Attorney, Agent, or Firm* — Lathrop GPM LLP; James H. Velema, Esq.; Michael J. Spellberg

(57) ABSTRACT

Provided herein are branched oligonucleotides exhibiting efficient and specific tissue distribution, cellular uptake, minimum immune response and off-target effects, without formulation.

16 Claims, 52 Drawing Sheets
Specification includes a Sequence Listing.

(56) References Cited

U.S. PATENT DOCUMENTS

| | | |
|---|---|---|
| 2006/0009409 A1 | 1/2006 | Woolf |
| 2006/0078542 A1 | 4/2006 | Mah et al. |
| 2006/0094032 A1 | 5/2006 | Fougerolles et al. |
| 2007/0004664 A1* | 1/2007 | McSwiggen .......... C12N 15/111 514/44 A |
| 2007/0099860 A1 | 5/2007 | Sah et al. |
| 2007/0135372 A1 | 6/2007 | MacLachlan et al. |
| 2007/0191273 A1 | 8/2007 | Ambati et al. |
| 2007/0259827 A1 | 11/2007 | Aronin et al. |
| 2008/0039415 A1 | 2/2008 | Stewart et al. |
| 2008/0119427 A1 | 5/2008 | Brat et al. |
| 2008/0269149 A1 | 10/2008 | Bowles et al. |
| 2009/0143322 A1 | 6/2009 | Burkoth et al. |
| 2010/0186103 A1 | 7/2010 | Gao et al. |
| 2011/0039914 A1 | 2/2011 | Pavco et al. |
| 2011/0237522 A1 | 9/2011 | Khvorova et al. |
| 2011/0237648 A1 | 9/2011 | Khvorova et al. |
| 2011/0251258 A1 | 10/2011 | Samarsky et al. |
| 2011/0263680 A1 | 10/2011 | Khvorova et al. |
| 2012/0016005 A1 | 1/2012 | Samarsky et al. |
| 2012/0040459 A1 | 2/2012 | Khvorova et al. |
| 2012/0059046 A1 | 3/2012 | Woolf et al. |
| 2012/0065243 A1 | 3/2012 | Woolf et al. |
| 2013/0131141 A1 | 5/2013 | Khvorova et al. |
| 2013/0131142 A1 | 5/2013 | Libertine et al. |
| 2013/0197055 A1 | 8/2013 | Kamens et al. |
| 2014/0113950 A1 | 4/2014 | Khvorova et al. |
| 2014/0296486 A1 | 10/2014 | Gao et al. |
| 2014/0315974 A1 | 10/2014 | Khvorova et al. |
| 2014/0364482 A1 | 12/2014 | Khvorova et al. |
| 2016/0017323 A1* | 1/2016 | Prakash ............. A61K 31/7088 536/24.5 |
| 2016/0115482 A1 | 4/2016 | Libertine et al. |
| 2016/0130578 A1 | 5/2016 | Khvorova et al. |
| 2016/0244765 A1 | 8/2016 | Khvorova et al. |
| 2016/0319278 A1 | 11/2016 | Khvorova et al. |
| 2016/0355808 A1 | 12/2016 | Khvorova et al. |
| 2016/0355826 A1 | 12/2016 | Khvorova et al. |
| 2017/0009239 A1 | 1/2017 | Khvorova et al. |
| 2017/0037456 A1* | 2/2017 | Kokoris ............... C12Q 1/6825 |
| 2017/0043024 A1 | 2/2017 | Khvorova et al. |
| 2017/0067056 A1 | 3/2017 | Khvorova et al. |

FOREIGN PATENT DOCUMENTS

| | | |
|---|---|---|
| WO | 2003/029459 A2 | 4/2003 |
| WO | 2004/008946 A2 | 1/2004 |
| WO | 2004/044136 A2 | 5/2004 |
| WO | 2006/019430 A2 | 2/2006 |
| WO | 2007/051045 A2 | 5/2007 |
| WO | 2007091269 A2 | 8/2007 |
| WO | 2008/154482 A2 | 12/2008 |
| WO | 2009/099991 A2 | 8/2009 |
| WO | 2009102427 A2 | 8/2009 |
| WO | 2010008582 A2 | 1/2010 |
| WO | 2010011346 A1 | 1/2010 |
| WO | 2010/033247 A2 | 3/2010 |
| WO | 2010033246 A1 | 3/2010 |
| WO | 2010033248 A2 | 3/2010 |
| WO | 2010059226 A2 | 5/2010 |
| WO | 2010078536 A1 | 7/2010 |
| WO | 2010090762 A1 | 8/2010 |
| WO | 2011109698 A1 | 9/2011 |
| WO | 2011119852 A1 | 9/2011 |
| WO | 2011119871 A1 | 9/2011 |
| WO | 2011119887 A1 | 9/2011 |
| WO | 2012/005898 A2 | 1/2012 |
| WO | 2012/118911 A1 | 9/2012 |
| WO | 2013/165816 A2 | 11/2013 |
| WO | 2014/076195 A1 | 5/2014 |
| WO | 2015/161184 A1 | 10/2015 |
| WO | 2015161184 A1 | 10/2015 |
| WO | 2016161374 A1 | 10/2016 |
| WO | 2016205410 A2 | 12/2016 |

OTHER PUBLICATIONS

Lagos-Quintana et al. (2001) "Identification of novel genes coding for small expressed RNAs," Science. 294(5543):853-858.

Lai et al. (2003) "Computational identification of Drosophila microRNA genes," Genome Biol. 4(7):R42. pp. 1-20.

Lau et al. (2001) "An abundant class of tiny RNAs with probable regulatory roles in Caenorhabditis elegans," Science. 294(5543):858-862.

Lau et al. (2006) "Characterization of the piRNA complex from rat testes," Science. 313(5785):363-367.

Lee et al. (2001) "An extensive class of small RNAs in Caenorhabditis elegans," Science. 294(5543):862-864.

Lee et al. (2002) "Expression of small interfering RNAs targeted against HIV-1 rev transcripts in human cells," Nat. Biotechnol. 20:500-505.

Lim et al. (2003) "The microRNAs of Caenorhabditis elegans," Genes Dev. 17(8):991-1008.

Lim et al. (2003) "Vertebrate microRNA genes," Science. 299(5612):1540.

Lima et al. (Aug. 31, 2012) "Single-stranded siRNAs activate RNAi in animals," Cell. 150:883-894.

Lorenz et al. (2004) "Steroid and lipid conjugates of siRNAs to enhance cellular uptake and gene silencing in liver cells," Bioorg. Med. Chem. Lett. 14:4975-4977.

Luo et al. (Jun. 18, 2013) "Photoreceptor avascular privilege is shielded by soluble VEGF receptor-1," eLife. 6: e19456. pp. 1-22.

McCaffrey et al. (2002) "RNA interference in adult mice," Nature. 418(6893):38-39.

McManus et al. (2002) "Gene silencing using micro-RNA designed hairpins," RNA. 8:842-850.

Miyagishi et al. (2002) "U6 promoter-driven siRNAs with four uridine 3' overhangs efficiently suppress targeted gene expression in mammalian cells," Nat. Biotechnol. 20:497-500.

Molitoris et al. (2009) "siRNA Targeted to p53 Attenuates Ischemic and Cisplatin-Induced Acute Kidney Injury," Journal of the American Society of Nephrology. 20:1754-1764.

Myers et al. (1988) "Optimal alignments in linear space," Comput. Appl. Biosci. 4(1):11-17.

Nair et al. (Dec. 10, 2014) "Multivalent N-Acetylgalactosamine-Conjugated siRNA Localizes in Hepatocytes and Elicits Robust RNAi-Mediated Gene Silencing," J. Am. Chem. Soc. 136(49):16958-16961.

Nielsen et al. (2001) "Sequence-selective recognition of DNA by strand displacement with a thymine-substituted polyamide," Science. 254:1497-1500.

Nikan et al. (Aug. 9, 2016) "Docosahexaenoic Acid Conjugation Enhances Distribution and Safety of siRNA upon Local Administration in Mouse Brain," Mol. Ther. Nucleic Acids. 5(8):e344. pp. 1-11.

Owen et al. (Mar. 15, 2012) "Morpholino-mediated increase in soluble Flt-1 expression results in decreased ocular and tumor neovascularization," PloS One. 7(3):e33576. pp. 1-9.

Paddison et al. (2002) "Short hairpin RNAs (shRNAs) induce sequence-specific silencing in mammalian cells," Gene Dev. 16:948-958.

Pasquinelli et al. (2000) "Conservation of the sequence and temporal expression of let-7 heterochronic regulatory RNA," Nature. 408(6808):86-89.

Paul et al. (2002) "Effective expression of small interfering RNA in human cells," Nature Biotechnol. 20:505-508.

Peel et al. (Feb. 12, 2015) "Conjugation and Evaluation of Small Hydrophobic Molecules to Triazole-Linked siRNAs," ACS Med. Chem. Lett. 6(2)117-122.

Petersen et al. (2003) "LNA: a versatile tool for therapeutics and genomics," Trends Biotechnol 21:74-81.

Putnam (1996) "Antisense strategies and therapeutic applications," Am. J. Health Syst. Pharm. 53(2):151-160.

Reinhart et al. (2002) "Small RNAs correspond to centromere heterochromatic repeats," Science. 297(5588):1831.

Rigo et al. (Apr. 20, 2014) "Pharmacology of a central nervous system delivered 2'-O-methoxyethyl-modified survival of motor neuron splicing oligonucleotide in mice and nonhuman primates," The Journal of Pharmacology and Experimental Therapeutics. 350:46-55.

(56) References Cited

OTHER PUBLICATIONS

Rodriguez-Lebron et al. (2005) "Intrastriatal rAAV-mediated delivery of anti-huntingtin shRNAs induces partial reversal of disease progression in R6/1 Huntington's disease transgenic mice," Mol. Ther. 12(4):618-633.
Rusckowski et al. (2000) "Biodistribution and metabolism of a mixed backbone oligonucleotide (GEM 231) following single and multiple dose administration in mice," Antisense Nucleic Acid Drug Dev. 10(5):333-345.
Schirle et al. (Oct. 31, 2014) "Gene Regulation. Structural basis for microRNA targeting," Science. 346:608-613.
Schwab et al. (1994) "An approach for new anticancer drugs: oncogene-targeted antisense DNA," Ann. Oncol. 5 (Suppl 4):55-58.
Schwarz et al. (2003) Asymmetry in the Assembly of the RNAi Enzyme Complex. Cell 115:199-208.
Song et al. (2003) "Sustained Small Interfering RNA-Mediated Human Immunodeficiency Virus Type 1 Inhibition in Primary Macrophages," Journal of Virology. 77:7174-7181.
Soutschek et al. (2004) "Therapeutic silencing of an endogenous gene by systemic administration of modified siRNAs," Nature. 432:173-178.
Stalder et al. (Mar. 19, 2013) "The rough endoplasmatic reticulum is a central nucleation site of siRNA-mediated RNA silencing," EMBO J. 32:1115-1127.
Stein (2001) "Inhibition of Vesivirus infections in mammalian tissue culture with antisense morpholino oligomers," Antisense Nucleic Acid Drug Dev. 11(5):317-25.
Stokman et al. (2010) "Application of siRNA in targeting protein expression in kidney disease," Advanced Drug Delivery Reviews. 62:1378-1389.
Sui et al. (2002) "A DNA vector-based RNAi technology to suppress gene expression in mammalian cells," Proc Natl Acad Sci USA. 99:5515-5520.
Tabernero et al. (Apr. 2013) "First-in-humans trial of an RNA interference therapeutic targeting VEGF and KSP in cancer patients with liver involvement," Cancer Discovery. 3:406-417.
Thomas et al. (2009) "A recently evolved novel trophoblast-enriched secreted form of fms-like tyrosine kinase-1 variant is up-regulated in hypoxia and preeclampsia," J. Clin. Endocrinol. Metabol. 94:2524-2530.
Tuschl (2002) "Expanding small RNA interference," Nat. Biotechnol. 20(5):446-448.
Tuschl et al. (May 6, 2004) "The siRNA User Guide," Accessible on the Internet at URL: http://diyhpl.us/~bryan/irc/protocol-online/protocol-cache/sima.html. [Last Accessed Aug. 11, 2016].
Vaught et al. (2004) "T7 RNA Polymerase Transcription with 5-Position Modified UTP Derivatives," J. Am. Chem. Soc. 126:11231-11237.
Vorobjev et al. (2001) "Nuclease resistance and RNase H sensitivity of oligonucleotides bridged by oligomethylenediol and oligoethylene glycol linkers," Antisense Nucleic Acid Drug Dev. 11(2):77-85.
Watanabe et al. (2008) "Endogenous siRNAs from naturally formed dsRNAs regulate transcripts in mouse oocytes," Nature. 453(7194):539-543.
Wooddell et al. (Feb. 26, 2013) "Hepatocyte-targeted RNAi Therapeutics for the Treatment of Chronic Hepatitis B Virus Infection," Molecular Therapy. 21:973-985.
Xia et al. (2002) "siRNA-mediated gene silencing in vitro and in vivo," Nature Biotechnol. 20(10):1006-1010.
Young et al. (2010) "Pathogenesis of preeclampsia," Annual Review of Pathology. 5:173-192.
Younis et al. (2013) "Overview of the Nonclinical Development Strategies and Class-Effects of Oligonucleotide-Based Therapeutics," Ch. 26 In; A Comprehensive Guide to Toxicology in Preclinical Drug Development. Ed.: Faqi. Academic Press. pp. 647-664.
Alexopoulou et al. (2001) "Recognition of double-stranded RNA and activation of NF-κB by Toll-like receptor 3," Nature. 413:732-738.

Allerson et al. (2005) "Fully 2'-Modified Oligonucleotide Duplexes with Improved in Vitro Potency and Stability Compared to Unmodified Small Interfering RNA," J. Med. Chem. 48(4):901-904.
Khvorova et al. (Mar. 15, 2016) "Abstract IA27: Advances in oligonucleotide chemistry for the treatment of neurodegenerative disorders and brain tumors," Cancer Res. 76(6) Abstract No. IA27.
Altschul et al. (1997) "Gapped BLAST and PSI-BLAST: a new generation of protein database search programs," Nucleic Acids Res. 25(17):3389-3402.
Ameres et al. (2007) "Molecular basis for target RNA recognition and cleavage by human RISC," Cell. 130:101-112.
Anderson et al. (2008) "Experimental validation of the importance of seed complement frequency to siRNA specificity," RNA. 14:853-861.
Anderson et al. (2008) "Identifying siRNA-induced off-targets by microarray analysis," Ch.4 In; Methods in Molecular Biology. 442:45-63.
Bagella et al. (1998) "Cloning of murine CDK9/PITALRE and its tissue-specific expression in development," J. Cell. Physiol. 177:206-213.
Bartlett (2006) "Insights into the kinetics of siRNA-mediated gene silencing from live-cell and live-animal bioluminescent imaging," Nucleic Acids Research. 34:322-333.
Behlke et al. (2008) "Chemical modification of siRNAs for in vivo use," Oligonucleotides. 18:305-320.
Billy et al. (2001) "Specific interference with gene expression induced by long, double-stranded RNA in mouse embryonal teratocarcinoma cell lines," Proc Natl Acad Sci USA. 98(25)14428-14433.
Birmingham et al. (2006) "3' UTR seed matches, but not overall identity, are associated with RNAi off-targets," Nat. Methods. 3:199-204.
Birmingham et al. (2007) "A protocol for designing siRNAs with high functionality and specificity," Nature Protocols. 2:2068-2078.
Braasch et al. (2003) "RNA Interference in Mammalian Cells by Chemically-Modified RNA," Biochemistry 42:7967-7975.
Brennecke et al. (2003) "Towards a complete description of the microRNA complement of animal genomes," Genome Biol. 4(9):228.
Brummelkamp et al. (2002) "A system for stable expression of short interfering RNAs in mammalian cells," Science. 296:550-553.
Burchard et al. (2009) "MicroRNA-like off-target transcript regulation by siRNAs is species specific," RNA. 15:308-315.
Byrne et al. (Nov. 1, 2013) "Novel hydrophobically modified asymmetric RNAi compounds (sd-rxRNA) demonstrate robust efficacy in the eye," Journal of Ocular Pharmacology and Therapeutics. 29:855-864.
Calegari et al. (2002) "Tissue-specific RNA interference in postimplantation mouse embryos with endoribonuclease-prepared short interfering RNA," Proc. Natl. Acad. Sci. USA. 99(22):14236-14240.
Charrier et al. (May 3, 2012) "Inhibition of SRGAP2 function by its human-specific paralogs induces neoteny during spine maturation," Cell. 149(4):923-935.
Cho et al. (Feb. 13, 2012) "Vascular endothelial growth factor receptor 1 morpholino decreases angiogenesis in a murine corneal suture model," Invest. Opthamol. Visual Sci. 53(2):685-692.
Choe et al. (2005) "Crystal structure of human toll-like receptor 3 (TLR3) ectodomain," Science. 309:581-585.
Coelho et al. (Aug. 29, 2013) "Safety and efficacy of RNAi therapy for transthyretin amyloidosis," The New England Journal of Medicine. 369:819-829.
Deleavey et al. (Jan. 5, 2013) "The 5' binding MID domain of human Argonaute2 tolerates chemically modified nucleotide analogues" Nucleic Acid Therapeutics. 23:81-87.
Difiglia et al. (2007) "Therapeutic silencing of mutant huntingtin with siRNA attenuates striatal and cortical neuropathology and behavioral deficits," Proc. Natl. Acad. Sci. USA. 104(43):17204-17209.
Doench et al. (2003) "siRNAs can function as miRNAs," Genes Dev. 17(4):438-442.
Eckstein (2000) "Phosphorothioate Oligodeoxynucleotides: What is Their Origin and What is Unique About Them?" Antisense Nucleic Acid Drug Dev. 10(2):117-121.

(56) References Cited

OTHER PUBLICATIONS

Elmen et al. (2005) "Locked nucleic acid (LNA) mediated improvements in siRNA stability and functionality," Nucleic Acids Res. 33(1):439-4-47.
Fan et al. (Oct. 20, 2014) "Endometrial VEGF induces placental sFLT1 and leads to pregnancy complications," J. Clin. Inves. 124(11):4941-4952.
Federov et al. (2006) "Off-target effects by siRNA can induce toxic phenotype," RNA. 12:1188-1196.
Felber et al. (Sep. 2012) "The interactions of amphiphilic antisense oligonucleotides with serum proteins and their affects on in vitro silencing activity," Biomaterials. 33(25):5955-5965.
Frazier (Nov. 9, 2015) "Antisense Oligonucleotide Therapies: The Promise and the Challenges from a Toxicologic Pathologist's Perspective," Toxicologic Pathology. 43:78-89.
Gaglione et al. (2010) "Recent progress in chemically modified siRNAs," Mini Rev. Med. Chem. 10(7):578-595.
Godard et al. (1995) "Antisense Effects of Cholesterol-Oligodeoxynucleotide Conjugates Associated with Poly (alkylcyanoacrylate) Nanoparticles," Eur. J. Biochem. 232(2):404-410.
Grad et al. (2003) "Computational and experimental identification of C. elegans microRNAs," Mol. Cell. 11(5):1253-1263.
Griffiths-Jones (2004) "The microRNA Registry," Nuc. Acids Res. 32(Database Issue):D109-D111.
Grimm et al. (2006) "Fatality in mice due to oversaturation of cellular microRNA/short hairpin RNA pathways," Nature. 441:537-541.
Herdewijn (2000) "Heterocyclic modifications of oligonucleotides and antisense technology," Antisense Nucleic Acid Drug Dev. 10(4):297-310.
Heydarian et al. (2009) "Novel splice variants of sFlt1 are upregulated in preeclampsia," Placenta. 30:250-255.
Heyer et al. (Dec. 12, 2014) "An optimized kit-free method for making strand-specific deep sequencing libraries from RNA fragments," Nucleic Acids Res. 43(1):e2. pp. 1-14.
Hutvagner et al. (2002) "A microRNA in a multiple-turnover RNAi enzyme complex," Science. 297(5589):2056-2060.
Jackson et al. (2006) "Position-specific chemical modification of siRNAs reduces 'off-target' transcript silencing," RNA. 12:1197-1205.
Jackson et al. (2010) "Recognizing and avoiding siRNA off-target effects for target identification and therapeutic application," Nature Reviews in Drug Discovery. 9:57-67.
Jacque et al. (2002) "Modulation of HIV-1 replication by RNA interference," Nature. 418:435-438.
Judge et al. (2006) "Design of Noninflammatory Synthetic siRNA Mediating Potent Gene Silencing in Vivo," Molecular Therapy. 13:494-505.
Karlin et al. (1990) "Methods for assessing the statistical significance of molecular sequence features by using general scoring schemes," Proc. Natl. Acad. Sci. USA. 87:2264-2268.
Karlin et al. (1993) "Applications and statistics for multiple high-scoring segments in molecular sequences," Proc. Natl. Acad. Sci. USA 90:5873-5877.
Kenski et al. (2012) "siRNA-optimized Modifications for Enhanced In Vivo Activity," Mol. Ther. Nucleic Acids. 1:e5. pp. 1-8.
Khvorova et al. (2003) "Functional siRNAs and miRNAs Exhibit Strand Bias," Cell. 115:209-216.
Pubchem Database [Online] (2003) "Amino-Teg-Diol," PubChem Accession No. 22136768. National Institute for Biotechnology Information. Accessible on the Internet at URL: https://pubchem.ncbi.nlm.nih.gov/compound/2213676. [Last Accessed Aug. 31, 2017], 13 pgs.
Pubchem Database [Online] (2005) "SCHEMBL867745," PubChem Accession No. 12454428. National Institute for Biotechnology Information. Accessible on the Internet at URL: https://pubchem.ncbi.nlm.nih.gov/compound/12454428. [Last Accessed Aug. 31, 2017], 12 pgs.
International Search Report with Written Opinion corresponding to International Patent Application No. PCT/US2017/015633, dated May 11, 2017.
Avino et al. (2011) "Branched RNA: A New Architecture for RNA Interference," Journal of Nucleic Acids, 7 pages.
Chang et al. (2012) "Enhanced intracellular delivery and multi-target gene silencing triggered by tripodal RNA structures," J. Gene Med., 14:138-146.
Mok et al., (2010) "Multimeric small interfering ribonucleic acid for highly efficient sequence-specific gene silencing," Nature Materials, 9:272-278.
Lee et al., (2012) "Small-interfering RNA (siRNA)-based functional micro-and nanostructures for efficient and selective gene silencing," Accounts of Chemical Research, 45(7):1014-1025.
Extended European Search Report for European Application No. 17745083.0, dated Jul. 31, 2019, (7 pages).
Alterman et al., "Hydrophobically Modified siRNAs Silence Huntingtin mRNA in Primary Neurons and Mouse Brain", Molecular Therapy-Nucleic Acids, vol. 4 No. 12, Dec. 1, 2015, p. e266.
Yu et al. (2002) "RNA interference by expression of short-interfering RNAs and hairpin RNAs in mammalian cells," Proc Natl Acad Sci USA. 99:6047-6052.
Yu et al. (Aug. 31, 2012) "Single-stranded RNAs use RNAi to potently and allele-selectively inhibit mutant huntingtin expression," Cell. 150(5):895-908.
Zeng et al. (2002) "Both natural and designed micro RNAs can inhibit the expression of cognate mRNAs when expressed in human cells," Mol. Cell. 9(6):1327-1333.
Zeng et al. (2003) "Sequence requirements for micro RNA processing and function in human cells," RNA. 9(1):112-123.
International Search Report with Written Opinion corresponding to International Patent Application No. PCT/US2016/025722, dated Aug. 12, 2016.
International Search Report with Written Opinion corresponding to International Patent Application No. PCT/US2016/025731, dated Sep. 9, 2016.
International Search Report with Written Opinion corresponding to International Patent Application No. PCT/US2016/025753, dated Sep. 14, 2016.
International Search Report with Written Opinion corresponding to International Patent Application No. PCT/US2016/046810, dated Nov. 29, 2016.
U.S. Appl. No. 15/089,319 / 2016/0355808, filed Apr. 1, 2016 / Dec. 8, 2016, Anastasia Khvorova.
U.S. Appl. No. 15/089,437 / 2016/0355826, filed Apr. 1, 2016 / Dec. 8, 2016, Anastasia Khvorova.
U.S. Appl. No. 15/089,423 / 2016/0319278, filed Apr. 1, 2016 / Nov. 3, 2016, Anastasia Khvorova.
U.S. Appl. No. 15/236,051 / 2017/0043024, filed Aug. 12, 2016 / Feb. 16, 2017, Anastasia Khvorova.
U.S. Appl. No. 15/419,593, filed Jan. 30, 2017, Anastasia Khvorova.

\* cited by examiner

Linkers and Spacers

Polypeptides

Branching Moieties

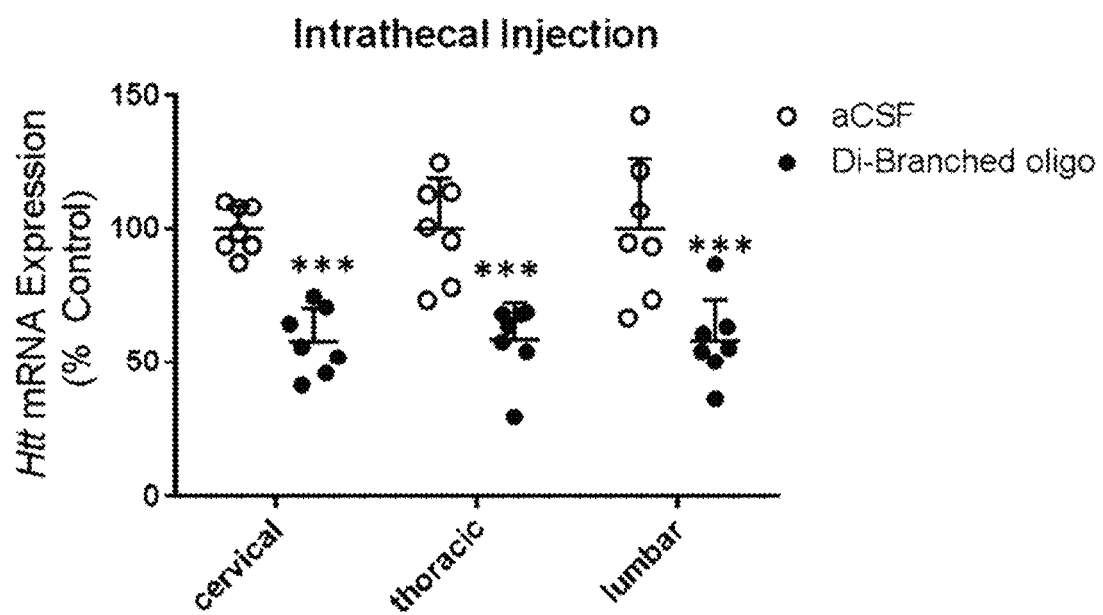
*Fig. 14A*
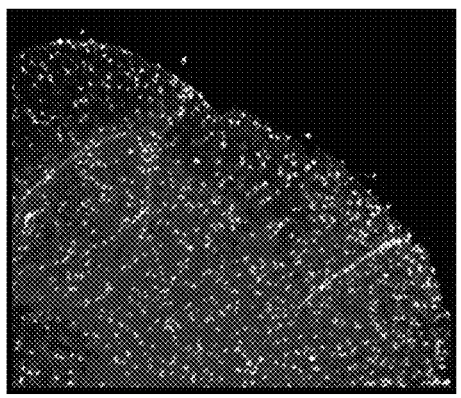 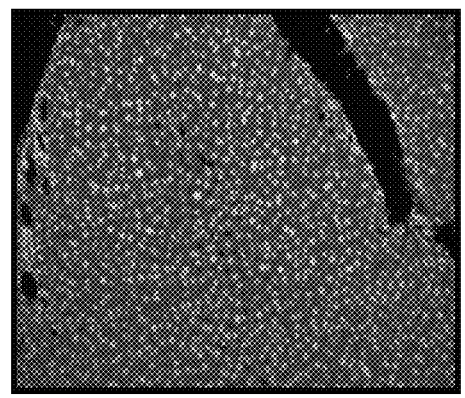
*Fig. 14B*          *Fig. 14C*

Where X is (C)n or (CO)n or (COC)n or (CONH)n or mixture of therein
Where Y is (C)n or (CO)n or (COC)n or (CONH)n or mixture of therein or spacer or divider, cleavable or not
Where W is a bioactive conjugate (right)

```
                    R3
      R1=U-A-A-U-C-U-C-U-U-A-C-U-G-A-U-A-U-A  (5'-3')
         . . . . . . . . . . . . . . . . . .
        A-A-U-A-G-A-G-A-A-A-U-G-A-C           (3'-5')
                    R3

R1=U-A-A-U-C-U-C-U-U-A-C-U-G-A-U-A-U-A  (5'-3')
         . . . . . . . . . . . . . . . . . .
        A-A-U-A-G-A-G-A-A-A-U-G-A-C           (3'-5')
```

Legend

X— 2'-deoxy-2'-fluoro

X— 2'-O-methyl

R1=5'— E-VP-mU  
$C_{12}H_{18}N_2O_9P_2S$, Molecular Weight: 428.29

L=3'— TEG phosphoramidate  
$C_{12}H_{25}NO_{10}P_2^{2-}$, Molecular Weight: 405.28

Legend x – 2'-deoxy-2'-fluoro x – 2'-O-methyl

R1=5'-E-VP-mU
$C_{12}H_{18}NO_9P_3S$, Molecular Weight: 428.29

L=3'- TEG Di Phosphate
$C_{11}H_{22}O_{11}P_2^{2-}$, Molecular Weight: 392.23

BRANCHED OLIGONUCLEOTIDES

RELATED APPLICATIONS

This application is a division of U.S. patent application Ser. No. 15/419,593, filed Jan. 30, 2017, which claims priority to U.S. Provisional Patent Application Nos. 62/289,268, filed Jan. 31, 2016, and 62/317,113, filed Apr. 1, 2016. The contents of the aforementioned applications are incorporated by reference herein for all purposes.

STATEMENT OF FEDERALLY SPONSORED RESEARCH

This invention was made with government support under Grant No. GM108803 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Apr. 17, 2019, is named 612182_UM9-213DIV_ST25.txt and is 10,310 bytes in size.

TECHNICAL FIELD

This disclosure relates to novel branched oligonucleotides designed to achieve unexpectedly high efficacy, uptake and tissue distribution.

BACKGROUND

Therapeutic oligonucleotides are simple and effective tools for a variety of applications, including the inhibition of gene function. An example of such inhibition is RNA interference (RNAi). The promise of RNAi as a general therapeutic strategy, however, depends on the ability to deliver small RNAs to a wide range of tissues. Currently, small therapeutic RNAs can only be delivered effectively to liver. There remains a need for self-delivering siRNA, and therapeutic oligonucleotides in general, that exhibit minimal immune response and off-target effects, efficient cellular uptake without formulation, and efficient and specific tissue distribution.

SUMMARY

Accordingly, the present disclosure provides branched oligonucleotides ("compounds of the invention") exhibiting unexpected improvement in distribution, in vivo efficacy and safety.

In a first aspect, provided herein is a branched oligonucleotide compound comprising two or more nucleic acids, the nucleic acids are connected to one another by one or more moieties selected from a linker, a spacer and a branching point.

In an embodiment, the branched oligonucleotide comprises 2, 3, 4, 6 or 8 nucleic acids.

In an embodiment of the branched oligonucleotide, each nucleic acid is single-stranded and has a 5' end and a 3' end, and each nucleic acid is independently connected to a linker, a spacer, or a branching point at the 5' end or at the 3' end.

In an embodiment, each single-stranded nucleic acid independently comprises at least 15 contiguous nucleotides. In an embodiment, the antisense strand comprises at least 15, at least 16, at least 17, at least 18, at least 19, or at least 20 contiguous nucleotides, and has complementarity to a target.

In an embodiment, each nucleic acid comprises one or more chemically-modified nucleotides. In an embodiment, each nucleic acid consists of chemically-modified nucleotides.

In an embodiment of the branched oligonucleotide, each nucleic acid is double-stranded and comprises a sense strand and an antisense strand, the sense strand and the antisense strand each have a 5' end and a 3' end. In an embodiment, each double-stranded nucleic acid is independently connected to a linker, spacer or branching point at the 3' end or at the 5' end of the sense strand or the antisense strand.

In an embodiment, the sense strand and the antisense strand each comprise one or more chemically-modified nucleotides. In an embodiment, the sense strand and the antisense strand each consist of chemically-modified nucleotides. In an embodiment, the sense strand and the antisense strand both comprise alternating 2'-methoxy-nucleotides and 2'-fluoro-nucleotides. In an embodiment, the nucleotides at positions 1 and 2 from the 5' end of the sense and antisense strands are connected to adjacent nucleotides via phosphorothioate linkages. In an embodiment, the nucleotides at positions 1-6 from the 3' end, or positions 1-7 from the 3' end, are connected to adjacent nucleotides via phosphorothioate linkages.

In an embodiment, the branched oligonucleotide further comprises a hydrophobic moiety. In a particular embodiment, the hydrophobic moiety is attached to one or more terminal 5' positions of the branched oligonucleotide compound. The hydrophobic moiety may be comprised within one or more 5' phosphate moieties. In certain embodiments, the hydrophobic moiety comprises an alkyl or alkenyl moiety (e.g., an alkyl or alkenyl chain, or a saturated or unsaturated fatty acid residue), a vitamin or cholesterol derivative, an aromatic moiety (e.g., phenyl or naphthyl), a lipophilic amino acid or a combination thereof. Certain embodiments of hydrophobic moieties, and strategies for synthesizing hydrophobically modified branched oligonucleotide compounds, are depicted in FIG. 44.

In an embodiment of the branched oligonucleotide, each linker is independently selected from an ethylene glycol chain, an alkyl chain, a peptide, RNA, DNA, a phosphate, a phosphonate, a phosphoramidate, an ester, an amide, a triazole, and combinations thereof any carbon or oxygen atom of the linker is optionally replaced with a nitrogen atom, bears a hydroxyl substituent, or bears an oxo substituent.

In a second aspect, provided herein is a compound of formula (I):

$$L-(N)_n \qquad (I)$$

L is selected from an ethylene glycol chain, an alkyl chain, a peptide, RNA, DNA, a phosphate, a phosphonate, a phosphoramidate, an ester, an amide, a triazole, and combinations thereof, formula (I) optionally further comprises one or more branch point B, and one or more spacer S; B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof; N is an RNA duplex comprising a sense strand and an antisense strand, the sense strand and antisense strand each independently comprise one or more chemical modifications; and n is 2, 3, 4, 5, 6, 7 or 8.

In an embodiment, the compound of formula (I) has a structure selected from formulas (I-1)-(I-9) of Table 1.
In an embodiment, each antisense strand independently comprises a 5' terminal group R selected from the groups of Table 2.
TABLE 1
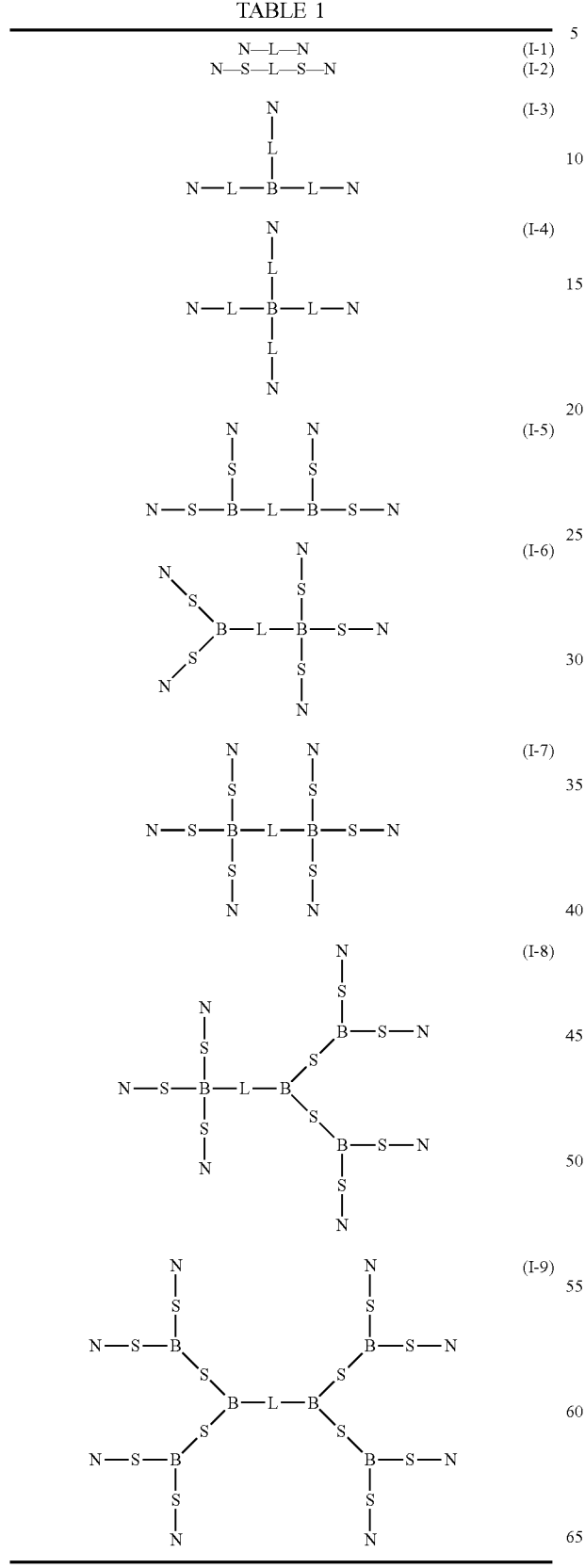
TABLE 2
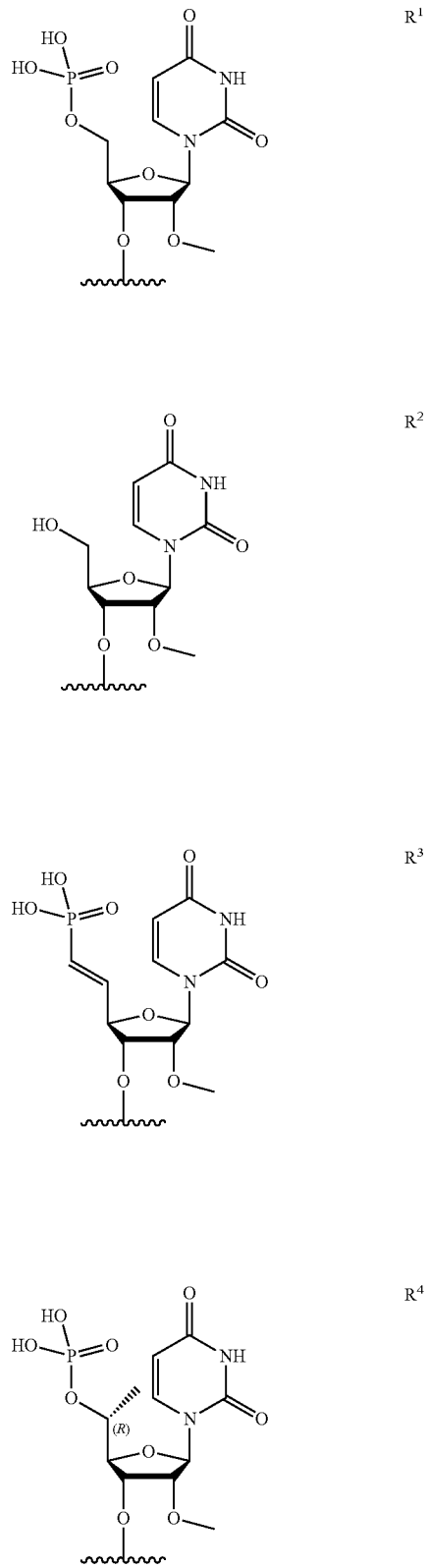

TABLE 2-continued

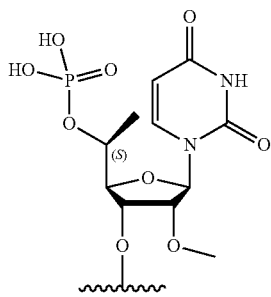

R⁵

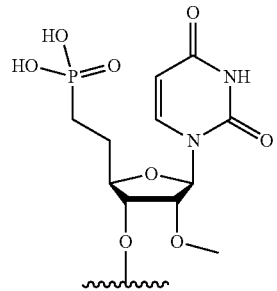

R⁷

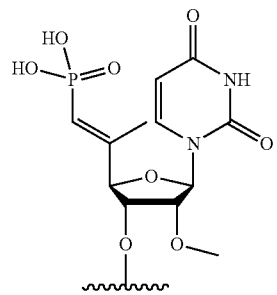

R⁸

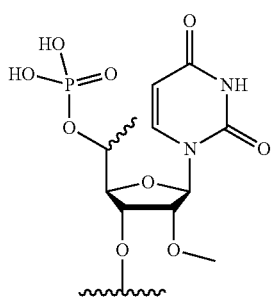

R⁶

In an embodiment, the compound of formula (I) the structure of formula (II):

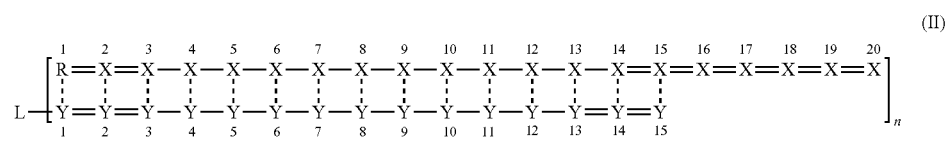

(II)

X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; — represents a phosphodiester internucleoside linkage; = represents a phosphorothioate internucleoside linkage; and ≡ represents, individually for each occurrence, a base-pairing interaction or a mismatch.

In an embodiment, the compound of formula (I) has the structure of formula (III):

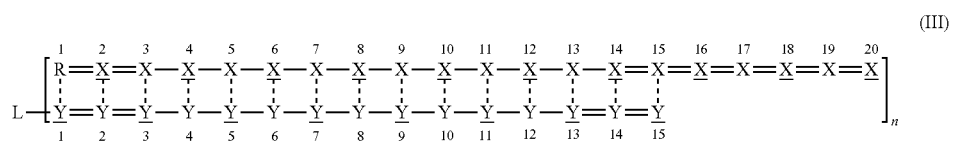

(III)

$\underline{X}$, for each occurrence, independently, is a nucleotide comprising a 2'-deoxy-2'-fluoro modification; X, for each occurrence, independently, is a nucleotide comprising a 2'-O-methyl modification; $\underline{Y}$, for each occurrence, independently, is a nucleotide comprising a 2'-deoxy-2'-fluoro modification; and Y, for each occurrence, independently, is a nucleotide comprising a 2'-O-methyl modification.

In an embodiment, the compound of formula (I) has the structure of formula (IV) (SEQ ID NOS 1 and 2, respectively, in order of appearance):

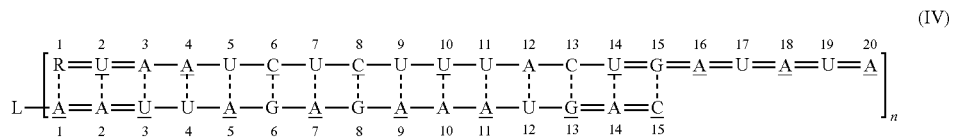

A is an adenosine comprising a 2'-deoxy-2'-fluoro modification; A is an adenosine comprising a 2'-O-methyl modification; G is an guanosine comprising a 2'-deoxy-2'-fluoro modification; G is an guanosine comprising a 2'-O-methyl modification; U is an uridine comprising a 2'-deoxy-2'-fluoro modification; U is an uridine comprising a 2'-O-methyl modification; C is an cytidine comprising a 2'-deoxy-2'-fluoro modification; and C is an cytidine comprising a 2'-O-methyl modification.

In an embodiment, the compound of formula (I) has the structure of formula (V):

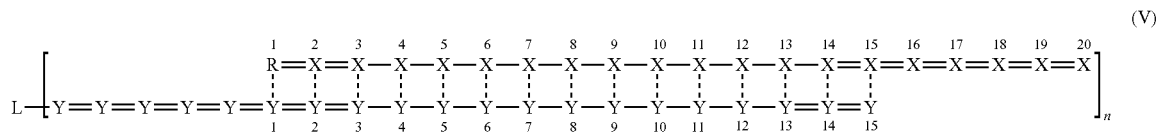

X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; — represents a phosphodiester internucleoside linkage; = represents a phosphorothioate internucleoside linkage; and ≡ represents, individually for each occurrence, a base-pairing interaction or a mismatch.

In an embodiment, the compound of formula (I) has the structure of formula (VI):

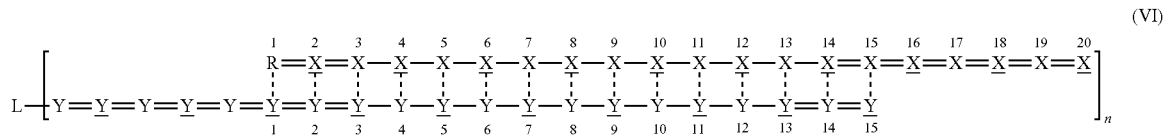

X, for each occurrence, independently, is a nucleotide comprising a 2'-deoxy-2'-fluoro modification; X, for each occurrence, independently, is a nucleotide comprising a 2'-O-methyl modification; Y, for each occurrence, independently, is a nucleotide comprising a 2'-deoxy-2'-fluoro modification; and Y, for each occurrence, independently, is a nucleotide comprising a 2'-O-methyl modification.

In an embodiment, the compound of formula (I) has the structure of formula (VII) (SEQ ID NOS 3 and 4, respectively, in order of appearance):

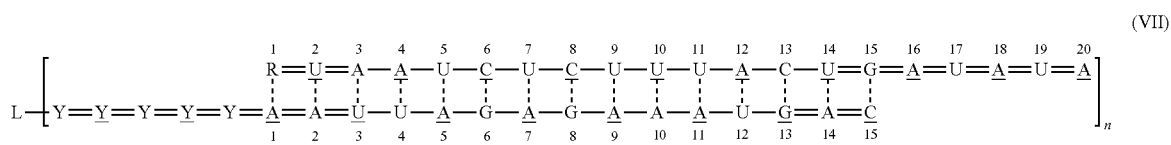

A is an adenosine comprising a 2'-deoxy-2'-fluoro modification; A is an adenosine comprising a 2'-O-methyl modification; G is an guanosine comprising a 2'-deoxy-2'-fluoro modification; G is an guanosine comprising a 2'-O-methyl modification; U is an uridine comprising a 2'-deoxy-2'-fluoro modification; U is an uridine comprising a 2'-O-methyl modification; C is an cytidine comprising a 2'-deoxy-2'-fluoro modification; C is an cytidine comprising a 2'-O-methyl modification; Y, for each occurrence, independently, is a nucleotide comprising a 2'-deoxy-2'-fluoro modification; and Y, for each occurrence, independently, is a nucleotide comprising a 2'-O-methyl modification.

In an embodiment of the compound of formula (I), L has the structure of L1:

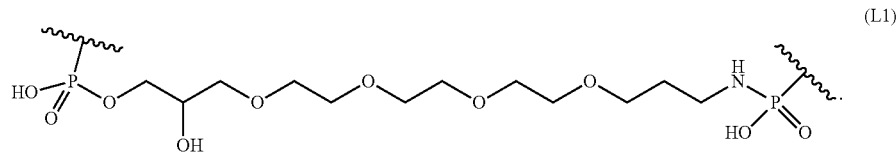 [SMILES: *P(=O)(O)NCCCOCCOCCOCCOCC(O)COP(*)(=O)O]

(L1)

In an embodiment of L1, R is $R^3$ and n is 2.

In an embodiment of the compound of formula (I), L has the structure of L2:

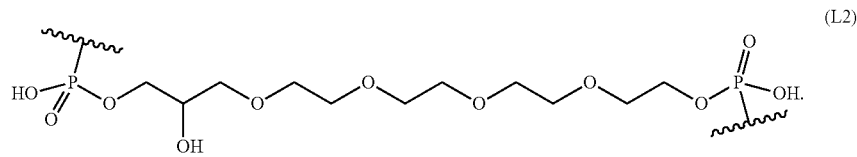 [SMILES: *P(=O)(O)OCCOCCOCCOCCOCC(O)COP(*)(=O)O]

(L2)

In an embodiment of L2, R is $R^3$ and n is 2.

In a third aspect, provided herein is a delivery system for therapeutic nucleic acids having the structure of formula (VIII):

$$L-(cNA)_n \quad \text{(VIII)}$$

L is selected from an ethylene glycol chain, an alkyl chain, a peptide, RNA, DNA, a phosphate, a phosphonate, a phosphoramidate, an ester, an amide, a triazole, and combinations thereof, formula (VIII) optionally further comprises one or more branch point B, and one or more spacer S; B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof; each cNA, independently, is a carrier nucleic acid comprising one or more chemical modifications; and n is 2, 3, 4, 5, 6, 7 or 8.

In an embodiment, the compound of formula (VIII) has a structure selected from formulas (VIII-1)-(VIII-9) of Table 3:

TABLE 3

| | |
|---|---|
| ANc—L—cNA | (VIII-1) |
| ANc—S—L—S—cNA | (VIII-2) |

TABLE 3-continued

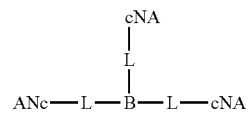

(VIII-3)

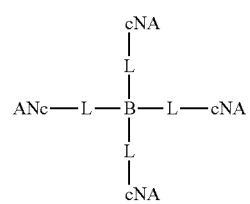

(VIII-4)

TABLE 3-continued

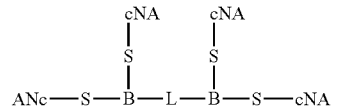

(VIII-5)

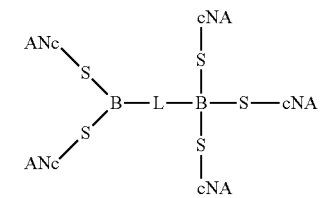

(VIII-6)

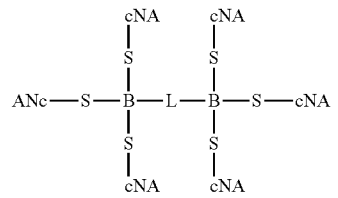

(VIII-7)

TABLE 3-continued

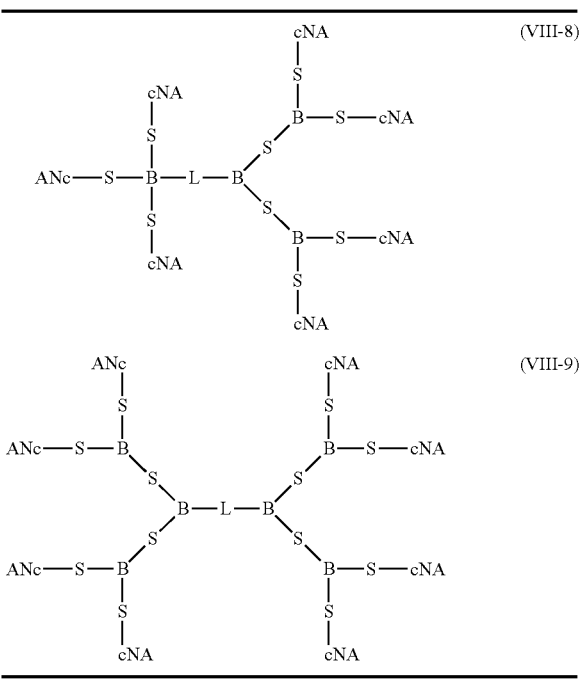

In an embodiment, the compound of formulas (VIII) (including, e.g., formulas (VIII-1)-(VIII-9), each cNA independently comprises at least 15 contiguous nucleotides. In an embodiment, each cNA independently consists of chemically-modified nucleotides.

In an embodiment, the delivery system further comprises n therapeutic nucleic acids (NA), each NA is hybridized to at least one cNA.

In an embodiment, each NA independently comprises at least 16 contiguous nucleotides. In an embodiment, each NA independently comprises 16-20 contiguous nucleotides. In an embodiment, each NA comprises an unpaired overhang of at least 2 nucleotides. In an embodiment, the nucleotides of the overhang are connected via phosphorothioate linkages.

In an embodiment, each NA, independently, is selected from the group consisting of: DNA, siRNAs, antagomiRs, miRNAs, gapmers, mixmers, or guide RNAs. In an embodiment, each NA is the same. In an embodiment, each NA is not the same.

In an embodiment, the delivery system further comprising n therapeutic nucleic acids (NA) has a structure selected from formulas (I), (II), (III), (IV), (V), (VI), (VII), and embodiments thereof described herein.

In an embodiment of the delivery system, the target of delivery is selected from the group consisting of: brain, liver, skin, kidney, spleen, pancreas, colon, fat, lung, muscle, and thymus.

BRIEF DESCRIPTION OF THE DRAWINGS

FIG. 10A—HeLa cells were transfected (using RNAiMax) with Di-branched oligo at concentrations shown for 72 hours. FIG. 10B—Primary cortical mouse neurons were treated with Di-branched oligo at concentrations shown for 1 week. mRNA was measured using Affymetrix Quantigene 2.0. Data was normalized to housekeeping gene (PPIB) and graphed as % of untreated control. FIG. 10C—HeLa cells were treated passively (no formulation) with Di-siRNA oligo at concentrations shown for 1 week.

FIG. 13A—Robust Htt mRNA silencing in both Cortex and Striatum 7 days after single IS injection (25 ug), QuantiGene®. FIG. 13B—Levels of hsiRNA accumulation in tissues 7 days after injection (PNA assay).

FIGS. 14A-14C show wide distribution and efficacy throughout the spinal cord following bolus intrathecal injection of Di-hsiRNA. Intrathecal injection in lumbar of 3 nmols Di-branched Oligo (6 nmols of corresponding antisense HTT strand). FIG. 14A—Robust Htt mRNA silencing in all region of spinal cord, 7 days, n-6. Animals sacrificed 7 days post-injection. Tissue punches taken from cervical, thoracic and lumbar regions of spinal cord. mRNA was quantified using Affymetrix Quantigene 2.0 as per Coles et al. 2015. Data normalized to housekeeping gene, HPRT, and graft as percent of aCSF control. aCSF—artificial CSF. FIG. 14B—Animals were injected lumbar IT with 75 ug of Cy3-Chol-hsiRNA, Cy-Di-hsiRNA. Chol-hsiRNAs shows steep gradient of diffusion from outside to inside of spinal cord. Di-hsiRNAs shows wide distribution throughout the cord (all regions). Leica 10× (20 mm bar). Image of Di-branched oligo in cervical region of spinal cord 48 hours after intrathecal injection. Red=oligo, Blue=Dapi. FIG. 14C—Image of Di-branched oligo in liver 48 hours after intrathecal injection. Red=oligo, Blue=Dapi.

FIG. 15B—asymmetrical branched oligonucleotides with 3' and 5' linkages to the linkers or spaces described previously. This can be applied the 3' and 5' ends of the sense strand or the antisense strands or a combination thereof; FIG. 15C—branched oligonucleotides made up of three separate strands. The long dual sense strand can be synthesized with 3' phosphoramidites and 5' phosphoramidites to allow for 3'-3' adjacent or 5'-5' adjacent ends.

FIG. 22A—Chemical composition of the four sub-products created from VitD-FM-hsiRNA synthesis and crude reverse phase analytical HPLC of the original chemical synthesis. FIG. 22B—Efficacy of sub-products in HeLa cells after lipid mediated delivery of hsiRNA. Cells were treated for 72 hours. mRNA was measured using QuantiGene 2.0 kit (Affymetrix). Data are normalized to housekeeping gene HPRT and presented as a percent of untreated control. FIG. 22C—A single, unilateral intrastriatal injection (25 µg) of each hsiRNA sub-product. Images taken 48 hours after injection.

FIG. 23A depicts a scatter dot plot showing Htt mRNA expression in the liver one week post intrastriatal injection of Di-HTT-Cy3 compared to a negative control (aCSF). FIG. 23B depicts a scatter dot plot showing Htt mRNA expression in the kidney one week post intrastriatal injection of Di-HTT-Cy3 compared to a negative control (aCSF).

FIG. 24A depicts a scatter dot plot showing Htt mRNA expression in the striatum one week post intrastriatal injection of Di-HTT, Di-HTT-Cy3, or two negative controls (aCSF or Di-NTC). FIG. 24B depicts a scatter dot plot showing Htt mRNA expression in the cortex one week post intrastriatal injection of Di-HTT, Di-HTT-Cy3, or two negative controls (aCSF or Di-NTC).

FIG. 26A depicts a scatter dot plot measuring Htt mRNA levels in the striatum and cortex two weeks post injection. FIG. 26B depicts a scatter dot plot measuring Htt protein levels in the striatum and cortex two weeks post injection.

FIG. 27A depicts a scatter dot plot measuring DARPP32 signal in the striatum and cortex two weeks after injection with Di-HTT-Cy3 or aCSF. FIG. 27B depicts a scatter dot plot measuring GFAP protein levels in the striatum and cortex two weeks after injection with Di-HTT-Cy3 or aCSF.

FIG. 30A depicts fluorescent imaging of sections of the striatum, cortex, and cerebellum. FIG. 30B depicts brightfield images of the whole brain injected with control (aCSF) or Di-HTT-Cy3. FIG. 30C depicts a fluorescent image of a whole brain section 48 hours after Di-HTT-Cy3 injection.

FIG. 38A depicts a scatter dot plot measuring HTT mRNA levels up to 12 days after intrastriatal injection. FIG. 38B depicts a scatter dot plot measuring HTT mRNA levels up to 28 days after intrastriatal injection.

FIG. 40 discloses SEQ ID NOS 5, 2, 5 and 2, respectively, in order of appearance.

FIG. 41 discloses SEQ ID NOS 5, 2, 5 and 2, respectively, in order of appearance.

FIG. 42 discloses SEQ ID NOS 5 and 2, respectively, in order of appearance.

FIG. 43 discloses SEQ ID NOS 5, 2, 5 and 2, respectively, in order of appearance.

DETAILED DESCRIPTION

Figure 1:
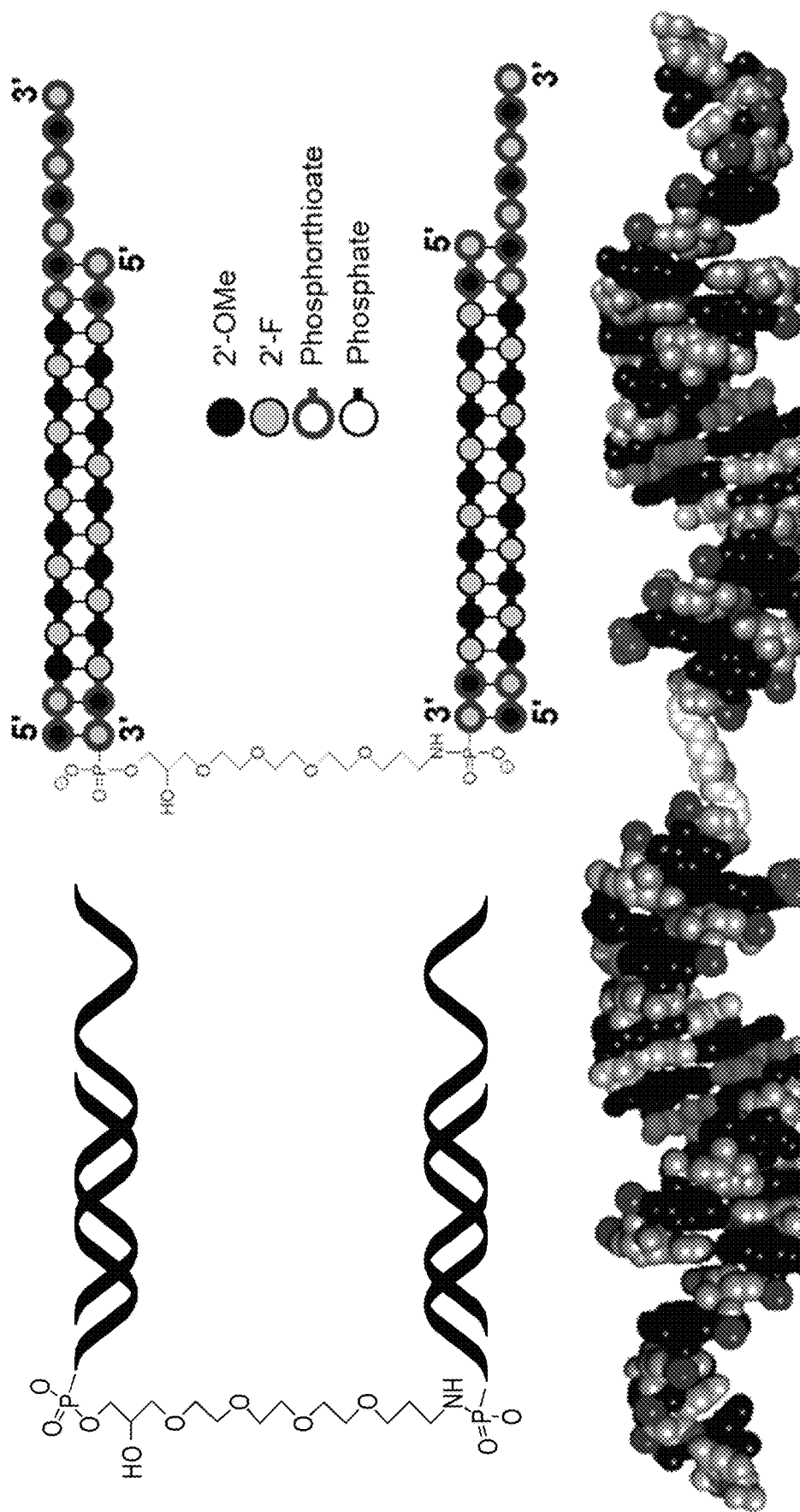
FIG. 1 shows the structure of Di-hsiRNAs. Black—2'-O-methyl, grey—2'-fluoro, red dash—phosphorothioate bond, linker—tetraethylene glycol. Di-hsiRNAs are two asymmetric siRNAs attached through the linker at the 3' ends of the sense strand. Hybridization to the longer antisense strand creates protruding single stranded fully phosphorthioated regions, essential for tissue distribution, cellular uptake and efficacy. The structures presented utilize teg linger of four monomers. The chemical identity of the linker can be modified without the impact on efficacy. It can be adjusted by length, chemical composition (fully carbon), saturation or the addition of chemical targeting ligands.

The present disclosure provides branched oligonucleotides ("compounds of the invention") exhibiting unexpected improvement in distribution, in vivo efficacy and safety. The branched oligonucleotides described herein efficiently and stably delivered small RNAs to multiple regions of the brain and multiple other organs, demonstrating unprecedented efficacy of delivery that has not been previously demonstrated with unconjugated small RNAs.

The compositions described herein allow efficient, stable delivery of siRNA in order to promote potent silencing of therapeutic target genes. The compositions exhibit therapeutic potential for many hard to treat diseases and overcome present challenges in employing RNA therapeutics.

In a first aspect, provided herein is a branched oligonucleotide compound comprising two or more nucleic acids, wherein the nucleic acids are connected to one another by one or more moieties selected from a linker, a spacer and a branching point.

Provided herein in various aspects and embodiments are branched oligonucleotides, referred to as compounds of the invention. In some embodiments, compounds of the invention have two to eight oligonucleotides attached through a linker. The linker may be hydrophobic. In a particular embodiment, compounds of the invention have two to three oligonucleotides. In one embodiment, the oligonucleotides independently have substantial chemical stabilization (e.g., at least 40% of the constituent bases are chemically-modified). In a particular embodiment, the oliogonucleotides have full chemical stabilization (i.e., all of the constituent bases are chemically-modified). In some embodiments, compounds of the invention comprise one or more single-stranded phosphorothioated tails, each independently having two to twenty nucleotides. In a particular embodiment, each single-stranded tail has eight to ten nucleotides.

In certain embodiments, compounds of the invention are characterized by three properties: (1) a branched structure, (2) full metabolic stabilization, and (3) the presence of a single-stranded tail comprising phosphorothioate linkers. In a particular embodiment, compounds of the invention have 2 or 3 branches. The increased overall size of the branched structures promote increased uptake. Also, without being bound by a particular theory of activity, multiple adjacent branches (e.g., 2 or 3) allow each branch to act cooperatively and thus dramatically enhance rates of internalization, trafficking and release.

Full metabolic stabilization of branched oligonucleotides of the invention results in unexpectedly high in vivo efficacy. Unstabilized branched siRNA lacks an in vivo efficacy. The presence of a single stranded tail is required for the activity of branched oligonucleotides. The phosphoroamidate functional group is crucial for the function of the di-branched oligos.

In certain embodiments, compounds of the invention are characterized by the following properties: (1) two or more branched oligonucleotides, e.g., wherein there is a non-equal number of 3' and 5' ends; (2) substantially chemically stabilized, e.g., wherein more than 40%, optimally 100%, of oligonucleotides are chemically modified (e.g., no RNA and optionally no DNA); and (3) phosphorothioated single oligonucleotides containing at least 3, optimally 5-20 phosphorothioated bonds.

Figure 7:
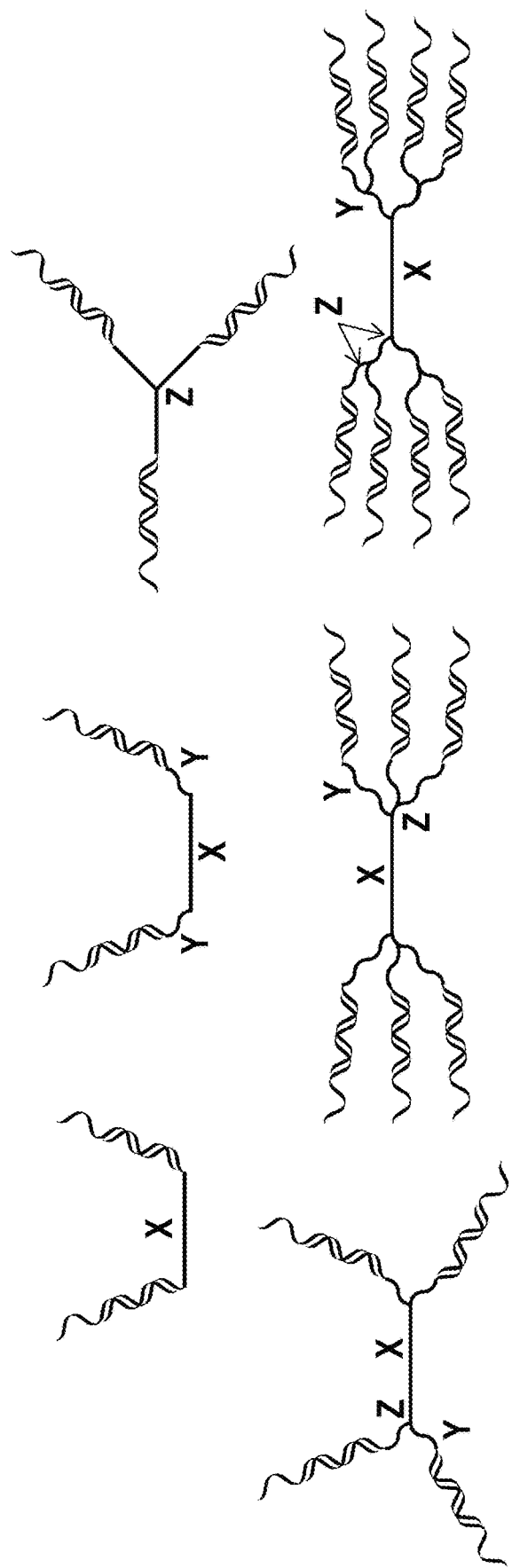
FIG. 7 shows oligonucleotide branching motifs. The double-helices represented oligonucleotides. The combination of different linkers, spacer and branching points allows generation of a wide diversity of branched hsiRNA structures.
Figure 8:
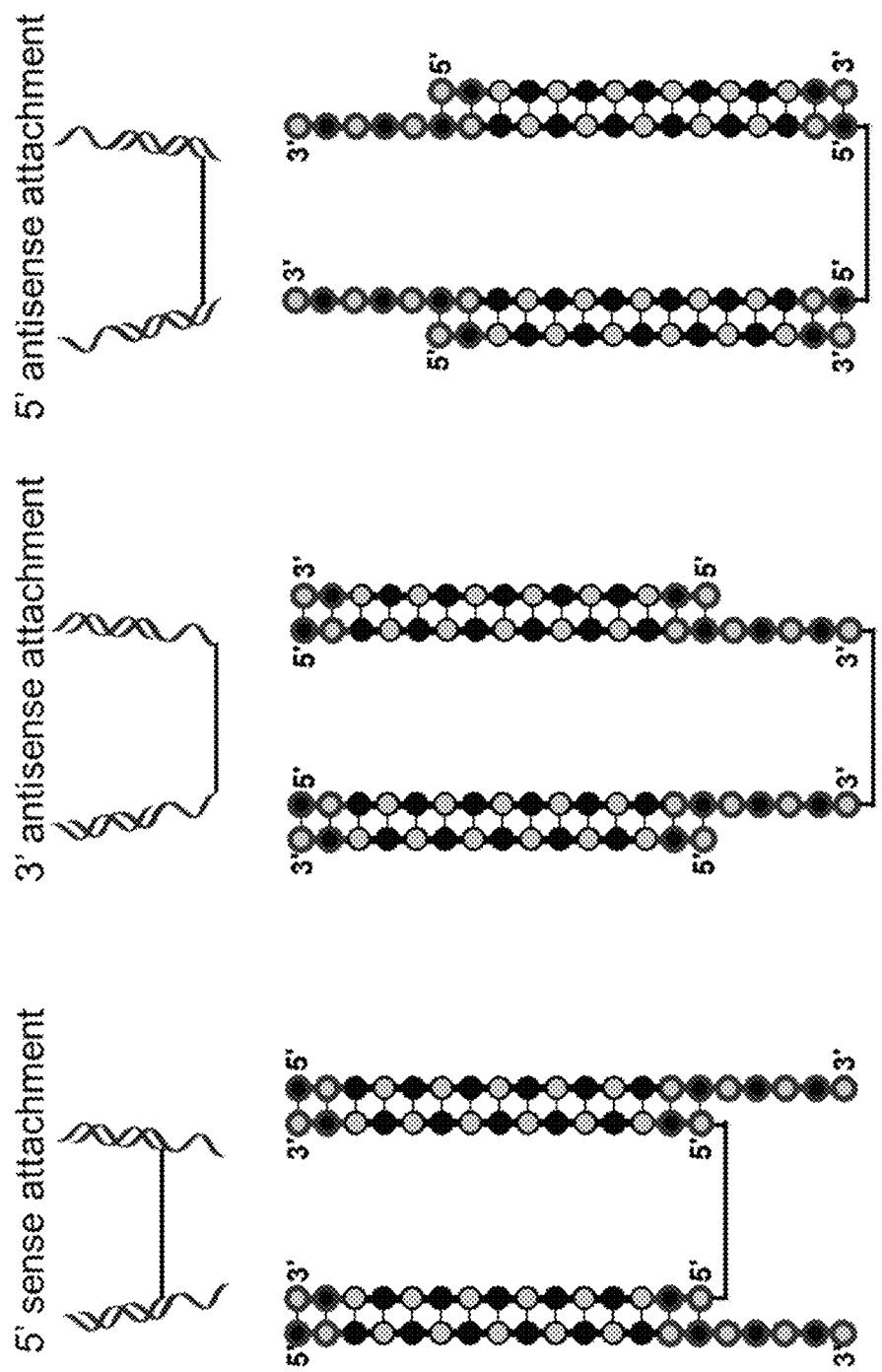
FIG. 8 shows structurally diverse branched oligonucleotides.
Figure 9:
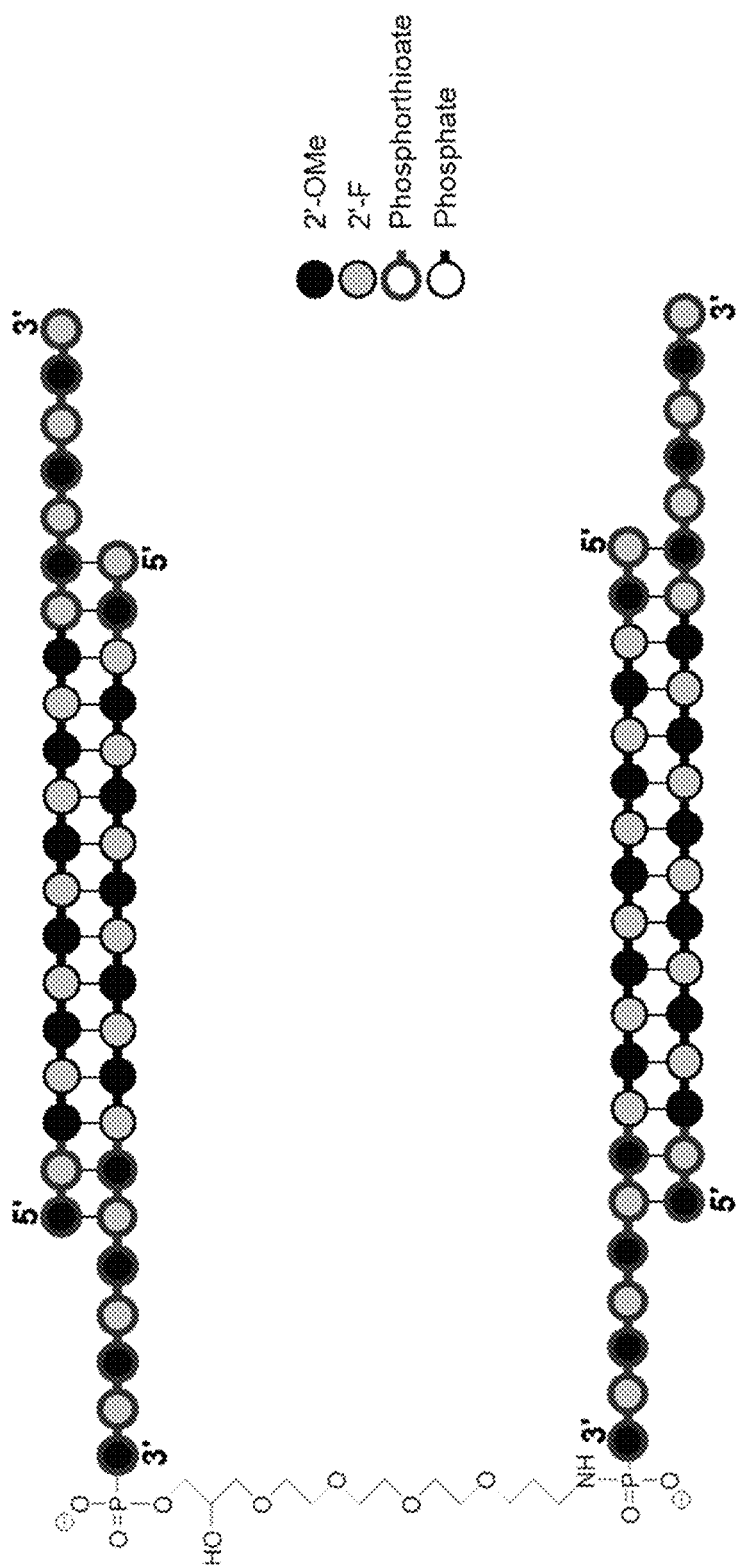
FIG. 9 shows an asymmetric compound of the invention having four single-stranded phosphorothioate regions.

Compounds of the invention are provided in various structurally diverse embodiments. As shown in FIG. 7, for example, in some embodiments oligonucleotides attached at the branching points are single stranded and consist of miRNA inhibitors, gapmers, mixmers, SSOs, PMOs, or PNAs. These single strands can be attached at their 3' or 5' end. Combinations of siRNA and single stranded oligonucleotides could also be used for dual function. In another embodiment, short oligonucleotides complementary to the gapmers, mixmers, miRNA inhibitors, SSOs, PMOs, and PNAs are used to carry these active single-stranded oligonucleotides and enhance distribution and cellular internalization. The short duplex region has a low melting temperature ($T_m \sim 37°$ C.) for fast dissociation upon internalization of the branched structure into the cell.

Figure 16:
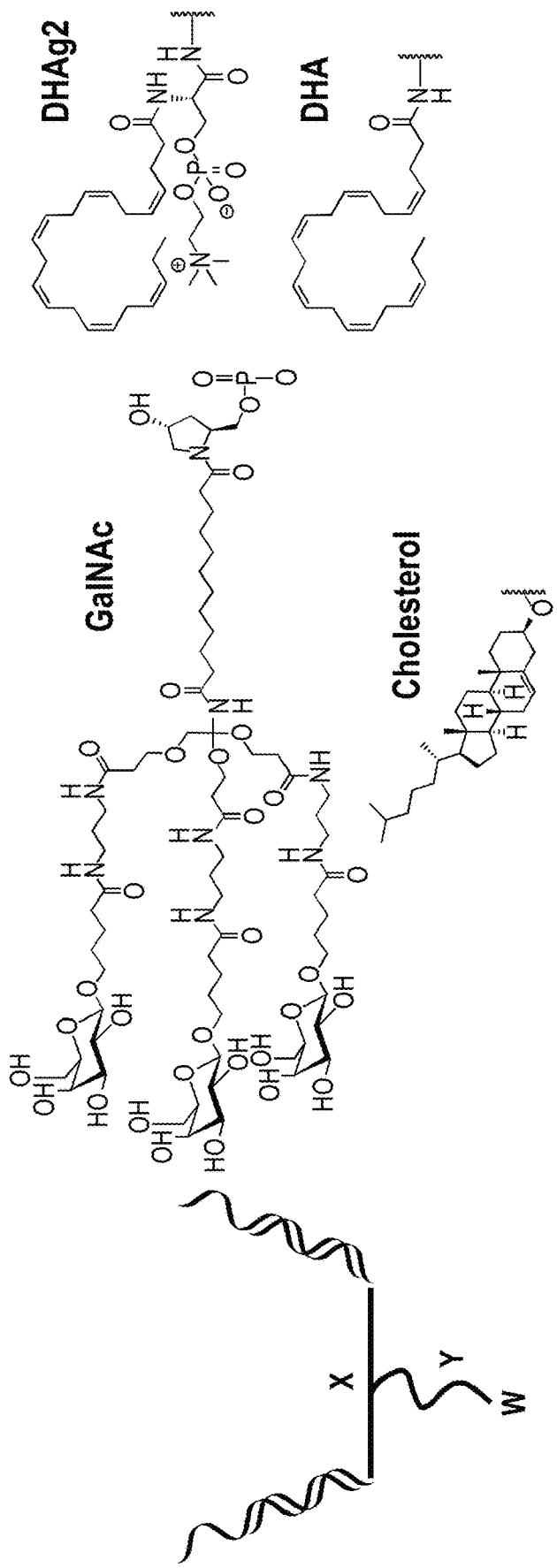
FIG. 16 shows branched oligonucleotides of the invention with conjugated bioactive moieties.
Figure 17:
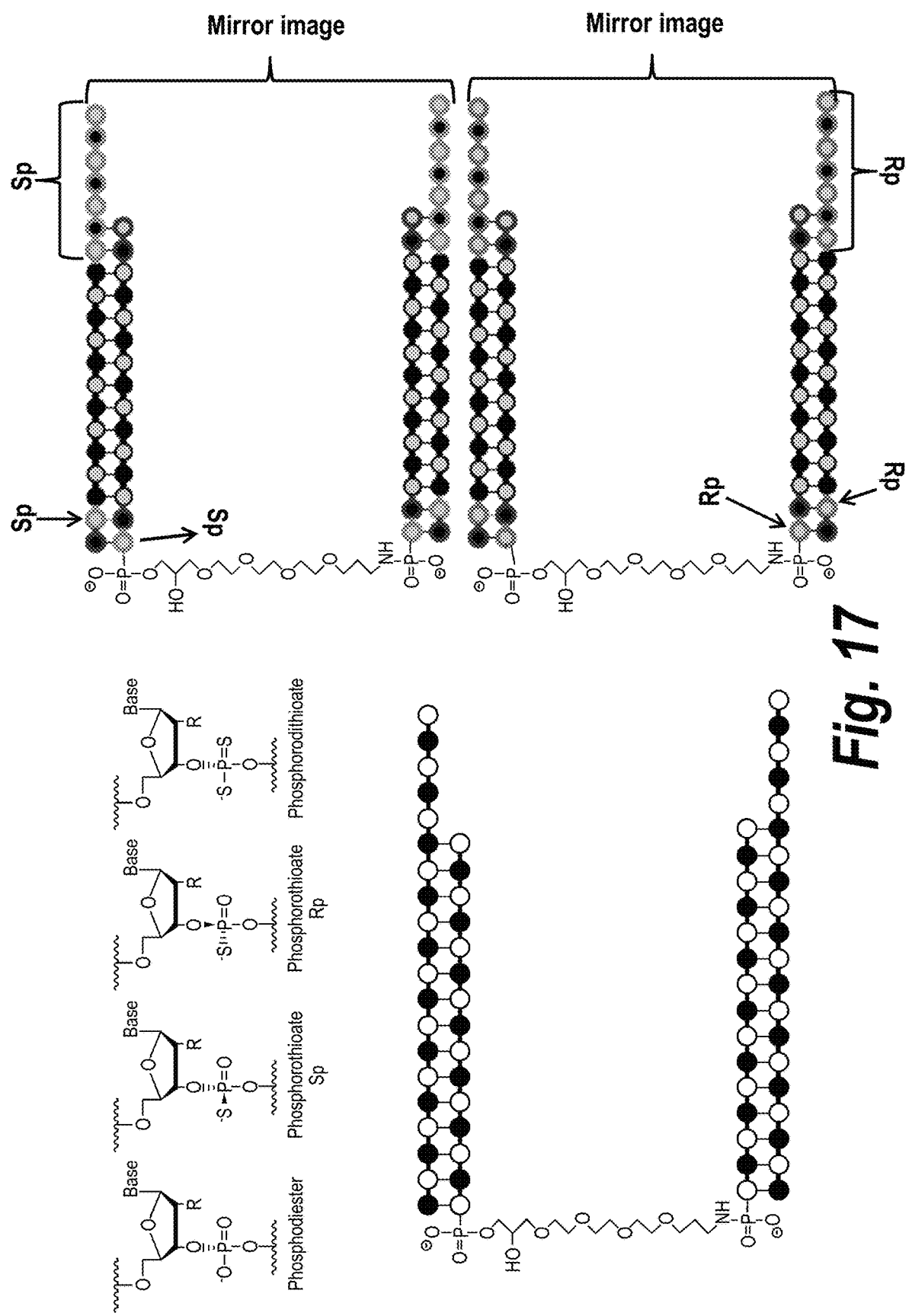
FIG. 17 shows the relationship between phosphorothioate content and stereoselectivity.
Figure 18:
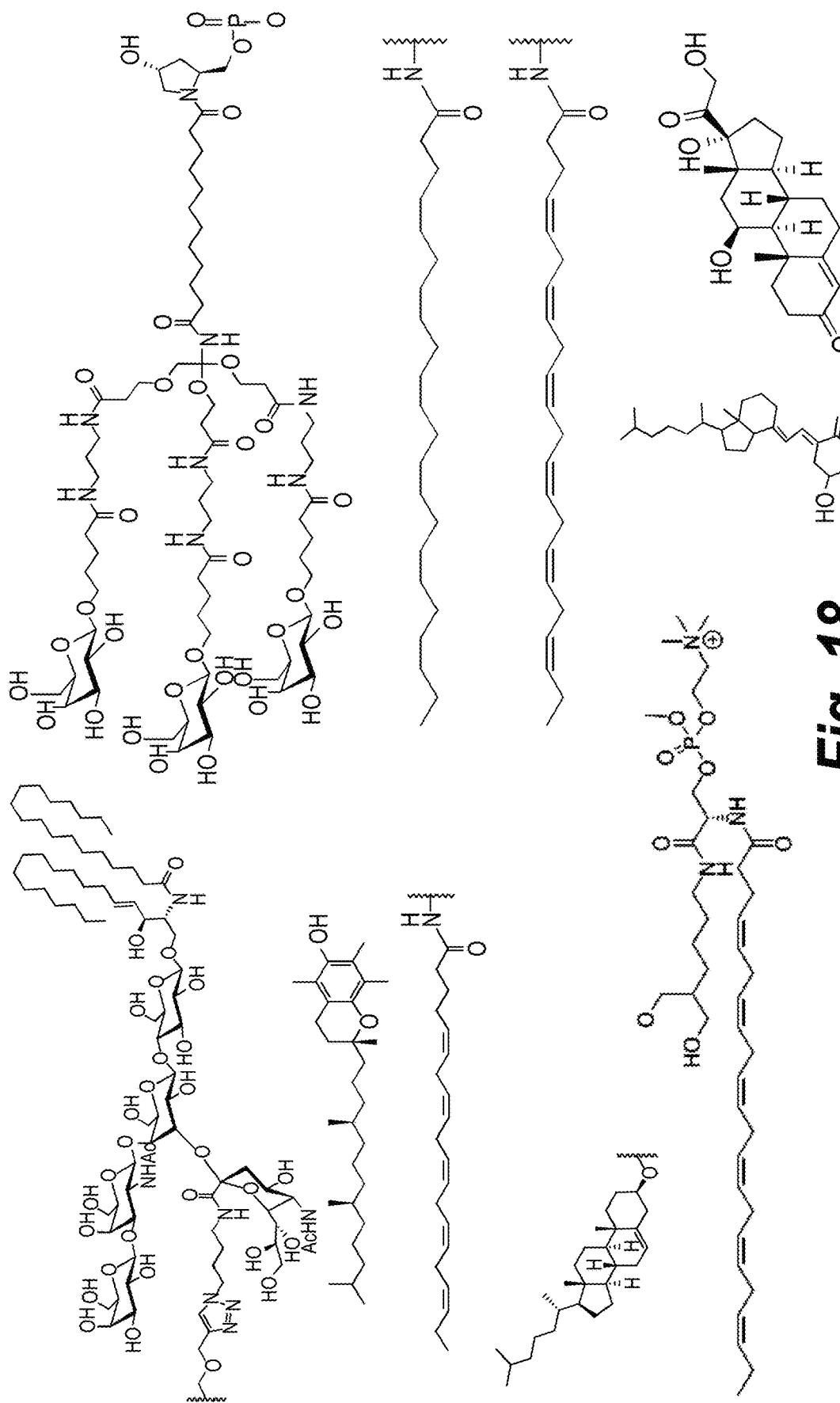
FIG. 18 depicts exemplary hydrophobic moieties.
Figure 19:
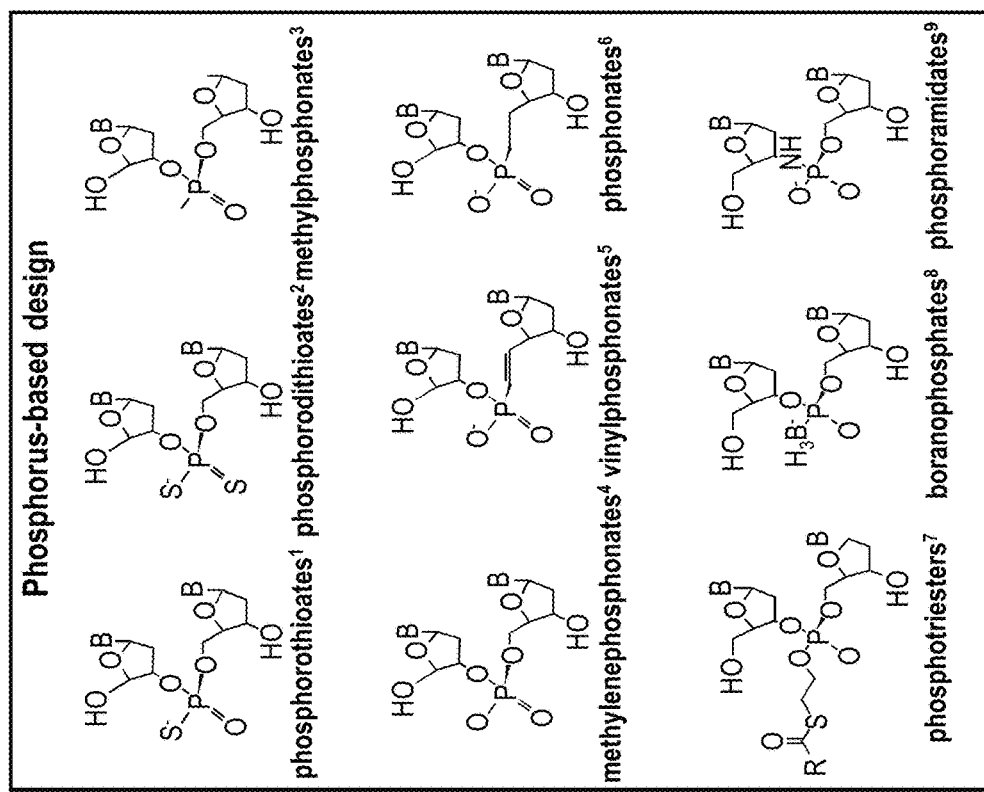
FIG. 19 depicts exemplary internucleotide linkages.
Figure 19:
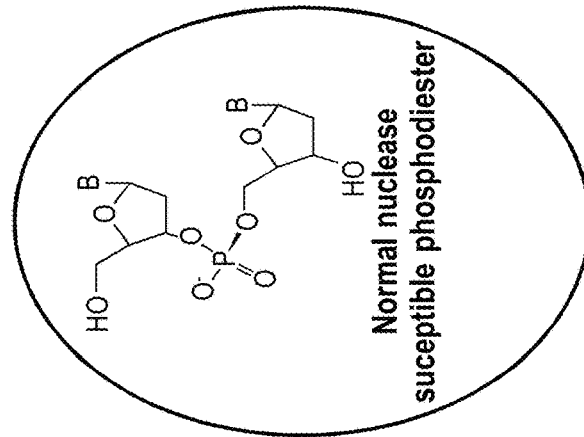
Figure 19:
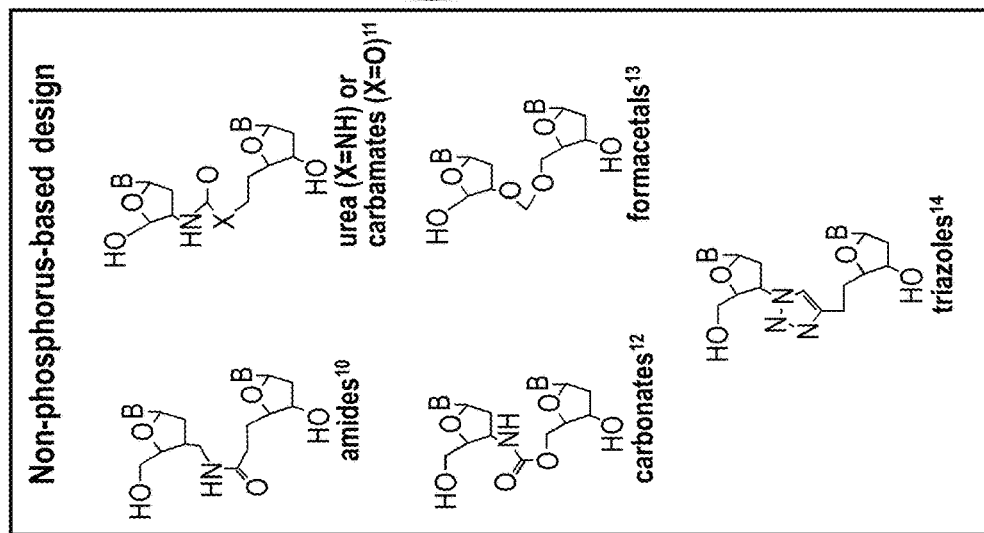
Figure 20:
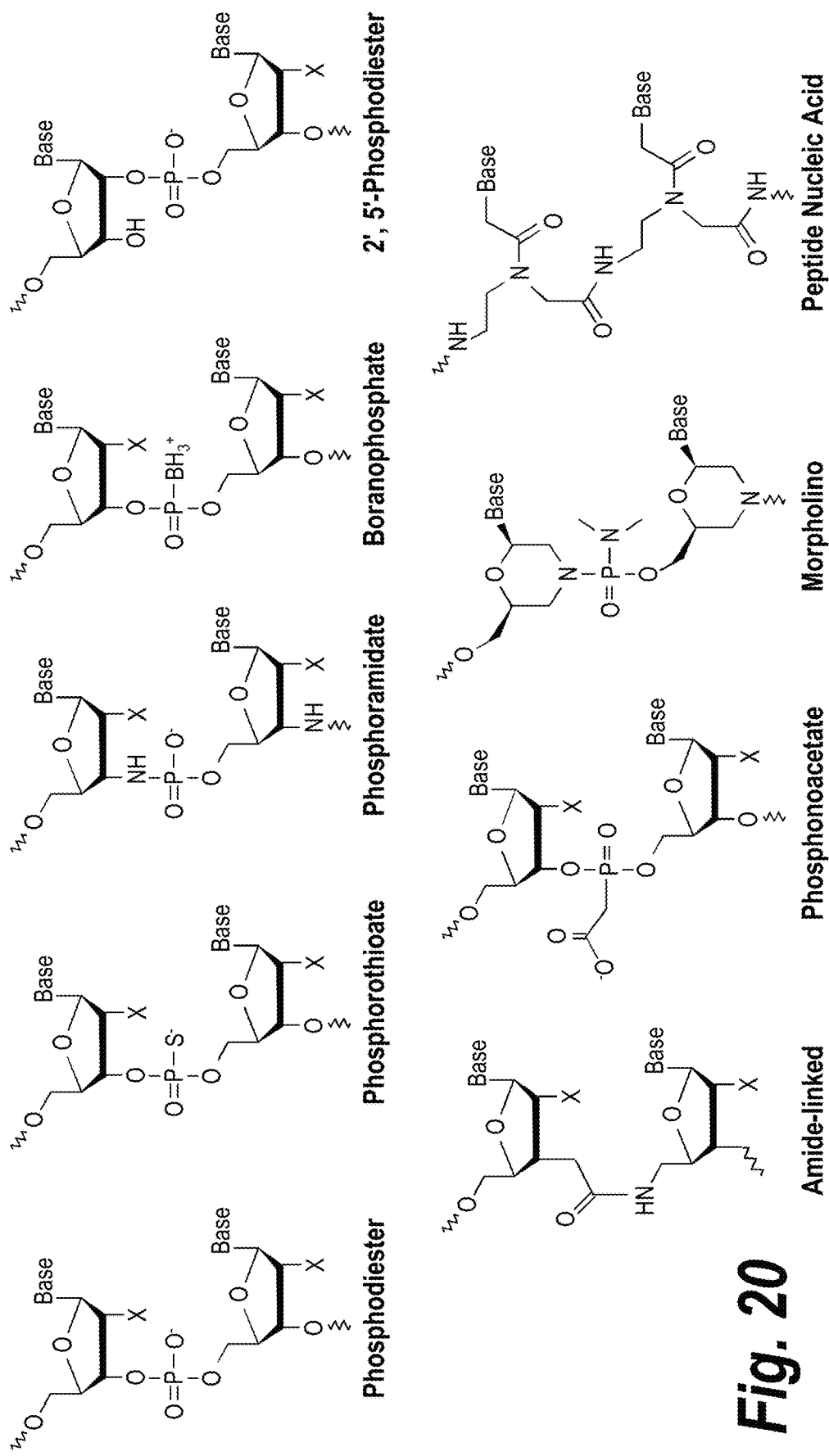
FIG. 20 depicts exemplary internucleotide backbone linkages.
Figure 21:
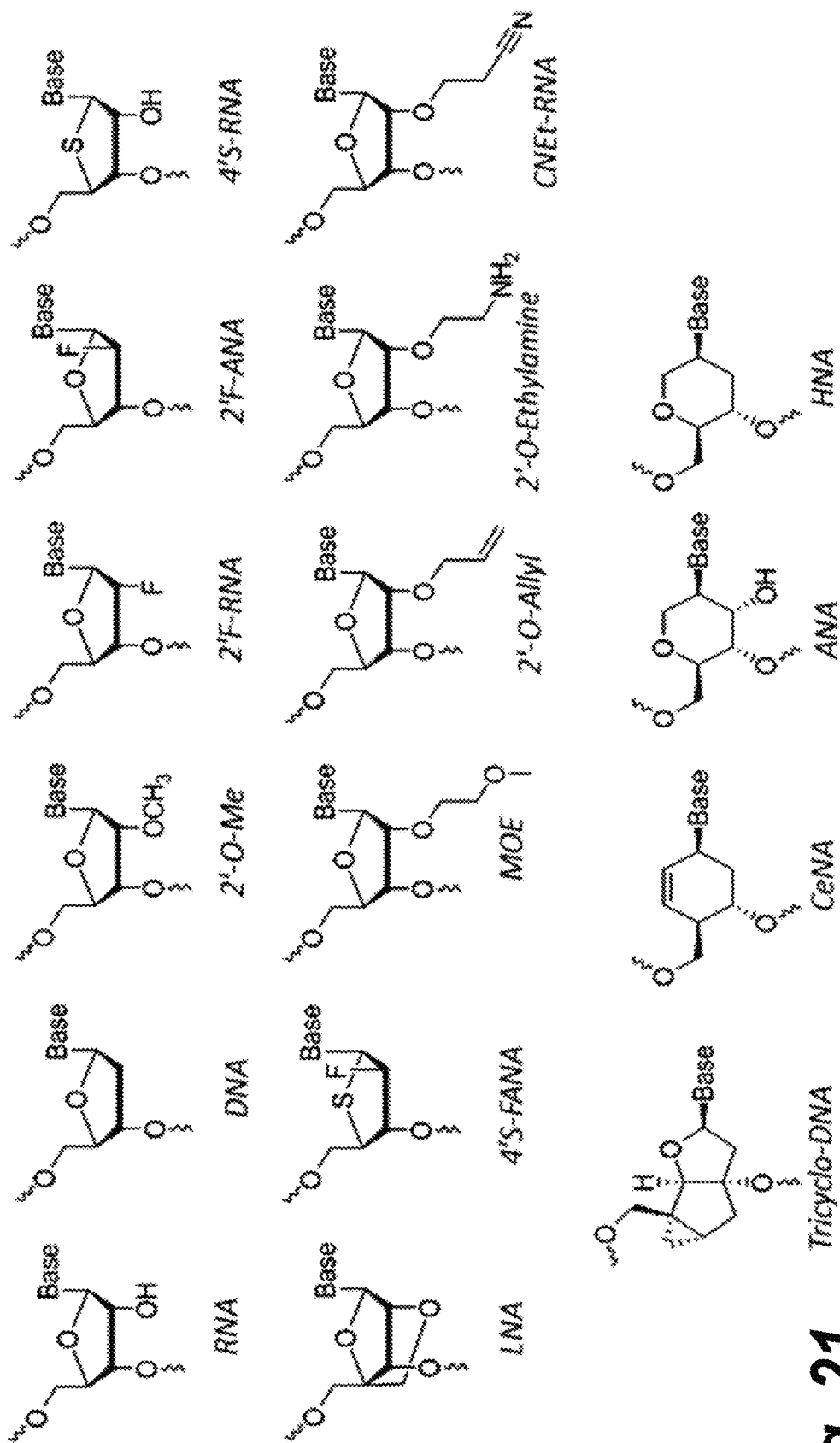
FIG. 21 depicts exemplary sugar modifications.

As shown in FIG. 16, Di-siRNA compounds of the invention may comprise chemically diverse conjugates. Conjugated bioactive ligands may be used to enhance cellular specificity and to promote membrane association, internalization, and serum protein binding. Examples of bioactive moieties to be used for conjugation include DHAg2, DHA, GalNAc, and cholesterol. These moieties can be attached to Di-siRNA either through the connecting linker or spacer, or added via an additional linker or spacer attached to another free siRNA end.

The presence of a branched structure improves the level of tissue retention in the brain more than 100-fold compared to non-branched compounds of identical chemical composition, suggesting a new mechanism of cellular retention and distribution. Compounds of the invention have unexpectedly uniform distribution throughout the spinal cord and brain. Moreover, compounds of the invention exhibit unexpectedly efficient systemic delivery to a variety of tissues, and very high levels of tissue accumulation.

Compounds of the invention comprise a variety of therapeutic oligonucleotides, including ASOs, miRNAs, miRNA inhibitors, splice switching, PMOs, PNAs. In some embodiments, compounds of the invention further comprise conjugated hydrophobic moieties and exhibit unprecedented silencing and efficacy in vitro and in vivo.

Figure 6:
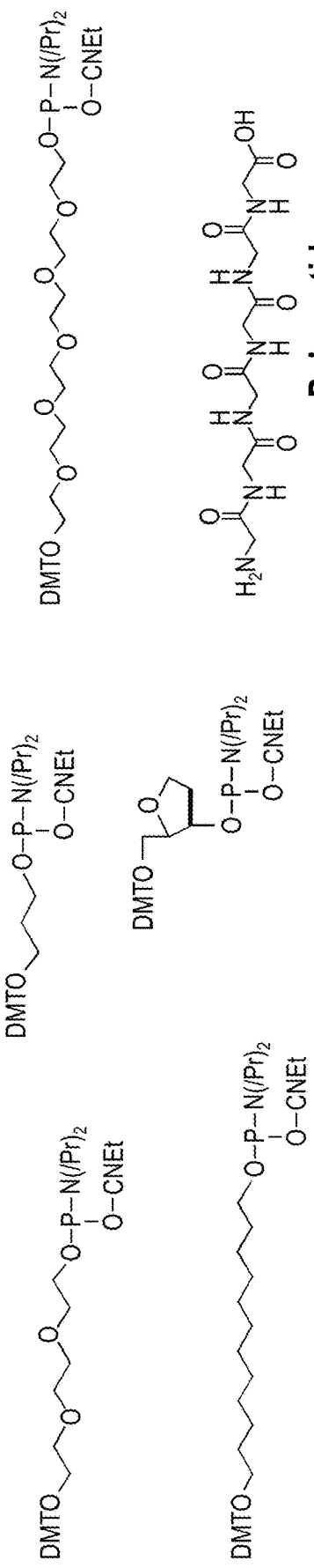
FIG. 6 shows exemplary amidite linkers, spacers and branching moieties.
Figure 6:
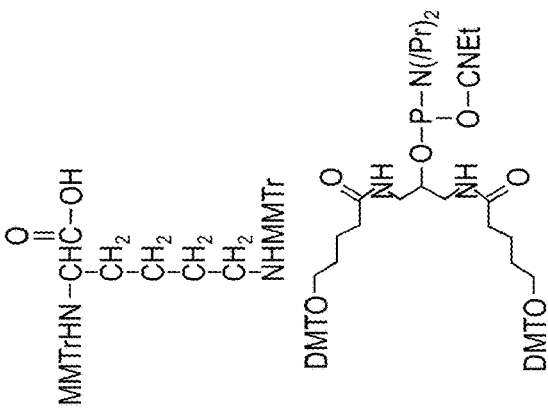
Figure 6:
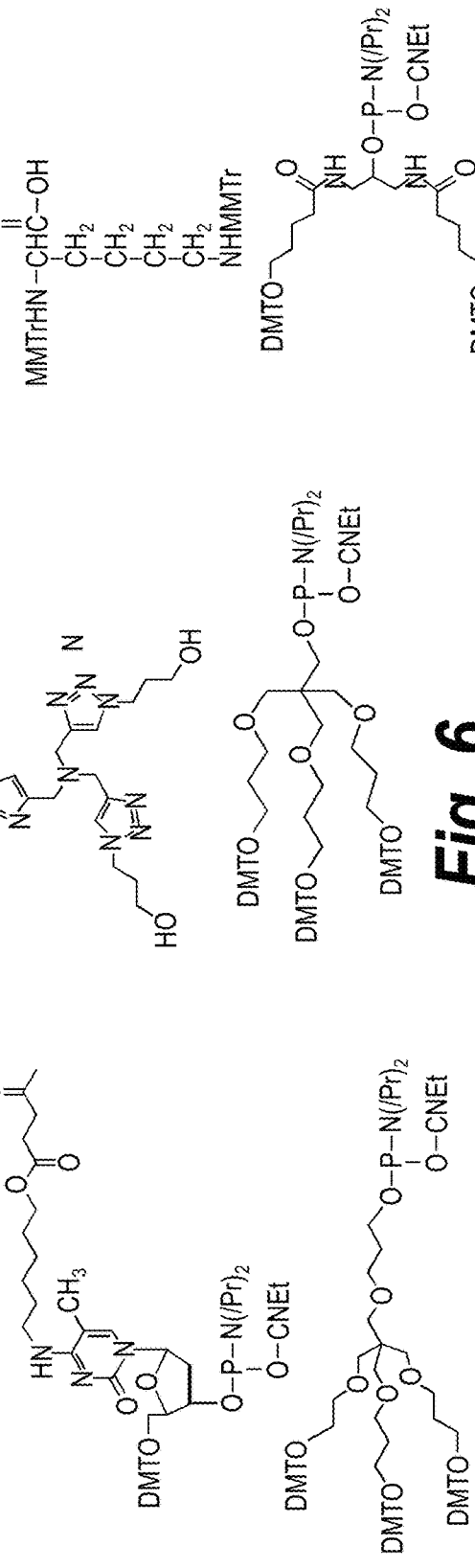

Non-limiting embodiments of branched oligonucleotide configurations are disclosed in FIGS. 1, 7-9, 15-17, and 40-45. Non-limiting examples of linkers, spacers and branching points are disclosed in FIG. 6.

Variable Nucleic Acids

In an embodiment, the branched oligonucleotide comprises 2, 3, 4, 6 or 8 nucleic acids. In one embodiment, the branched oligonucleotide comprises 2 nucleic acids. In another embodiment, the branched oligonucleotide comprises 3 nucleic acids. In another embodiment, the branched oligonucleotide comprises 4 nucleic acids. In another embodiment, the branched oligonucleotide comprises 6 nucleic acids. In another embodiment, the branched oligonucleotide comprises 8 nucleic acids. In another embodiment, the branched oligonucleotide comprises 5 nucleic acids. In another embodiment, the branched oligonucleotide comprises 7 nucleic acids.

In an embodiment of the branched oligonucleotide, each nucleic acid is single-stranded and has a 5' end and a 3' end, and each nucleic acid is independently connected to a linker, a spacer, or a branching point at the 5' end or at the 3' end. In one embodiment, each nucleic acid is connected to a linker, spacer or branching point at the 3' end. In another embodiment, each nucleic acid is connected to a linker, spacer or branching point at the 5' end. In one embodiment, each nucleic acid is connected to a linker. In another embodiment, each nucleic acid is connected to a spacer. In another embodiment, each nucleic acid is connected to a branch point.

In an embodiment, each single-stranded nucleic acid independently comprises at least 15 contiguous nucleotides. In an embodiment, the nucleic acid comprises at least 15, at least 16, at least 17, at least 18, at least 19, or at least 20 contiguous nucleotides, and has complementarity to a target. In certain embodiments, the complementarity is >95%, >90%, >85%, >80%, >75%, >70%, >65%, >60%, >55% or >50%. In one embodiment, the nucleic acid has perfect complementarity to a target.

In an embodiment of the branched oligonucleotide, each nucleic acid is double-stranded and comprises a sense strand and an antisense strand, wherein the sense strand and the antisense strand each have a 5' end and a 3' end. In an embodiment, each double-stranded nucleic acid is independently connected to a linker, spacer or branching point at the 3' end or at the 5' end of the sense strand or the antisense strand. In one embodiment, each nucleic acid is connected to a linker, spacer or branching point at the 3' end of the sense strand. In another embodiment, each nucleic acid is connected to a linker, spacer or branching point at the 3' end of the antisense strand. In another embodiment, each nucleic acid is connected to a linker, spacer or branching point at the 5' end of the sense strand. In another embodiment, each nucleic acid is connected to a linker, spacer or branching point at the 5' end of the antisense strand. In one embodiment, each nucleic acid is connected to a linker. In another embodiment, each nucleic acid is connected to a spacer. In another embodiment, each nucleic acid is connected to a branch point.

In an embodiment, each double-stranded nucleic acid independently comprises at least 15 contiguous nucleotides. In an embodiment, the antisense strand comprises at least 15, at least 16, at least 17, at least 18, at least 19, or at least 20 contiguous nucleotides, and has complementarity to a target. In certain embodiments, the complementarity is >95%, >90%, >85%, >80%, >75%, >70%, >65%, >60%, >55% or >50%. In one embodiment, the antisense strand has perfect complementarity to a target.

Modified Nucleotides

In an embodiment, each nucleic acid comprises one or more chemically-modified nucleotides. In an embodiment, each nucleic acid consists of chemically-modified nucleotides. In certain embodiments, >95%, >90%, >85%, >80%, >75%, >70%, >65%, >60%, >55% or >50% of each nucleic acid comprises chemically-modified nucleotides.

In an embodiment, the sense strand and the antisense strand each comprise one or more chemically-modified nucleotides. In an embodiment, the sense strand and the antisense strand each consist of chemically-modified nucleotides. In an embodiment, the sense strand and the antisense strand both comprise alternating 2'-methoxy-nucleotides and 2'-fluoro-nucleotides. In an embodiment, the nucleotides at positions 1 and 2 from the 5' end of the sense and antisense strands are connected to adjacent nucleotides via phosphorothioate linkages. In an embodiment, the nucleotides at positions 1-6 from the 3' end, or positions 1-7 from the 3' end, are connected to adjacent nucleotides via phosphorothioate linkages. In other embodiments, at least 5 nucleotides are connected to adjacent nucleotides via phosphorothioate linkages.

In an embodiment of the branched oligonucleotide, each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment, each linker is an ethylene glycol chain. In another embodiment, each linker is an alkyl chain. In another embodiment, each linker is a peptide. In another embodiment, each linker is RNA. In another embodiment, each linker is DNA. In another embodiment, each linker is a phosphate. In another embodiment, each linker is a phosphonate. In another embodiment, each linker is a phosphoramidate. In another embodiment, each linker is an ester. In another embodiment, each linker is an amide. In another embodiment, each linker is a triazole. In another embodiment, each linker is a structure selected from the formulas of FIG. 7.

Compound of Formula (I)

In a second aspect, provided herein is a compound of formula (I):

$$L—(N)_n \quad \quad (I)$$

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (I) optionally further comprises one or more branch point B, and one or more spacer S; wherein B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof;

N is an RNA duplex comprising a sense strand and an antisense strand, wherein the sense strand and antisense strand each independently comprise one or more chemical modifications; and n is 2, 3, 4, 5, 6, 7 or 8.

In an embodiment, the compound of formula (I) has a structure selected from formulas (I-1)-(I-9) of Table 1.

TABLE 1

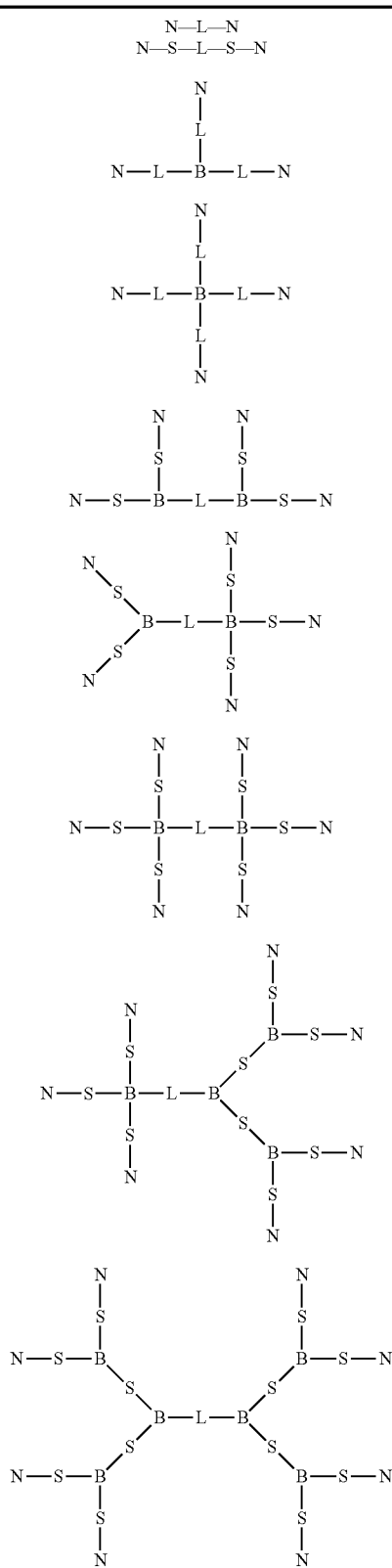

In one embodiment, the compound of formula (I) is formula (I-1). In another embodiment, the compound of formula (I) is formula (I-2). In another embodiment, the compound of formula (I) is formula (I-3). In another embodiment, the compound of formula (I) is formula (I-4). In another embodiment, the compound of formula (I) is formula (I-5). In another embodiment, the compound of formula (I) is formula (I-6). In another embodiment, the compound of formula (I) is formula (I-7). In another embodiment, the compound of formula (I) is formula (I-8). In another embodiment, the compound of formula (I) is formula (I-9).

In an embodiment of the compound of formula (I), each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment of the compound of formula (I), each linker is an ethylene glycol chain. In another embodiment, each linker is an alkyl chain. In another embodiment of the compound of formula (I), each linker is a peptide. In another embodiment of the compound of formula (I), each linker is RNA. In another embodiment of the compound of formula (I), each linker is DNA. In another embodiment of the compound of formula (I), each linker is a phosphate. In another embodiment, each linker is a phosphonate. In another embodiment of the compound of formula (I), each linker is a phosphoramidate. In another embodiment of the compound of formula (I), each linker is an ester. In another embodiment of the compound of formula (I), each linker is an amide. In another embodiment of the compound of formula (I), each linker is a triazole. In another embodiment of the compound of formula (I), each linker is a structure selected from the formulas of FIG. 7.

In one embodiment of the compound of formula (I), B is a polyvalent organic species. In another embodiment of the compound of formula (I), B is a derivative of a polyvalent organic species. In one embodiment of the compound of formula (I), B is a triol or tetrol derivative. In another embodiment, B is a tri- or tetra-carboxylic acid derivative. In another embodiment, B is an amine derivative. In another embodiment, B is a tri- or tetra-amine derivative. In another embodiment, B is an amino acid derivative. In another embodiment of the compound of formula (I), B is selected from the formulas of FIG. 6.

Polyvalent organic species are moieties comprising carbon and three or more valencies (i.e., points of attachment with moieties such as S, L or N, as defined above). Non-limiting examples of polyvalent organic species include triols (e.g., glycerol, phloroglucinol, and the like), tetrols (e.g., ribose, pentaerythritol, 1,2,3,5-tetrahydroxybenzene, and the like), tri-carboxylic acids (e.g., citric acid, 1,3,5-cyclohexanetricarboxylic acid, trimesic acid, and the like), tetra-carboxylic acids (e.g., ethylenediaminetetraacetic acid, pyromellitic acid, and the like), tertiary amines (e.g., tripropargylamine, triethanolamine, and the like), triamines (e.g., diethylenetriamine and the like), tetramines, and species comprising a combination of hydroxyl, thiol, amino, and/or carboxyl moieties (e.g., amino acids such as lysine, serine, cysteine, and the like).

In an embodiment of the compound of formula (I), each nucleic acid comprises one or more chemically-modified nucleotides. In an embodiment of the compound of formula (I), each nucleic acid consists of chemically-modified nucleotides. In certain embodiments of the compound of formula (I), >95%, >90%, >85%, >80%, >75%, >70%, >65%, >60%, >55% or >50% of each nucleic acid comprises chemically-modified nucleotides.

In an embodiment, each antisense strand independently comprises a 5' terminal group R selected from the groups of Table 2.

TABLE 2

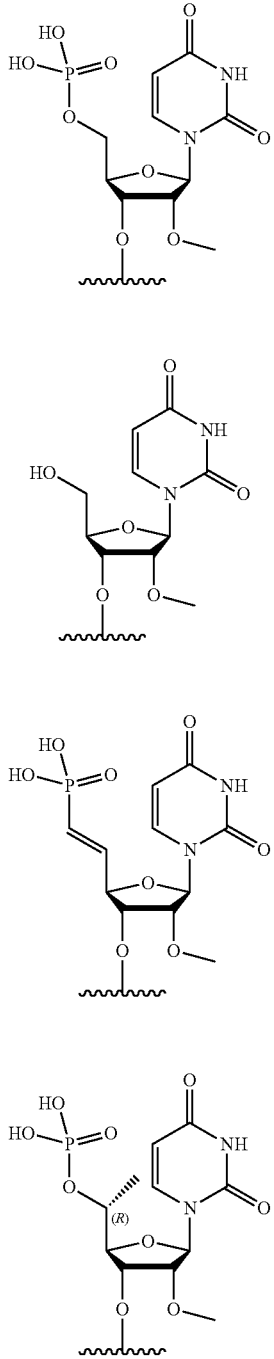

TABLE 2-continued

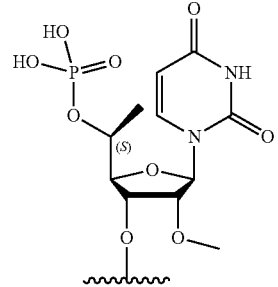

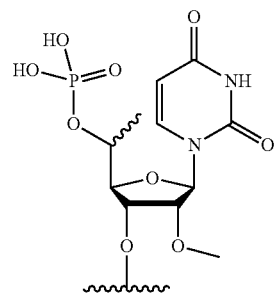

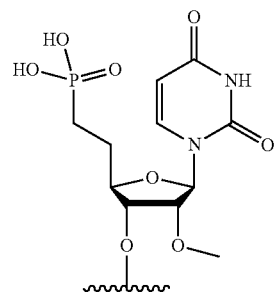

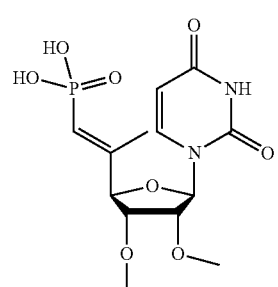

In one embodiment, R is $R_1$. In another embodiment, R is $R_2$. In another embodiment, R is $R_3$. In another embodiment, R is $R_4$. In another embodiment, R is $R_5$. In another embodiment, R is $R_6$. In another embodiment, R is $R_7$. In another embodiment, R is $R_8$.

Structure of Formula (II)

In an embodiment, the compound of formula (I) the structure of formula (II):

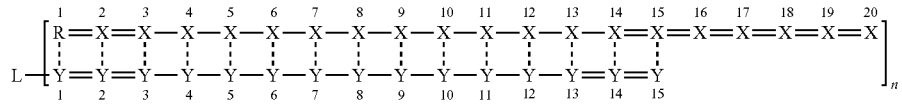

(II)

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; — represents a phosphodiester internucleoside linkage; = represents a phosphorothioate internucleoside linkage; and ≡ represents, individually for each occurrence, a base-pairing interaction or a mismatch.

In certain embodiments, the structure of formula (II) does not contain mismatches. In one embodiment, the structure of formula (II) contains 1 mismatch. In another embodiment, the compound of formula (II) contains 2 mismatches. In another embodiment, the compound of formula (II) contains 3 mismatches. In another embodiment, the compound of formula (II) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of formula (II) are chemically-modified nucleotides. In other embodiments, >95%, >90%, >85%, >80%, >75%, >70%, >65%, >60%, >55% or >50% of X's of the structure of formula (II) are chemically-modified nucleotides.

Structure of Formula (III)

In an embodiment, the compound of formula (I) has the structure of formula (III):

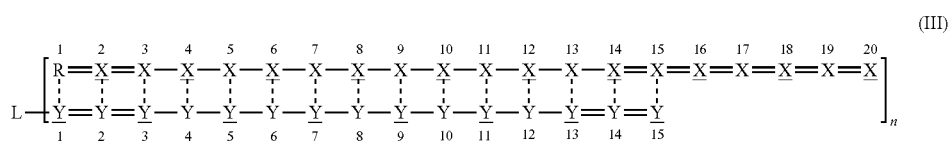

(III)

wherein $\underline{X}$, for each occurrence, independently, is a nucleotide comprising a 2'-deoxy-2'-fluoro modification; X, for each occurrence, independently, is a nucleotide comprising a 2'-O-methyl modification; $\underline{Y}$, for each occurrence, independently, is a nucleotide comprising a 2'-deoxy-2'-fluoro modification; and Y, for each occurrence, independently, is a nucleotide comprising a 2'-O-methyl modification.

In an embodiment, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of formula (III) does not contain mismatches. In one embodiment, the structure of formula (III) contains 1 mismatch. In another embodiment, the compound of formula (III) contains 2 mismatches. In another embodiment, the compound of formula (III) contains 3 mismatches. In another embodiment, the compound of formula (III) contains 4 mismatches.

Structure of Formula (IV)

In an embodiment, the compound of formula (I) has the structure of formula (IV) (SEQ ID NOS 1 and 2, respectively, in order of appearance):

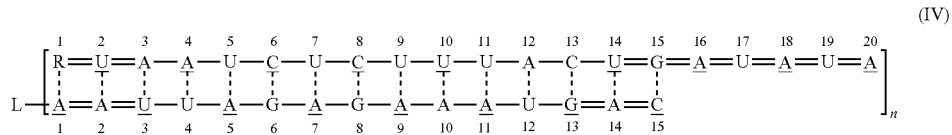

(IV)

wherein $\underline{A}$ is an adenosine comprising a 2'-deoxy-2'-fluoro modification; A is an adenosine comprising a 2'-O-methyl modification; $\underline{G}$ is an guanosine comprising a 2'-deoxy-2'-fluoro modification; G is an guanosine comprising a 2'-O-methyl modification; U is an uridine comprising a 2'-deoxy-2'-fluoro modification; $\underline{U}$ is an uridine comprising a 2'-O-methyl modification; $\underline{C}$ is an cytidine comprising a 2'-deoxy-2'-fluoro modification; and C is an cytidine comprising a 2'-O-methyl modification.

Structure of Formula (V)

In an embodiment, the compound of formula (I) has the structure of formula (V):

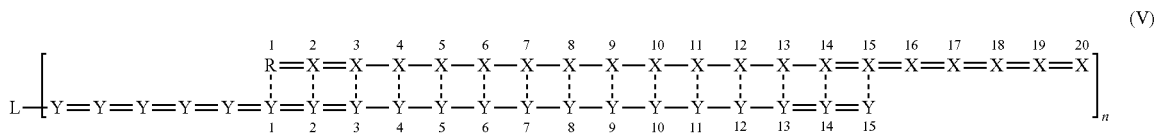

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; — represents a phosphodiester internucleoside linkage; ═ represents a phosphorothioate internucleoside linkage; and ≡ represents, individually for each occurrence, a base-pairing interaction or a mismatch.

In certain embodiments, the structure of formula (V) does not contain mismatches. In one embodiment, the structure of formula (V) contains 1 mismatch. In another embodiment, the compound of formula (V) contains 2 mismatches. In another embodiment, the compound of formula (V) contains 3 mismatches. In another embodiment, the compound of formula (V) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of formula (II) are chemically-modified nucleotides. In other embodiments, >95%, >90%, >85%, >80%, >75%, >70%, >65%, >60%, >55% or >50% of X's of the structure of formula (II) are chemically-modified nucleotides.

Structure of Formula (VI)

In an embodiment, the compound of formula (I) has the structure of formula (VI):

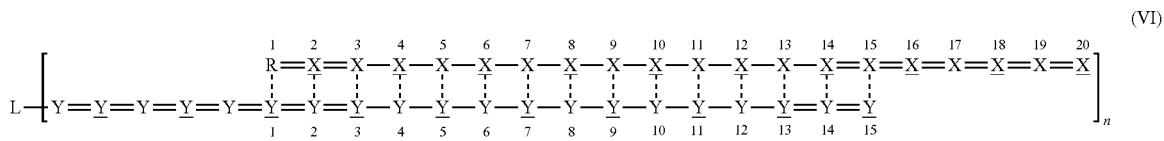

wherein X̲, for each occurrence, independently, is a nucleotide comprising a 2'-deoxy-2'-fluoro modification; X, for each occurrence, independently, is a nucleotide comprising a 2'-O-methyl modification; Y̲, for each occurrence, independently, is a nucleotide comprising a 2'-deoxy-2'-fluoro modification; and Y, for each occurrence, independently, is a nucleotide comprising a 2'-O-methyl modification.

In certain embodiments, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of formula (VI) does not contain mismatches. In one embodiment, the structure of formula (VI) contains 1 mismatch. In another embodiment, the compound of formula (VI) contains 2 mismatches. In another embodiment, the compound of formula (VI) contains 3 mismatches. In another embodiment, the compound of formula (VI) contains 4 mismatches.

Structure of Formula (VII)

In an embodiment, the compound of formula (I) has the structure of formula (VII) (SEQ ID NOS 3 and 4, respectively, in order of appearance):

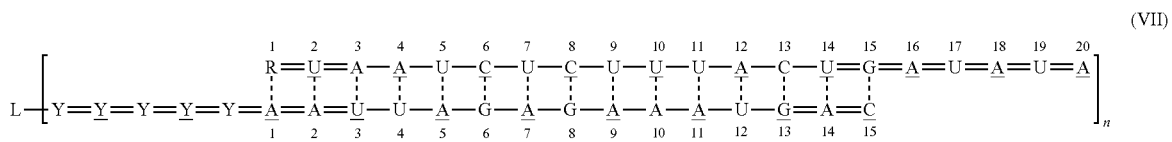

wherein A̲ is an adenosine comprising a 2'-deoxy-2'-fluoro modification; A is an adenosine comprising a 2'-O-methyl modification; G̲ is an guanosine comprising a 2'-deoxy-2'-fluoro modification; G is an guanosine comprising a 2'-O-methyl modification; U̲ is an uridine comprising a 2'-deoxy-2'-fluoro modification; U is an uridine comprising a 2'-O-methyl modification; C̲ is an cytidine comprising a 2'-deoxy-2'-fluoro modification; C is an cytidine comprising a 2'-O-methyl modification; Y̲, for each occurrence, independently, is a nucleotide comprising a 2'-deoxy-2'-fluoro modification; and Y, for each occurrence, independently, is a nucleotide comprising a 2'-O-methyl modification.

Variable Linkers

In an embodiment of the compound of formula (I), L has the structure of L1:

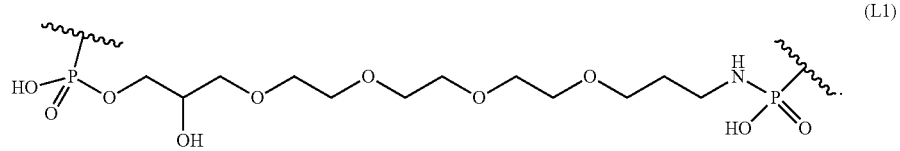 [SMILES: *P(=O)(O)NCCCOCCOCCOCCOCC(O)COP(*)(=O)O]

(L1)

In an embodiment of L1, R is $R^3$ and n is 2.

In an embodiment of the structure of formula (II), L has the structure of L1. In an embodiment of the structure of formula (III), L has the structure of L1. In an embodiment of the structure of formula (IV), L has the structure of L1. In an embodiment of the structure of formula (V), L has the structure of L1. In an embodiment of the structure of formula (VI), L has the structure of L1. In an embodiment of the structure of formula (VII), L has the structure of L1.

In an embodiment of the compound of formula (I), L has the structure of L2:

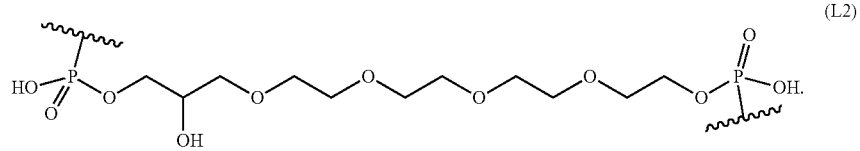 [SMILES: *P(=O)(O)OCCOCCOCCOCCOCC(O)COP(*)(=O)O]

(L2)

In an embodiment of L2, R is $R^3$ and n is 2.

In an embodiment of the structure of formula (II), L has the structure of L2. In an embodiment of the structure of formula (III), L has the structure of L2. In an embodiment of the structure of formula (IV), L has the structure of L2. In an embodiment of the structure of formula (V), L has the structure of L2. In an embodiment of the structure of formula (VI), L has the structure of L2. In an embodiment of the structure of formula (VII), L has the structure of L2.

Delivery System

In a third aspect, provided herein is a delivery system for therapeutic nucleic acids having the structure of formula (VIII):

L—(cNA)$_n$     (VIII)

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (VIII) optionally further comprises one or more branch point B, and one or more spacer S; wherein B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof; each cNA, independently, is a carrier nucleic acid comprising one or more chemical modifications; and n is 2, 3, 4, 5, 6, 7 or 8.

In one embodiment of the delivery system, L is an ethylene glycol chain. In another embodiment of the delivery system, L is an alkyl chain. In another embodiment of the delivery system, L is a peptide. In another embodiment of the delivery system, L is RNA. In another embodiment of the delivery system, L is DNA. In another embodiment of the delivery system, L is a phosphate. In another embodiment of the delivery system, L is a phosphonate. In another embodiment of the delivery system, L is a phosphoramidate. In another embodiment of the delivery system, L is an ester. In another embodiment of the delivery system, L is an amide. In another embodiment of the delivery system, L is a triazole.

In one embodiment of the delivery system, S is an ethylene glycol chain. In another embodiment, S is an alkyl chain. In another embodiment of the delivery system, S is a peptide. In another embodiment, S is RNA. In another embodiment of the delivery system, S is DNA. In another embodiment of the delivery system, S is a phosphate. In another embodiment of the delivery system, S is a phosphonate. In another embodiment of the delivery system, S is a phosphoramidate. In another embodiment of the delivery system, S is an ester. In another embodiment, S is an amide. In another embodiment, S is a triazole.

In one embodiment of the delivery system, n is 2. In another embodiment of the delivery system, n is 3. In another embodiment of the delivery system, n is 4. In another embodiment of the delivery system, n is 5. In another embodiment of the delivery system, n is 6. In another embodiment of the delivery system, n is 7. In another embodiment of the delivery system, n is 8.

In certain embodiments, each cNA comprises >95%, >90%, >85%, >80%, >75%, >70%, >65%, >60%, >55% or >50% chemically-modified nucleotides.

In an embodiment, the compound of formula (VIII) has a structure selected from formulas (VIII-1)-(VIII-9) of Table 3:

TABLE 3

ANc—L—cNA     (VIII-1)

ANc—S—L—S—cNA     (VIII-2)

```
         cNA
          |
          L
          |
ANc—L—B—L—cNA                    (VIII-3)
```

```
         cNA
          |
          L
          |
ANc—L—B—L—cNA
          |
          L
          |
         cNA                      (VIII-4)
```

```
    cNA         cNA
     |           |
     S           S
     |           |
ANc—S—B—L—B—S—cNA                (VIII-5)
```

```
              cNA
               |
  ANc          S
     \         |
      S   B—L—B—S—cNA             (VIII-6)
     / 
  ANc          S
               |
              cNA
```

```
    cNA         cNA
     |           |
     S           S
     |           |
ANc—S—B—L—B—S—cNA                (VIII-7)
     |           |
     S           S
     |           |
    cNA         cNA
```

```
                cNA
                 |
    cNA          S
     |           |
     S        B—S—cNA
     |       /
ANc—S—B—L—B
     |       \
     S        B—S—cNA
     |           |
    cNA          S
                 |
                cNA              (VIII-8)
```

```
   ANc              cNA
    |                |
    S                S
    |                |
ANc—S—B          B—S—cNA
       \        /
        S      S
         \    /
          B—L—B
         /    \
        S      S
       /        \
ANc—S—B          B—S—cNA
    |                |
    S                S
    |                |
   cNA              cNA          (VIII-9)
```

In an embodiment, the compound of formula (VIII) is the structure of formula (VIII-1). In an embodiment, the compound of formula (VIII) is the structure of formula (VIII-2). In an embodiment, the compound of formula (VIII) is the structure of formula (VIII-3). In an embodiment, the compound of formula (VIII) is the structure of formula (VIII-4). In an embodiment, the compound of formula (VIII) is the structure of formula (VIII-5). In an embodiment, the compound of formula (VIII) is the structure of formula (VIII-6). In an embodiment, the compound of formula (VIII) is the structure of formula (VIII-7). In an embodiment, the compound of formula (VIII) is the structure of formula (VIII-8). In an embodiment, the compound of formula (VIII) is the structure of formula (VIII-9).

In an embodiment, the compound of formulas (VIII) (including, e.g., formulas (VIII-1)-(VIII-9), each cNA independently comprises at least 15 contiguous nucleotides. In an embodiment, each cNA independently consists of chemically-modified nucleotides.

In an embodiment, the delivery system further comprises n therapeutic nucleic acids (NA), wherein each NA is hybridized to at least one cNA. In one embodiment, the delivery system is comprised of 2 NAs. In another embodiment, the delivery system is comprised of 3 NAs. In another embodiment, the delivery system is comprised of 4 NAs. In another embodiment, the delivery system is comprised of 5 NAs. In another embodiment, the delivery system is comprised of 6 NAs. In another embodiment, the delivery system is comprised of 7 NAs. In another embodiment, the delivery system is comprised of 8 NAs.

In an embodiment, each NA independently comprises at least 16 contiguous nucleotides. In an embodiment, each NA independently comprises 16-20 contiguous nucleotides. In an embodiment, each NA independently comprises 16 contiguous nucleotides. In another embodiment, each NA independently comprises 17 contiguous nucleotides. In another embodiment, each NA independently comprises 18 contiguous nucleotides. In another embodiment, each NA independently comprises 19 contiguous nucleotides. In another embodiment, each NA independently comprises 20 contiguous nucleotides.

In an embodiment, each NA comprises an unpaired overhang of at least 2 nucleotides. In another embodiment, each NA comprises an unpaired overhang of at least 3 nucleotides. In another embodiment, each NA comprises an unpaired overhang of at least 4 nucleotides. In another embodiment, each NA comprises an unpaired overhang of at least 5 nucleotides. In another embodiment, each NA comprises an unpaired overhang of at least 6 nucleotides. In an embodiment, the nucleotides of the overhang are connected via phosphorothioate linkages.

In an embodiment, each NA, independently, is selected from the group consisting of: DNA, siRNAs, antagomiRs, miRNAs, gapmers, mixmers, or guide RNAs. In one embodiment, each NA, independently, is a DNA. In another embodiment, each NA, independently, is a siRNA. In another embodiment, each NA, independently, is an antagomiR. In another embodiment, each NA, independently, is a miRNA. In another embodiment, each NA, independently, is a gapmer. In another embodiment, each NA, independently, is a mixmer. In another embodiment, each NA, independently, is a guide RNA. In an embodiment, each NA is the same. In an embodiment, each NA is not the same.

In an embodiment, the delivery system further comprising n therapeutic nucleic acids (NA) has a structure selected from formulas (I), (II), (III), (IV), (V), (VI), (VII), and embodiments thereof described herein. In one embodiment, the delivery system has a structure selected from formulas (I), (II), (III), (IV), (V), (VI), (VII), and embodiments thereof described herein further comprising 2 therapeutic nucleic acids (NA). In another embodiment, the delivery system has a structure selected from formulas (I), (II), (III), (IV), (V), (VI), (VII), and embodiments thereof described herein further comprising 3 therapeutic nucleic acids (NA). In one embodiment, the delivery system has a structure selected from formulas (I), (II), (III), (IV), (V), (VI), (VII), and embodiments thereof described herein further comprising 4 therapeutic nucleic acids (NA). In one embodiment, the delivery system has a structure selected from formulas (I), (II), (III), (IV), (V), (VI), (VII), and embodiments thereof described herein further comprising 5 therapeutic nucleic acids (NA). In one embodiment, the delivery system has a structure selected from formulas (I), (II), (III), (IV), (V), (VI), (VII), and embodiments thereof described herein further comprising 6 therapeutic nucleic acids (NA). In one embodiment, the delivery system has a structure selected from formulas (I), (II), (III), (IV), (V), (VI), (VII), and embodiments thereof described herein further comprising 7 therapeutic nucleic acids (NA). In one embodiment, the delivery system has a structure selected from formulas (I), (II), (III), (IV), (V), (VI), (VII), and embodiments thereof described herein further comprising 8 therapeutic nucleic acids (NA).

In one embodiment, the delivery system has a structure selected from formulas (I), (II), (III), (IV), (V), (VI), (VII) further comprising a linker of structure L1 or L2 wherein R is $R^3$ and n is 2. In another embodiment, the delivery system has a structure selected from formulas (I), (II), (III), (IV), (V), (VI), (VII) further comprising a linker of structure L1 wherein R is $R^3$ and n is 2. In another embodiment, the delivery system has a structure selected from formulas (I), (II), (III), (IV), (V), (VI), (VII) further comprising a linker of structure L2 wherein R is $R^3$ and n is 2.

In an embodiment of the delivery system, the target of delivery is selected from the group consisting of: brain, liver, skin, kidney, spleen, pancreas, colon, fat, lung, muscle, and thymus. In one embodiment, the target of delivery is the brain. In another embodiment, the target of delivery is the striatum of the brain. In another embodiment, the target of delivery is the cortex of the brain. In another embodiment, the target of delivery is the striatum of the brain. In one embodiment, the target of delivery is the liver. In one embodiment, the target of delivery is the skin. In one embodiment, the target of delivery is the kidney. In one embodiment, the target of delivery is the spleen. In one embodiment, the target of delivery is the pancreas. In one embodiment, the target of delivery is the colon. In one embodiment, the target of delivery is the fat. In one embodiment, the target of delivery is the lung. In one embodiment, the target of delivery is the muscle. In one embodiment, the target of delivery is the thymus. In one embodiment, the target of delivery is the spinal cord.

It is to be understood that the methods described in this disclosure are not limited to particular methods and experimental conditions disclosed herein; as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY (1987-2008), including all supplements, Molecular Cloning: A Laboratory Manual (Fourth Edition) by M R Green and J. Sambrook and Harlow et al., Antibodies: A Laboratory Manual, Chapter 14, Cold Spring Harbor Laboratory, Cold Spring Harbor (2013, 2nd edition).

Definitions

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

As used herein, the term "nucleic acids" refers to RNA or DNA molecules consisting of a chain of ribonucleotides or deoxyribonucleotides, respectively.

As used herein, the term "therapeutic nucleic acid" refers to a nucleic acid molecule (e.g., ribonucleic acid) that has partial or complete complementarity to, and interacts with, a disease-associated target mRNA and mediates silencing of expression of the mRNA.

As used herein, the term "carrier nucleic acid" refers to a nucleic acid molecule (e.g., ribonucleic acid) that has sequence complementarity with, and hybridizes with, a therapeutic nucleic acid.

As used herein, the term "3' end" refers to the end of the nucleic acid that contains an unmodified hydroxyl group at the 3' carbon of the ribose ring.

As used herein, the term "5' end" refers to the end of the nucleic acid that contains a phosphate group attached to the 5' carbon of the ribose ring.

As used herein, the term "nucleoside" refers to a molecule made up of a heterocyclic base and its sugar.

As used herein, the term "nucleotide" refers to a nucleoside having a phosphate group on its 3' or 5' sugar hydroxyl group.

As used herein, the term "siRNA" refers to small interfering RNA duplexes that induce the RNA interference (RNAi) pathway. siRNA molecules can vary in length (generally between 18-30 basepairs) and contain varying degrees of complementarity to their target mRNA. The term "siRNA" includes duplexes of two separate strands, as well as single strands that can form hairpin structures comprising a duplex region.

As used herein, the term "antisense strand" refers to the strand of the siRNA duplex that contains some degree of complementarity to the target gene.

As used herein, the term "sense strand" refers to the strand of the siRNA duplex that contains complementarity to the antisense strand.

As used herein, the terms "chemically modified nucleotide" or "nucleotide analog" or "altered nucleotide" or "modified nucleotide" refer to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, NH2, NHR, NR$_2$, COOR, or OR, wherein R is substituted or unsubstituted C1-C6 alkyl, alkenyl, alkynyl, aryl, etc. Other possible modifications include those described in U.S. Pat. Nos. 5,858,988, and 6,291,438.

As used herein, the term "metabolically stabilized" refers to RNA molecules that contain ribonucleotides that have been chemically modified from 2'-hydroxyl groups to 2'-O-methyl groups.

As used herein, the term "phosphorothioate" refers to the phosphate group of a nucleotide that is modified by substituting one or more of the oxygens of the phosphate group with sulfur.

As used herein, the term "ethylene glycol chain" refers to a carbon chain with the formula $((CH_2OH)_2)$.

As used herein, the term "alkyl chain" refers to an acyclic unsaturated hydrocarbon chain. In connection with this invention an "alkyl chain" includes but is not limited to straight chain, branch chain, and cyclic unsaturated hydrocarbon groups.

As used herein, the term "amide" refers to an alkyl or aromatic group that is attached to an amino-carbonyl functional group.

As used herein, the term "internucleoside" and "internucleotide" refer to the bonds between nucleosides and nucleotides, respectively.

As used herein, the term "triazol" refers to heterocyclic compounds with the formula $(C_2H_3N_3)$, having a five-membered ring of two carbons and three nitrogens, the positions of which can change resulting in multiple isomers.

As used herein, the term "terminal group" refers to the group at which a carbon chain or nucleic acid ends.

As used herein, the term "lipophilic amino acid" refers to an amino acid comprising a hydrophobic moiety (e.g., an alkyl chain or an aromatic ring).

As used herein, the term "antagomiRs" refers to nucleic acids that can function as inhibitors of miRNA activity.

As used herein, the term "gapmers" refers to chimeric antisense nucleic acids that contain a central block of deoxynucleotide monomers sufficiently long to induce RNase H cleavage. The deoxynucleotide block is flanked by ribonucleotide monomers or ribonucleotide monomers containing modifications.

As used herein, the term "mixmers" refers to nucleic acids that are comprised of a mix of locked nucleic acids (LNAs) and DNA.

As used herein, the term "guide RNAs" refers to refers to nucleic acids that have sequence complementarity to a specific sequence in the genome immediately or 1 base pair upstream of the protospacer adjacent motif (PAM) sequence as used in CRISPR/Cas9 gene editing systems.

As used herein, the term "target of delivery" refers to the organ or part of the body that is desired to deliver the branched oligonucleotide compositions to.

As used herein, the term "Di-siRNA" refers to a molecule of the present invention that comprises a branched oligonucleotide structure and contains siRNA molecules as the therapeutic nucleic acids.

As used herein, an "amino acid" refers to a molecule containing amine and carboxyl functional groups and a side chain (R) specific to the amino acid. In one embodiment, an amino acid has a structure of the formula:

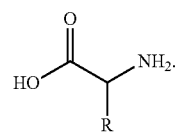

In another embodiment, "amino acid" may refer to a component residue of a peptide or protein having a structure of the formula:

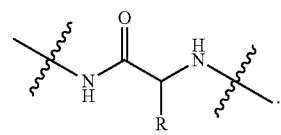

In some embodiments the amino acid is chosen from the group of proteinogenic amino acids. In other embodiments, the amino acid is an L-amino acid or a D-amino acid. In other embodiments, the amino acid is a synthetic amino acid (e.g., a beta-amino acid).

It is understood that certain internucleotide linkages provided herein, including, e.g., phosphodiester and phosphorothioate, comprise a formal charge of −1 at physiological pH, and that said formal charge will be balanced by a cationic moiety, e.g., an alkali metal such as sodium or potassium, an alkali earth metal such as calcium or magnesium, or an ammonium or guanidinium ion.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

Delivery and Distribution

In another aspect, provided herein is a method for selectively delivering a nucleic acid as described herein to a particular organ in a patient, comprising administering to the patient a branched oligonucleotide as described herein, such that the nucleic acid is delivered selectively. In one embodiment, the organ is the liver. In another embodiment, the organ is the kidneys. In another embodiment, the organ is the spleen. In another embodiment, the organ is the heart. In another embodiment, the organ is the brain. In another embodiment, the nucleic acid The compositions described herein promote simple, efficient, non-toxic delivery of metabolically stable oligonucleotides (e.g., siRNA), and promote potent silencing of therapeutic targets in a range of tissues in vivo.

Figure 11A:
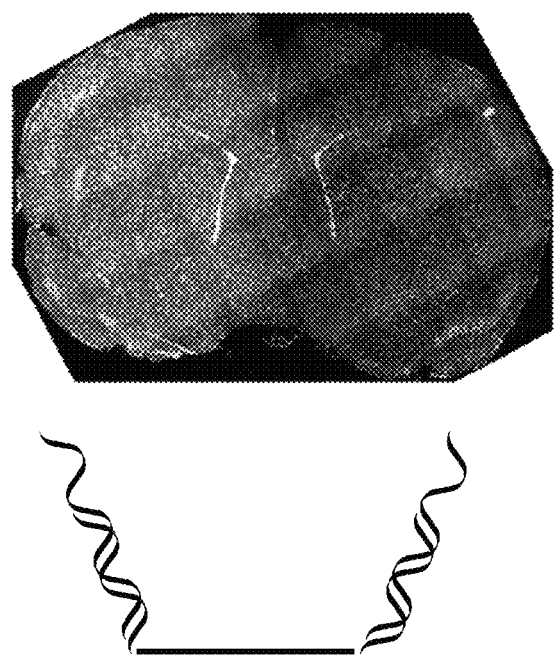
FIGS. 11A-11B show brain distribution of Di-siRNA or TEG only after 48 hours following intra-striatal injection. Intrastriatal injection of 2 nmols of (FIG. 11A) Di-branched oligo (4 nmols of corresponding antisense strand) or (FIG. 11B) TEG-oligo only. N=2 mice per conjugate. Brains collected 48 hours later and stained with Dapi (nuclei, blue). Red—oligo. The left side of brain in FIG. 11A appears bright red, whereas the left side of the brain in FIG. 11B only faintly red.
Figure 11B:
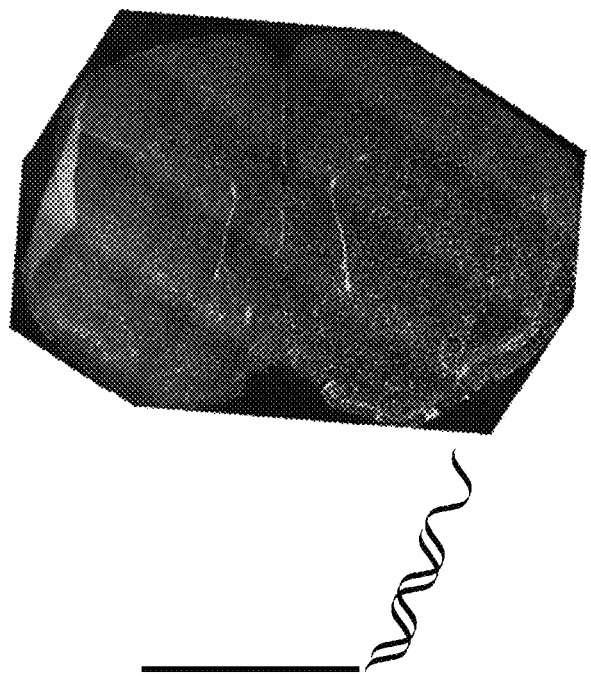

As shown in FIG. 11, Di-siRNA distributes throughout the injected hemisphere of the mouse brain following intrastriatal injection. While a single non conjugated siRNA can silence mRNA in primary neurons, the Di-siRNA structure is essential for enhanced tissue distribution and tissue retention of modified oligo nucleotides. Other conjugates such as cholesterol, although retained, show a steep gradient of diffusion away from the site of injection. The subtle hydrophobicity of the two single stranded phosphorothioated tails supports tissue retention while also allowing for widespread and uniform distribution throughout the ipsilateral hemisphere of the injected brain.

Figure 12:
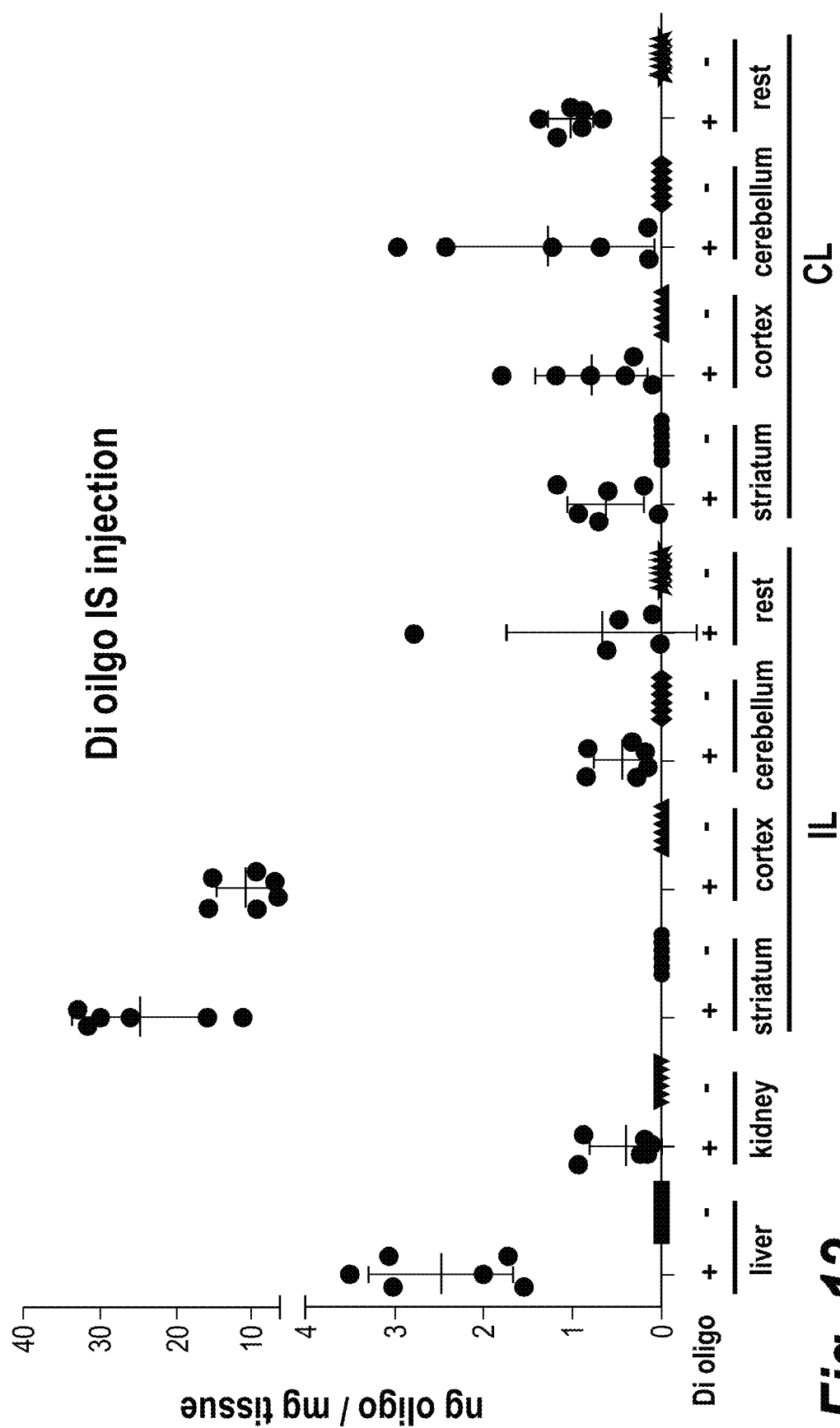
FIG. 12 shows that a single injection of Di-siRNA was detected both ipsilateral and contralateral to the injection site.

As shown in FIG. 12, a single injection of Di-siRNA was detected both ipsilateral and contralateral to the injection site, indicating that spread is not limited to the injected hemisphere, but is also occurring across the midline into the non-injected side. Alternative methods of injection, including intracerebral ventricular, may also facilitate bilateral distribution with only one injection.

Di-siRNA shows a very unique cellular distribution when injected intrastriatally into the brain. Fluorescently labeled Di-siRNA appears to localize preferentially with neurons in the cortex. This selective feature is specific to these compounds and is not true for other siRNA conjugates such as cholesterol which show no cell type preference.

Di-siRNA shows localization to fiber tracts in the striatum but is present within neuronal cell bodies in the cortex. Movement to the cortex may be through diffusion or may be the result of retrograde transport via striatal fiber tracts. The theory that retrograde transport is partially responsible is supported by the fact that some areas of the cortex show full neuronal penetration while neurons in adjacent areas show no Di-siRNA association.

Figure 31:
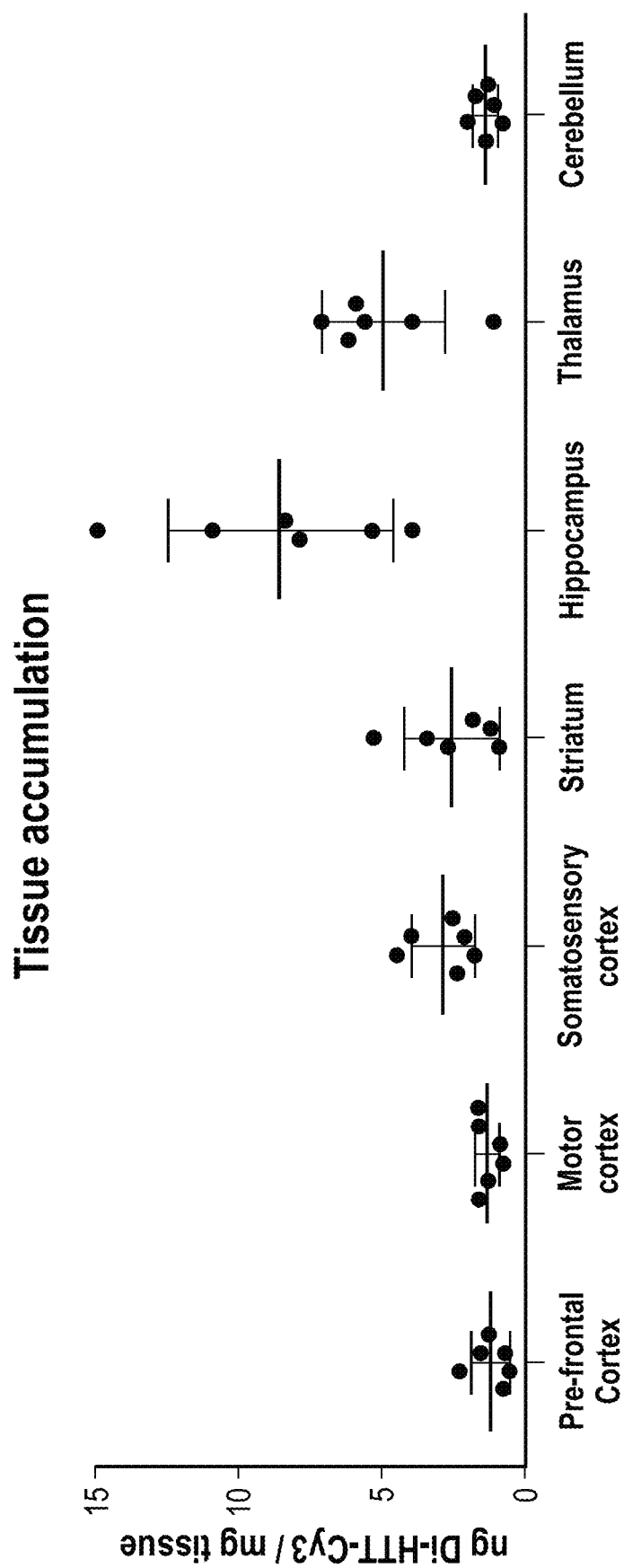
FIG. 31 shows that Di-HTT-Cy3 accumulates in multiple brain regions two weeks post intracerebroventricular injection. A scatter dot plot measures the level of Di-HTT-Cy3 in multiple areas of the brain.
Figure 32A:
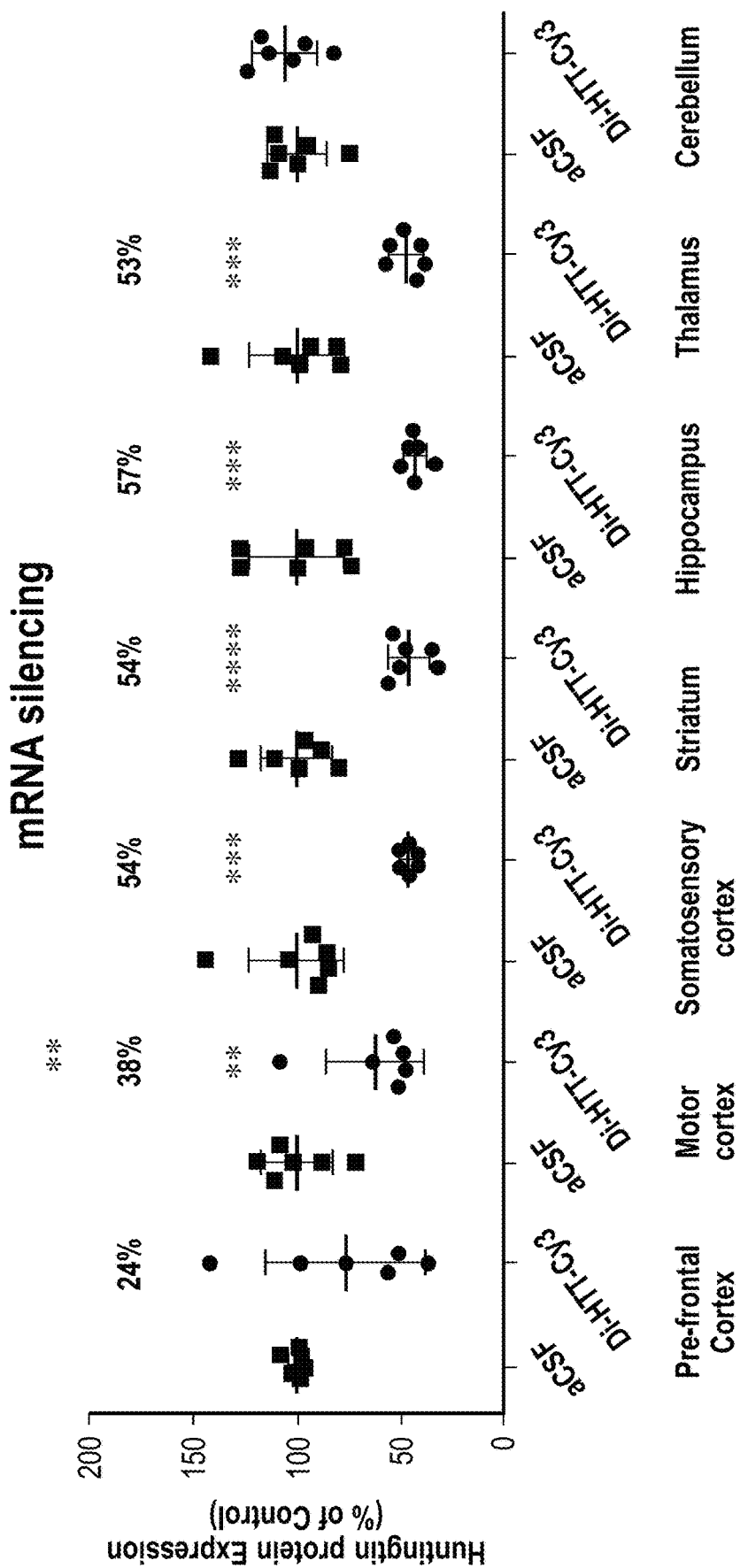
FIG. 32A shows that Di-HTT-Cy3 induces Htt gene silencing in multiple regions of the brain two weeks post intracerebroventricular injection compared to a negative control injection (aCSF). A scatter dot plot measures Htt mRNA levels in multiple areas of the brain.
Figure 32B:
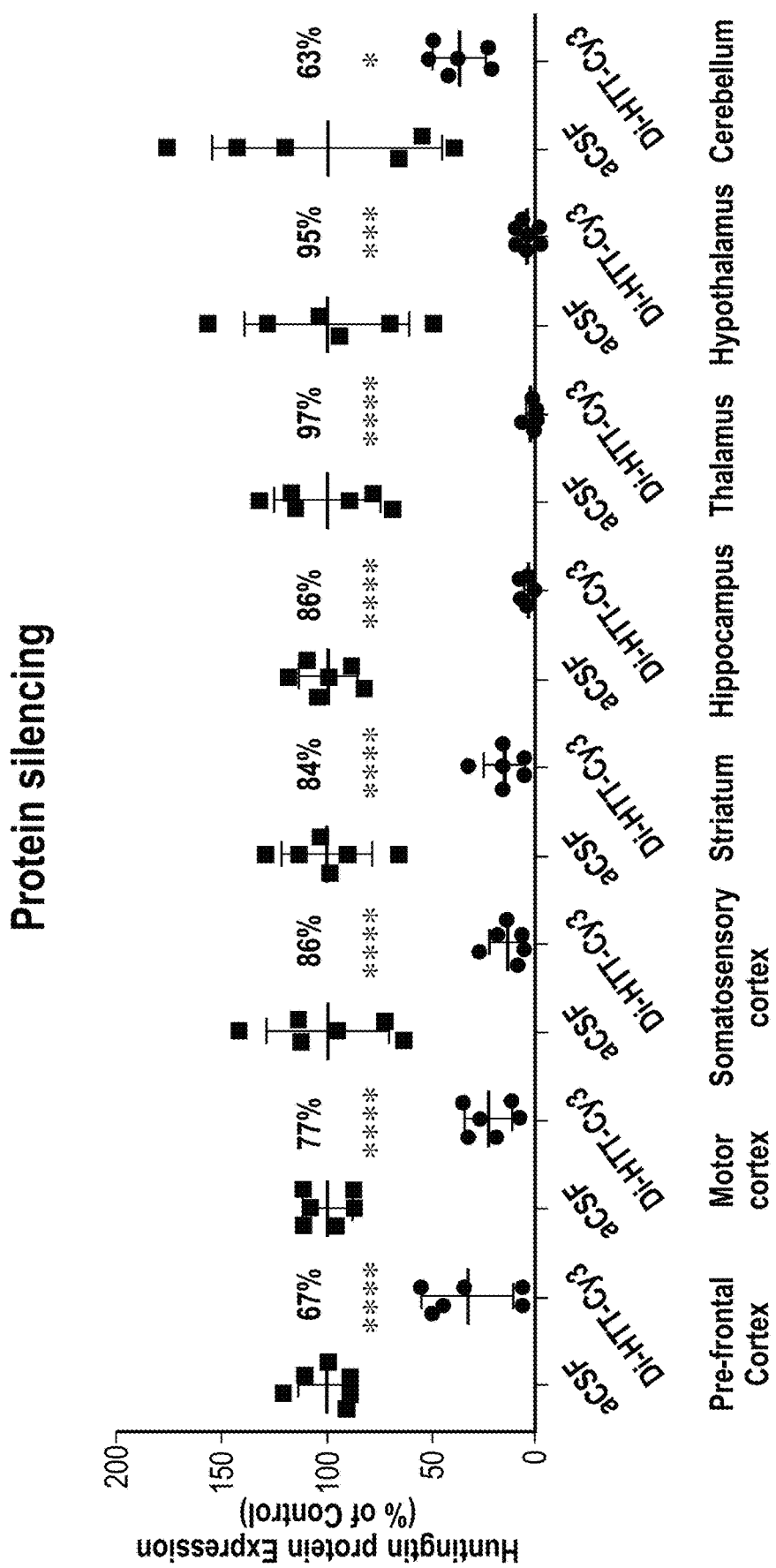
FIG. 32B shows that Di-HTT-Cy3 induces Htt silencing in multiple regions of the brain two weeks post intracerebroventricular injection compared to a negative control injection (aCSF). A scatter dot plot measures Htt protein levels in multiple areas of the brain.

A single therapeutically relevant brain injection of Di-siRNA results in widespread distribution of Di-siRNA throughout the brain. The level of distribution demonstrated in FIGS. 31-32 is unprecedented in the prior art and shows that Di-siRNAs are a promising therapeutic delivery system.

Figure 37:
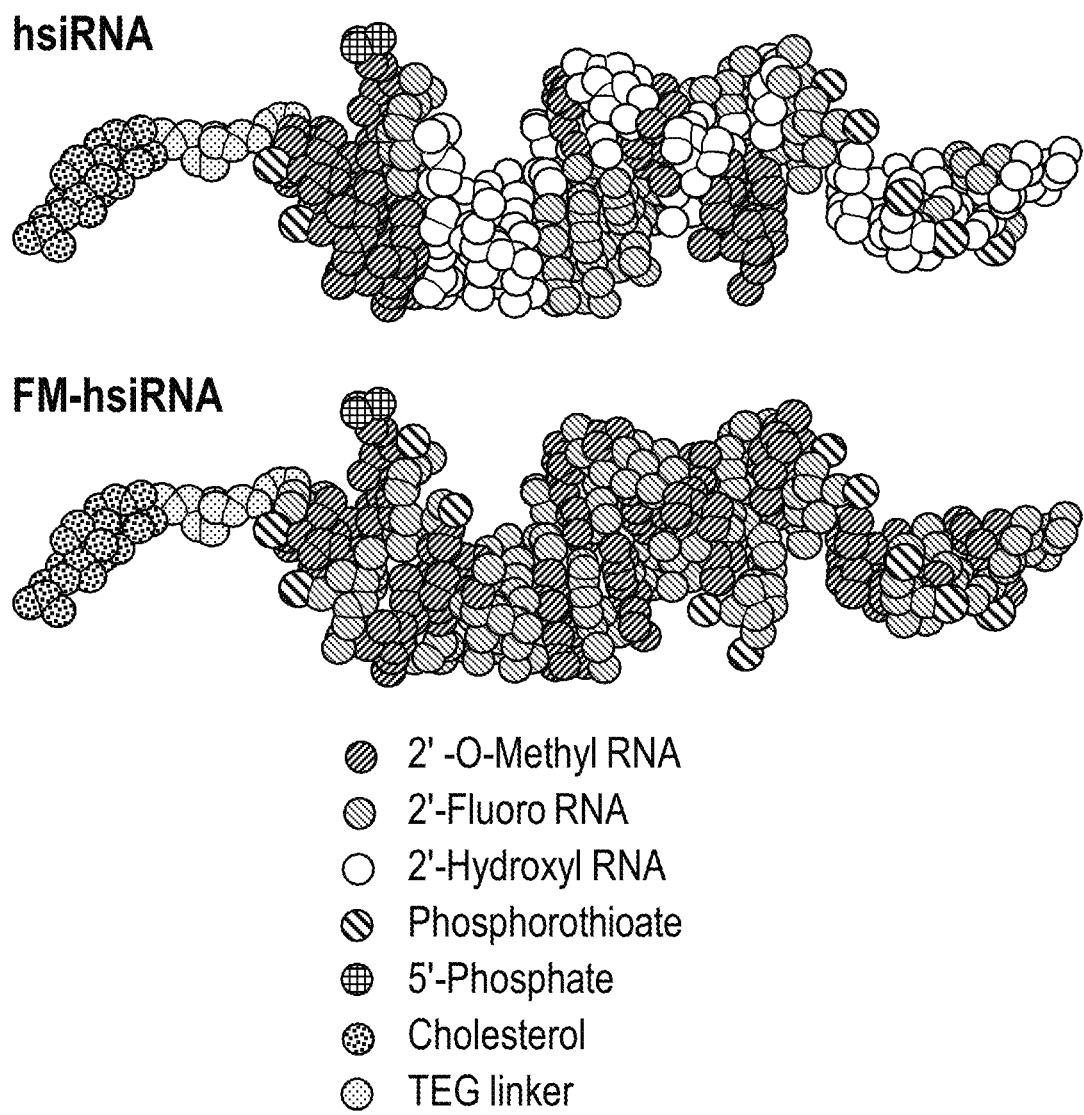
FIG. 37 illustrates the structures of hsiRNA and fully metabolized (FM) hsiRNA.
Figure 38A:
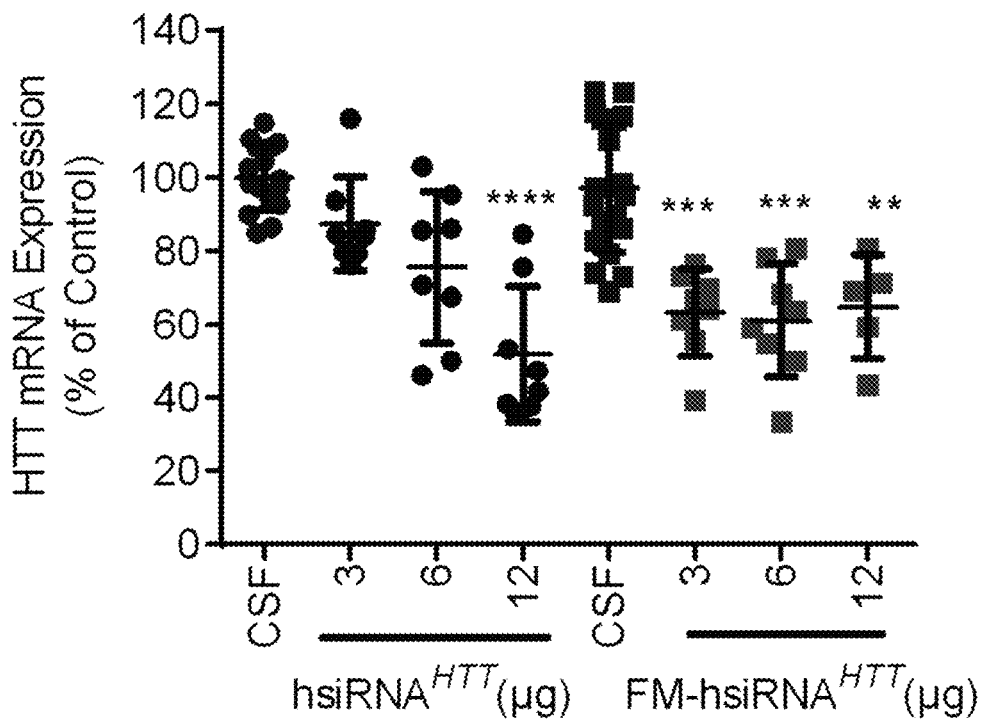
FIGS. 38A-38B show that full metabolic stabilization of hsiRNAs results in more efficacious gene silencing following intrastriatal injection of hsiRNA$^{HTT}$ or FM-hsiRNA$^{HTT}$.
Figure 38B:
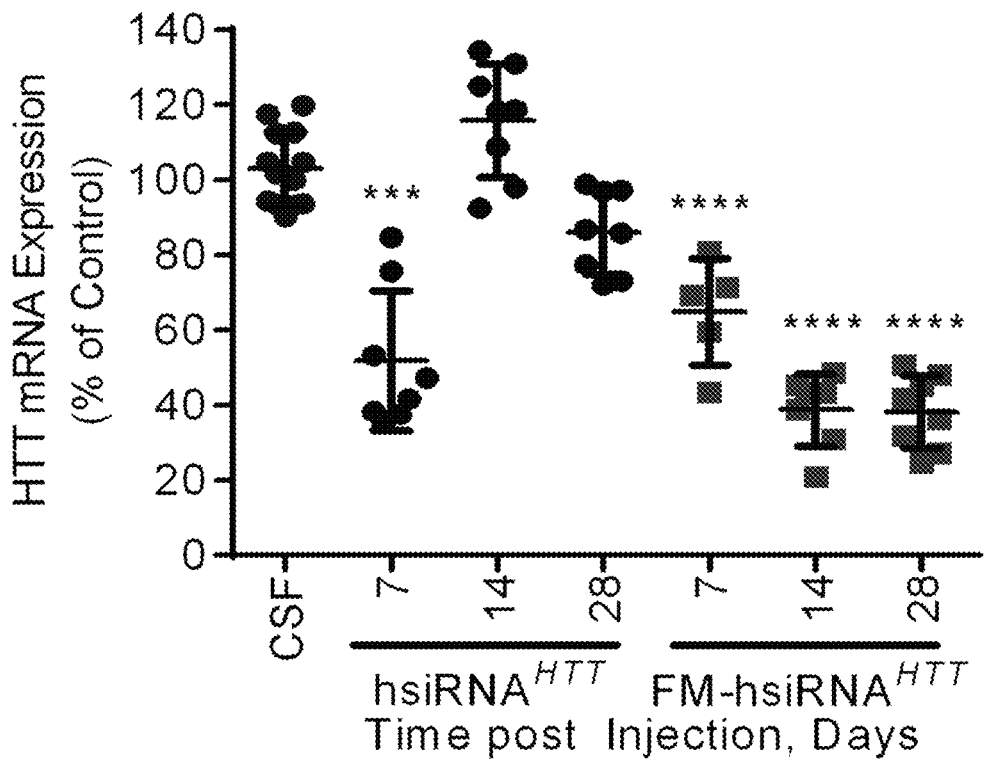
Figure 39:
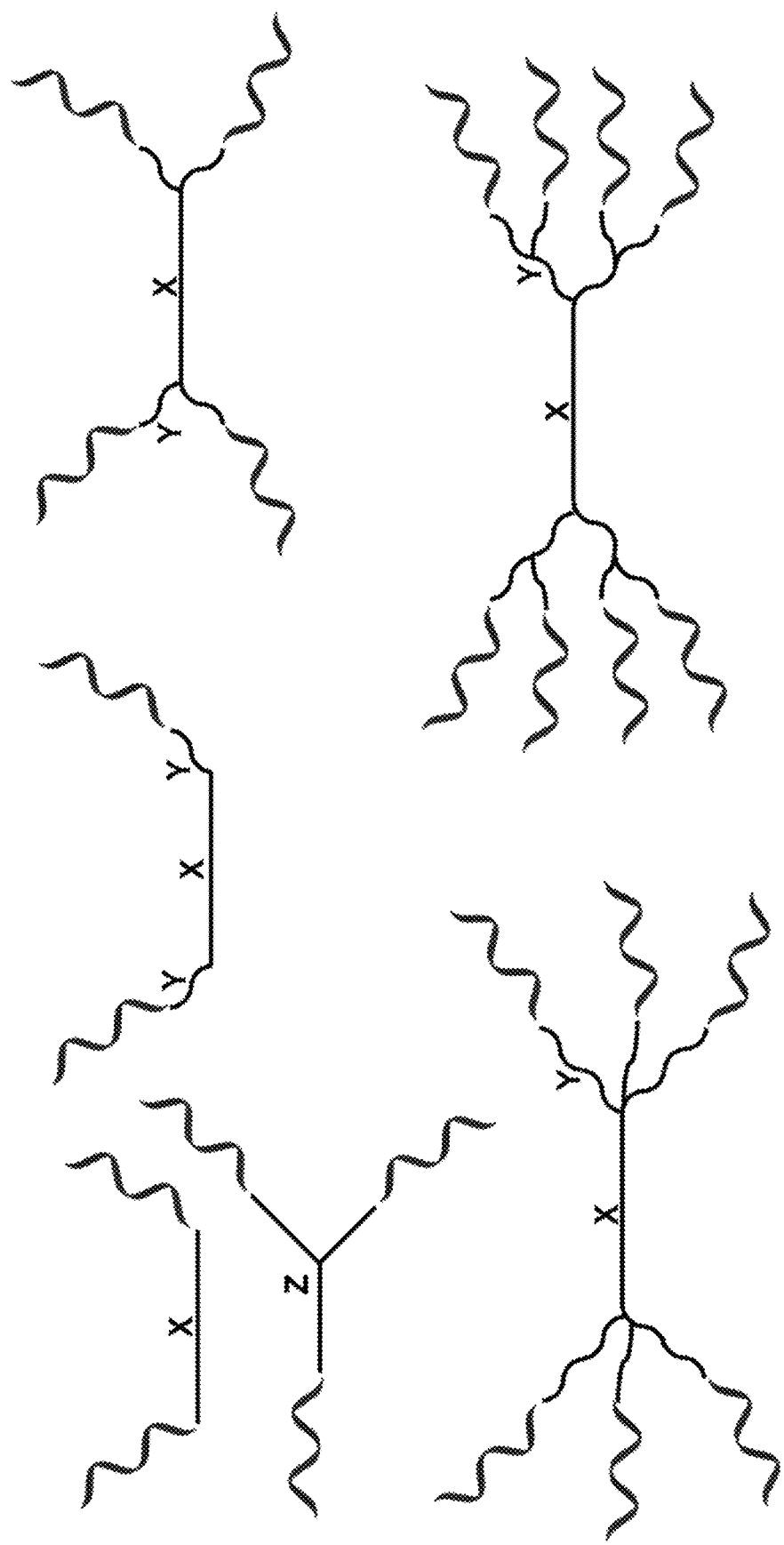
FIG. 39 depicts the chemical diversity of single stranded fully modified oligonucleotides. The single stranded oligonucleotides can consist of gapmers, mixmers, miRNA inhibitors, SSOs, PMOs, or PNAs.
Figure 40:
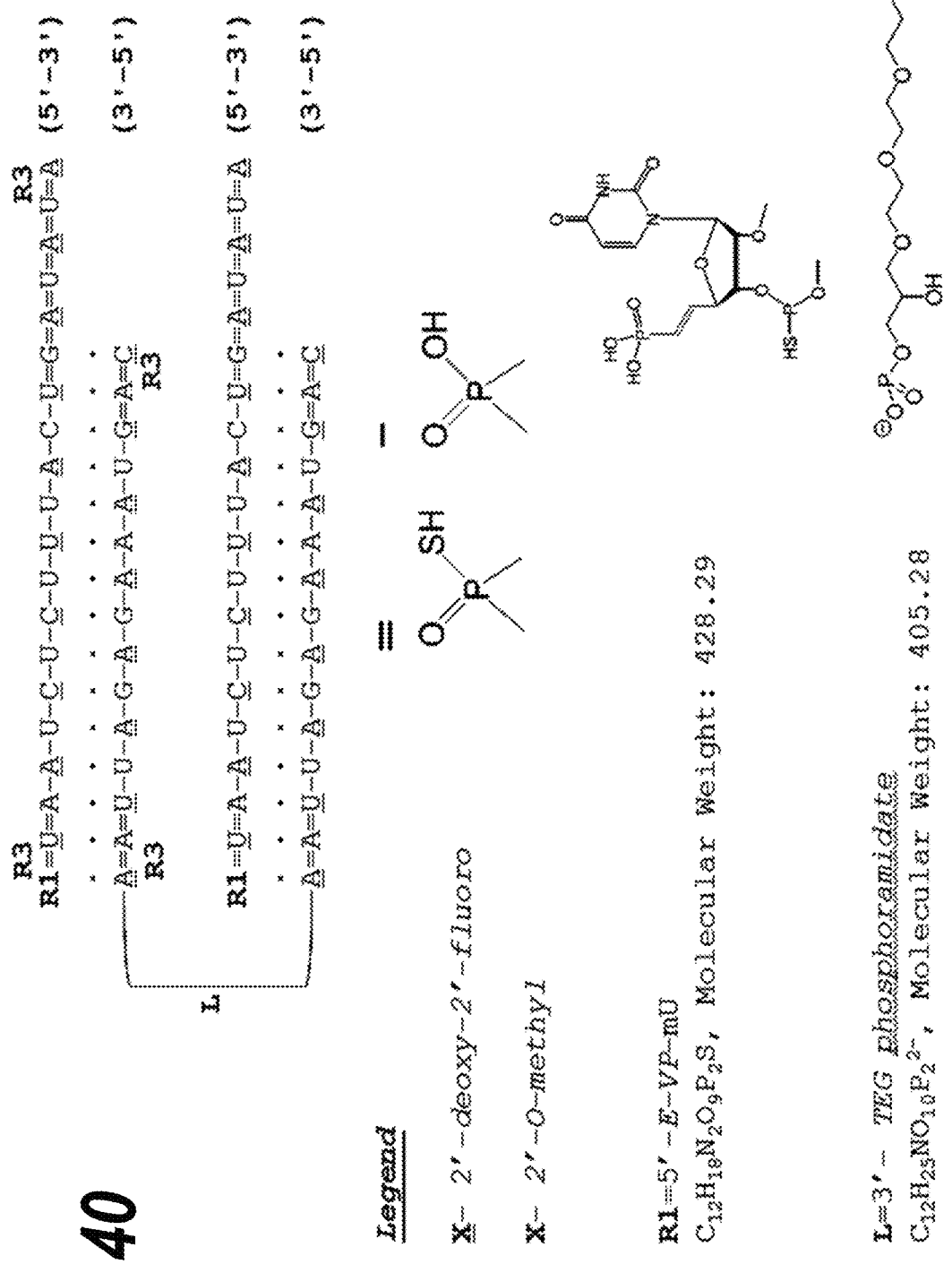
FIG. 40 depicts Di-HTT with a TEG phosphoramidate linker.
Figure 41:
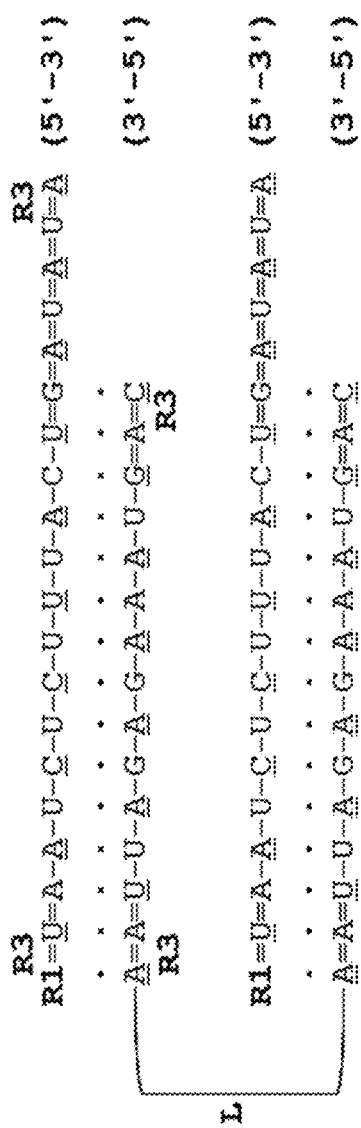
FIG. 41 depicts Di-HTT with a TEG di-phosphate linker.
Figure 41:
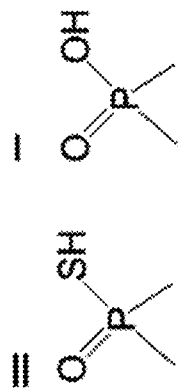
Figure 41:
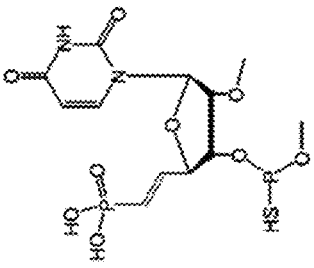
Figure 41:
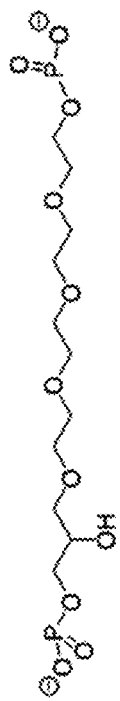
Figure 42:
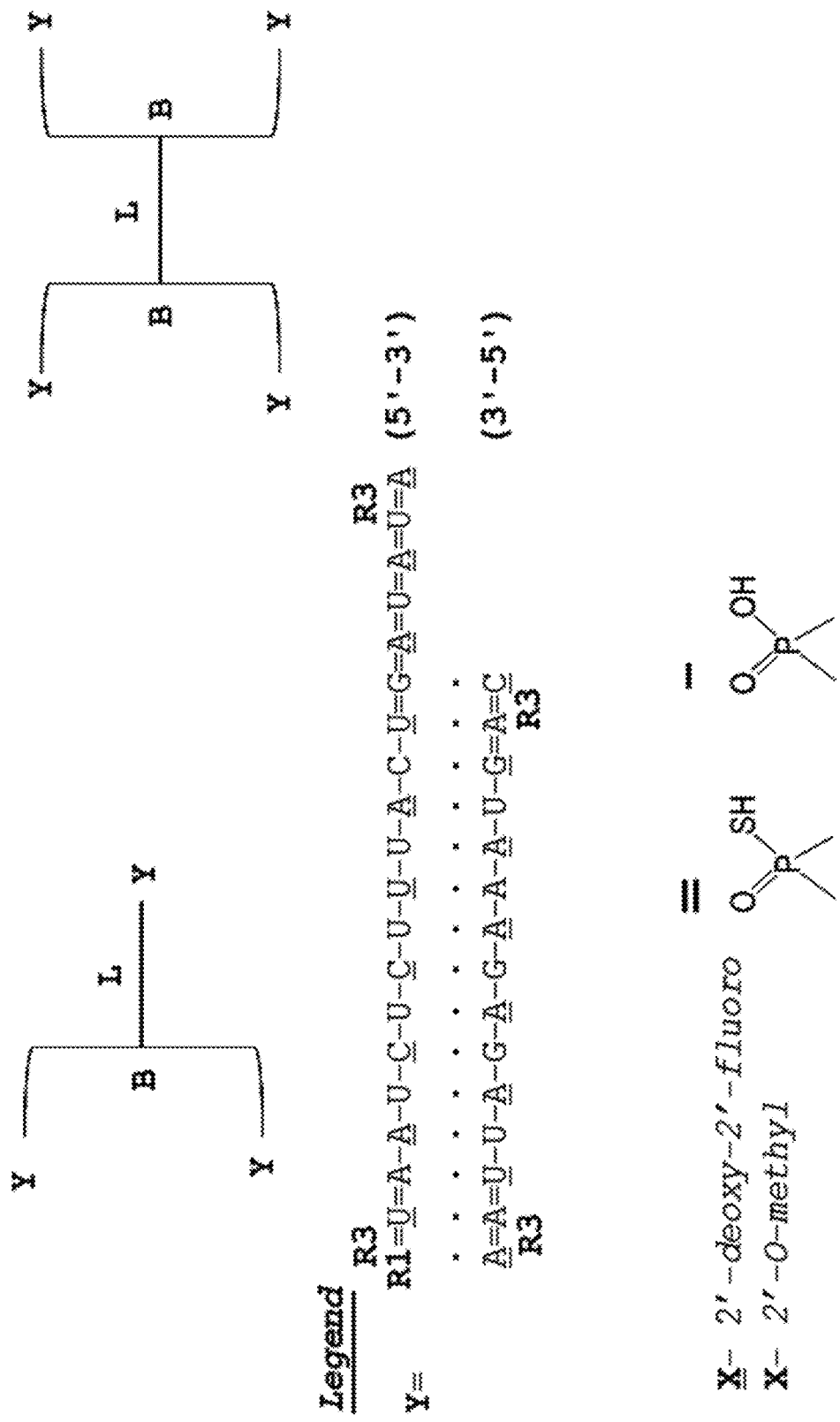
FIG. 42 depicts variations of Di-HTT with either two oligonucleotide branches or four oligonucleotide branches.
Figure 43:
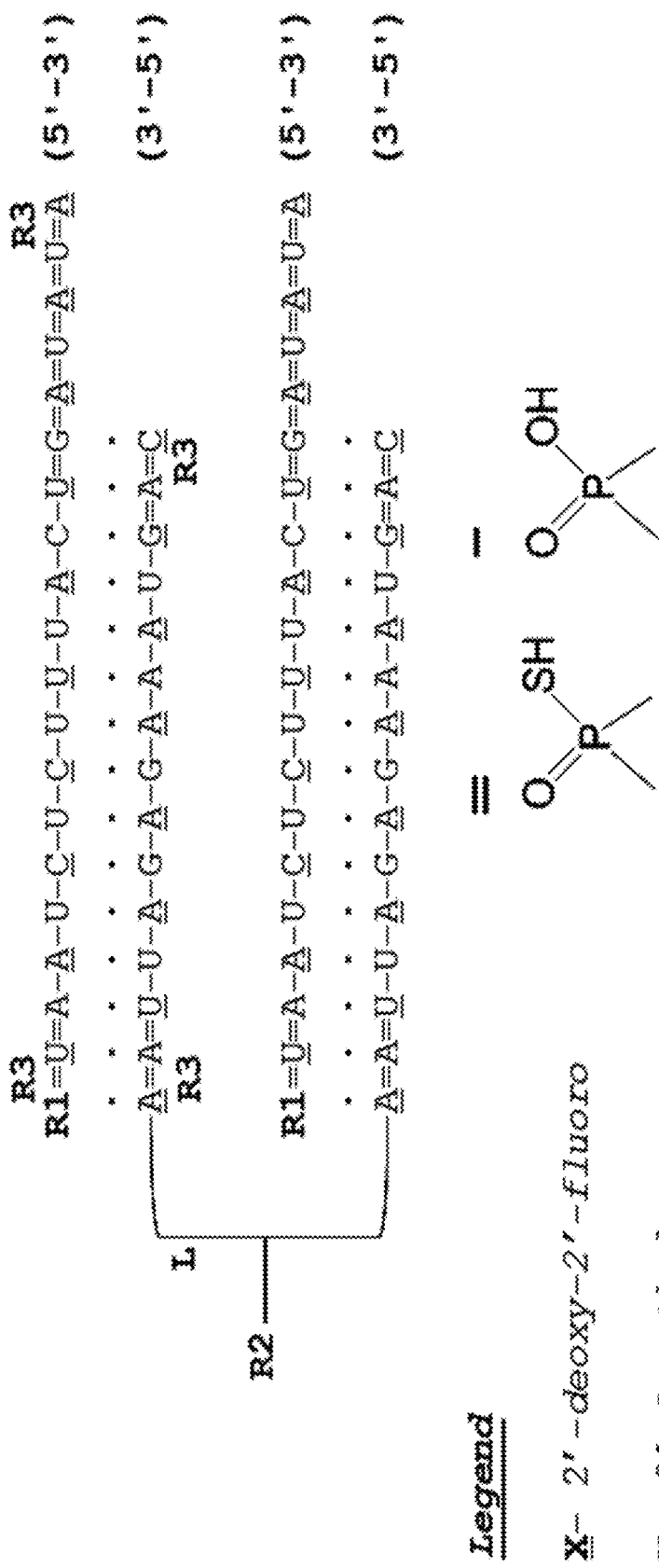
FIG. 43 depicts another variant of Di-HTT of a structure with two oligonucleotide branches and R2 attached to the linker.

Di-siRNA shows widespread distribution throughout the body following a single intravenous injection. As shown in FIG. 37, significant levels of Di-siRNAs were detected in mouse liver, skin, brain, kidney, spleen, pancreas, colon, fat, lung, muscle, and thymus. The finding that Di-siRNAs are present in the brain following intravenous injection also demonstrates that the Di-siRNA structures efficiently cross the blood-brain barrier.

Silencing

In some embodiments, compounds of the invention promote about 90% striatal silencing and about 65% cortical silencing in vivo in brain with a single injection, with no indication of toxicity. In some embodiments, compounds of the invention exhibit about 60% silencing throughout all regions of the spinal cord with intrathecal injection.

Single injection of Di-siRNA induces robust silencing in both the striatum and cortex of mouse brain. This level of efficacy has never been demonstrated previously for non-conjugated siRNAs. Although Di-siRNA appears visually associated with fiber tracts in striatum, the efficacy observed clearly indicates that striatal neurons are internalizing Di-siRNA to a significant degree. In experiments, intrastriatal injection 2 nmols Di-siRNA (4 nmols of corresponding antisense HTT strand). Animals sacrificed 7 days post-injection. Tissue punches taken from the 300 um brain slices from the striatum and cortex. Di-siRNA antisense strands present in different brain regions, liver, and kidney were quantified using Cy3-labeled complimentary PNA to hybridize to the strand and HPLC to quantify ng of oligo per mg of tissue. aCSF—Artificial CSF.

Figure 10A:
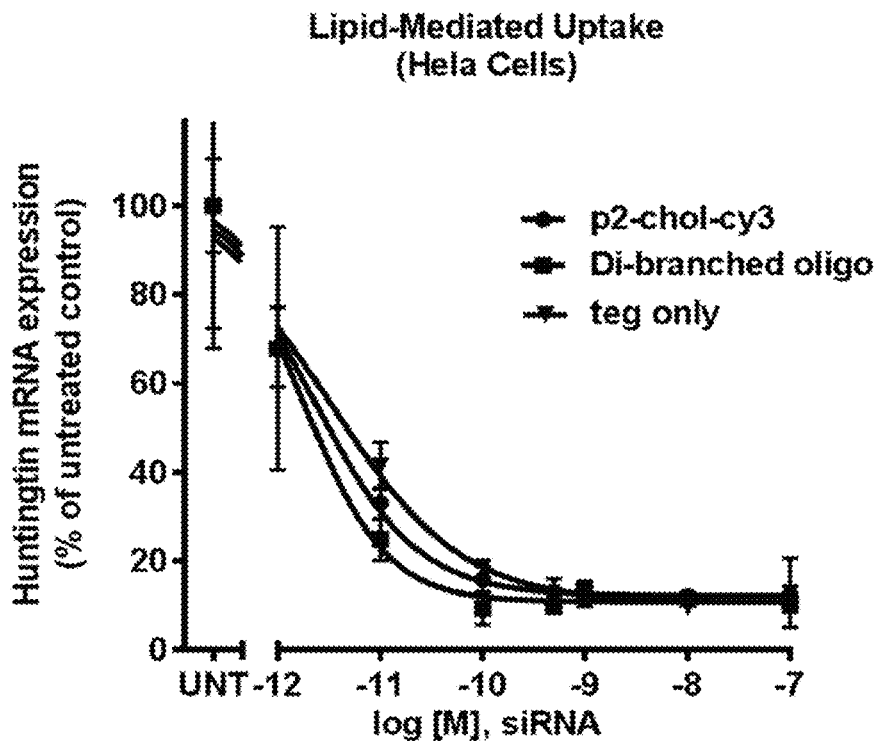
FIGS. 10A-10C show in vitro efficacy data.
Figure 10B:
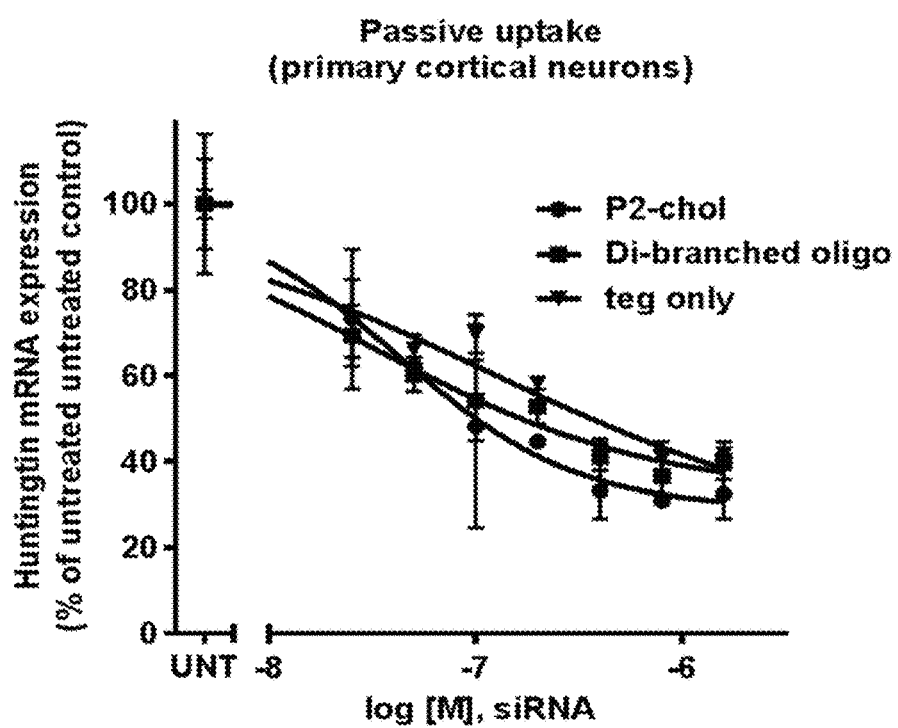
Figure 10C:
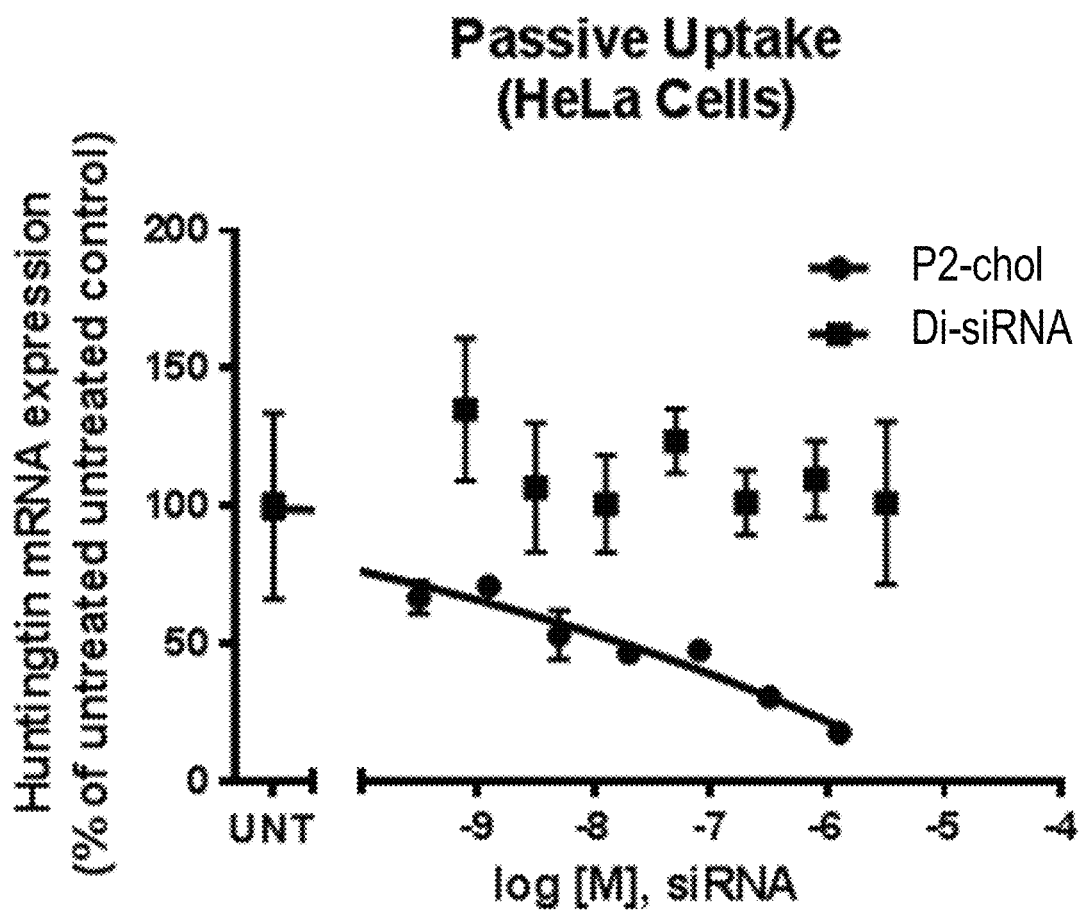

As shown in FIG. 10, Di-siRNA shows equal efficacy relative to a single siRNA duplex following lipid-mediated transfection in HeLa cells, indicating that RISC loading is not hindered by the tethering of two siRNA duplexes to a linker. Di-siRNA is not efficacious in HeLa cells without transfection, however in primary cortical neurons, one phosphorothioated tail is enough to induce at least 60% silencing, suggesting that phosphorothiation is an effective method for delivering siRNA to primary neurons, without formulation.

Figure 13A:
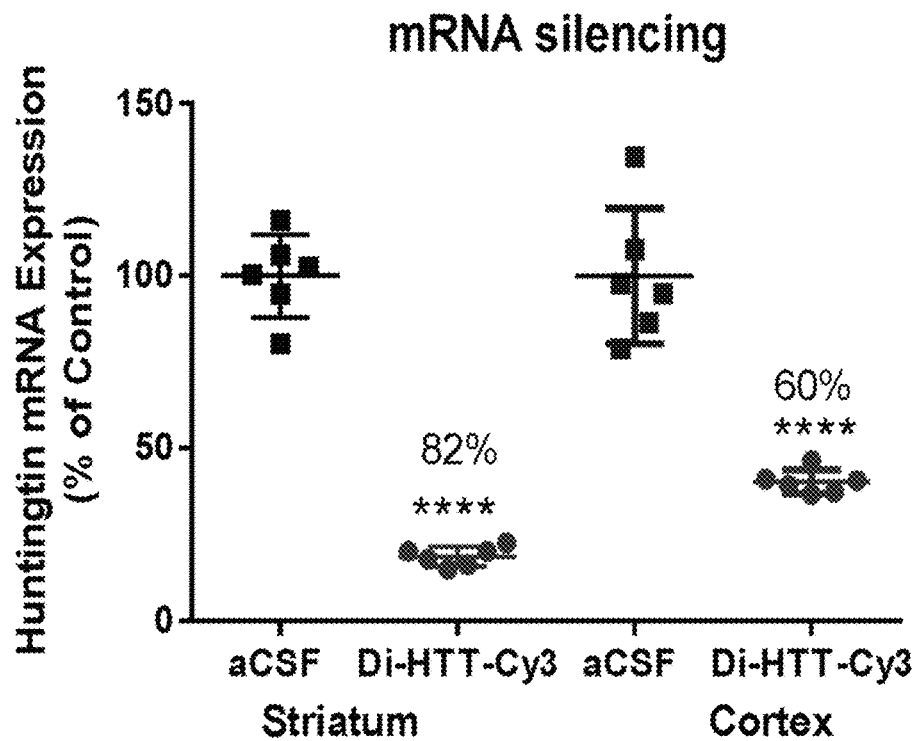
FIGS. 13A-13B show Di-hsiRNA wide distribution and efficacy in mouse brain.
Figure 13B:
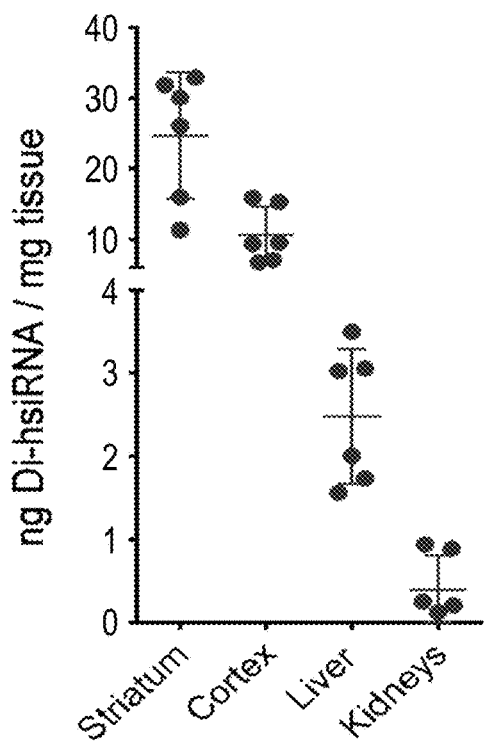
Figure 15A:
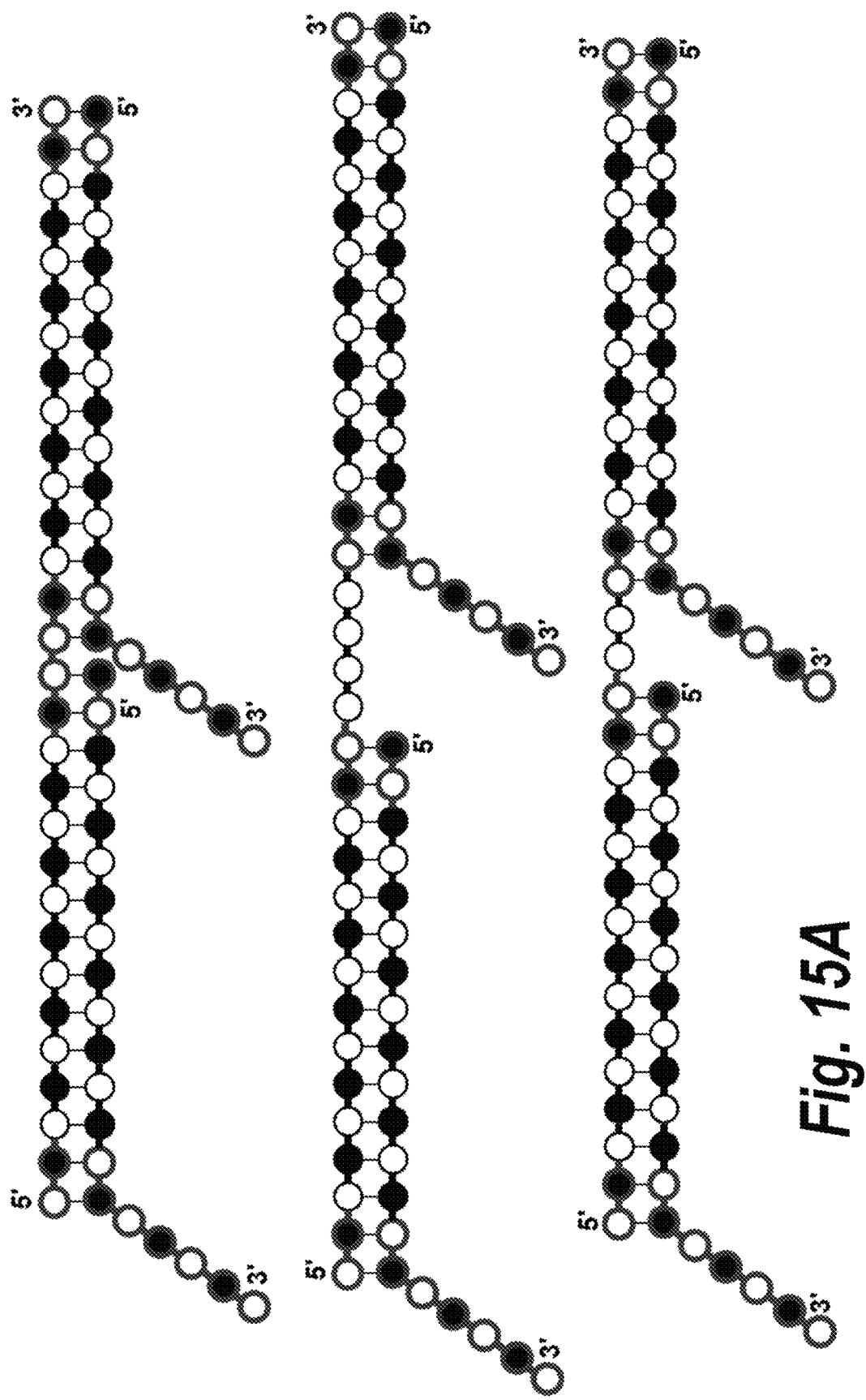
FIGS. 15A-15C show branched oligonucleotides of the invention, FIG. 15A—formed by annealing three oligonucleotides. The longer linking oligonucleotides may comprise a cleavable region in the form of unmodified RNA, DNA or UNA.
Figure 15B:
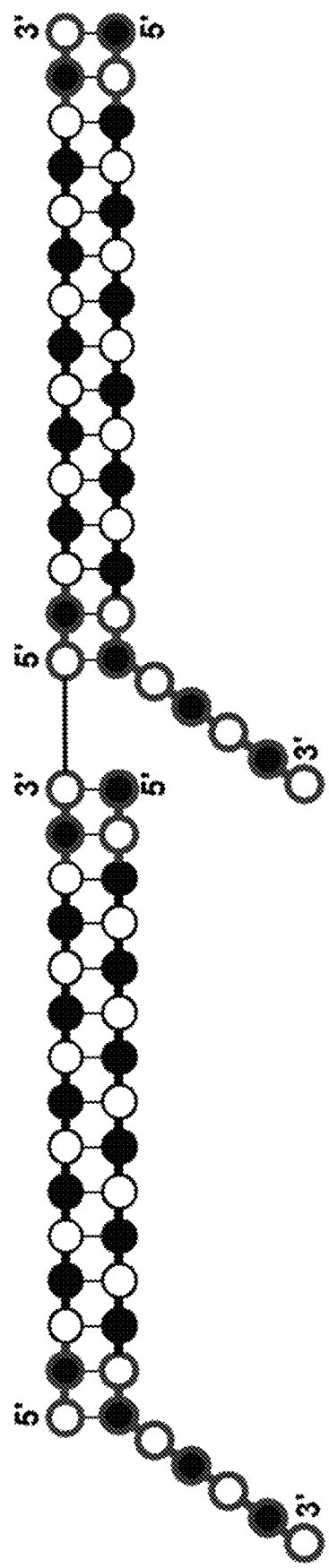
Figure 15C:
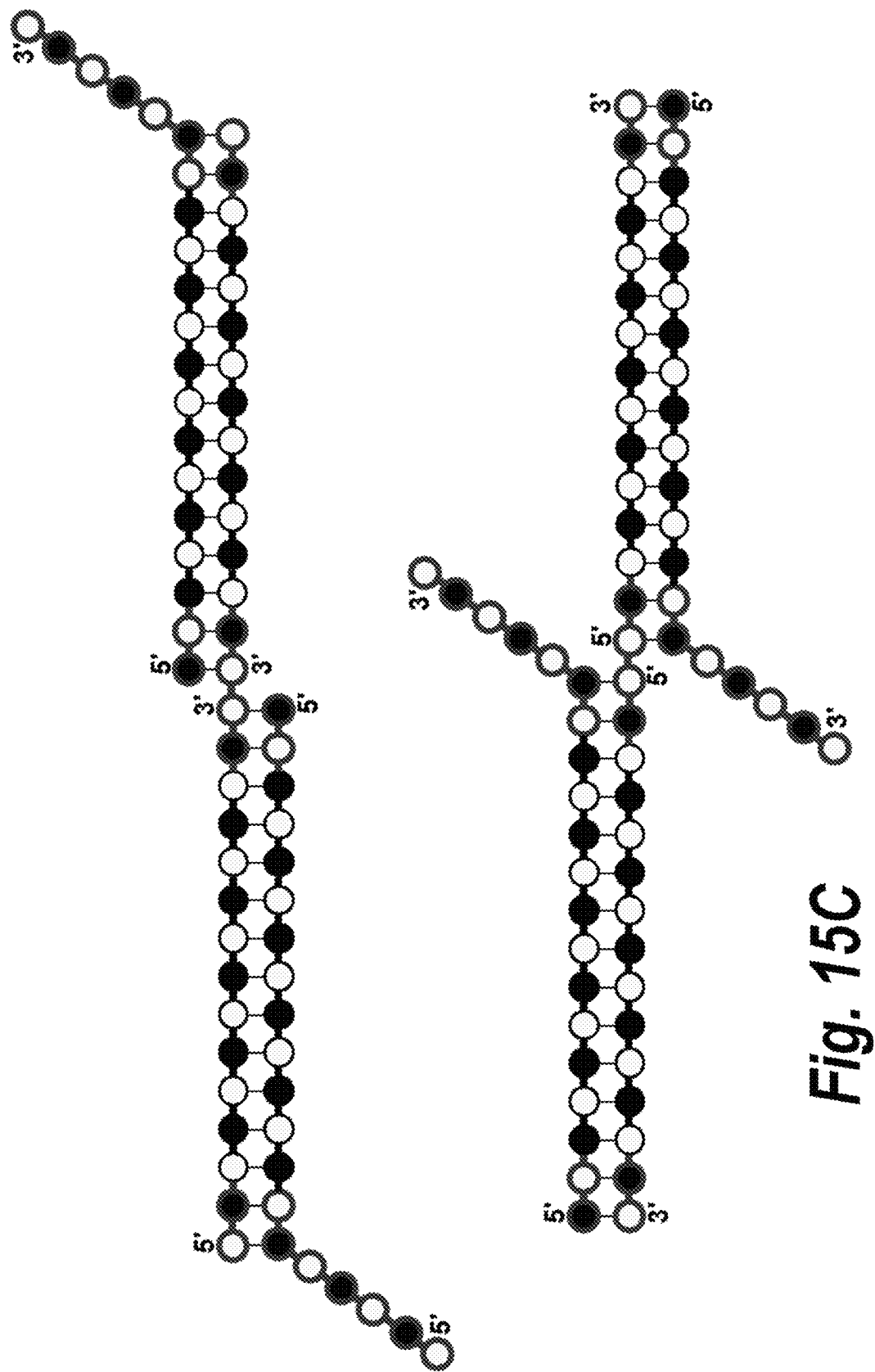

As shown in FIG. 13, a single injection of Di-siRNA induces robust silencing in both the striatum and cortex of mouse brain. Although a 63× image of pyrimidal neurons containing Cy3-labeled Di-branched oligo shows that Di-siRNA is visually associated with fiber tracts in the striatum, the efficacy observed clearly indicates that striatal neurons are internalizing Di-siRNA to a significant degree.

As shown in FIG. 14, Di-siRNA shows robust and even silencing throughout the spinal cord following intrathecal injection. A single injection of Di-siRNA in the lumbar region of the spinal cord silences mRNA to the same degree in the cervical, thoracic and lumbar regions indicating even and long range distribution.

Figure 24A:
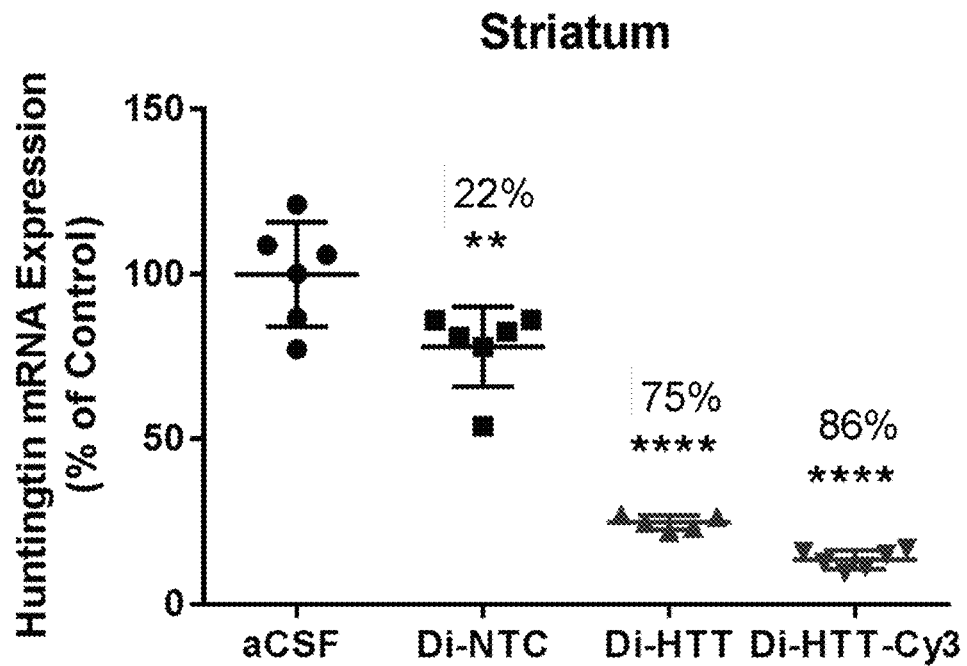
FIGS. 24A-24B show that Di-HTT effectively silences HTT gene expression in both the striatum and the cortex following intrastriatal injection and that Di-HTT-Cy3 is slightly more efficacious than Di-HTT (unlabeled).
Figure 24B:
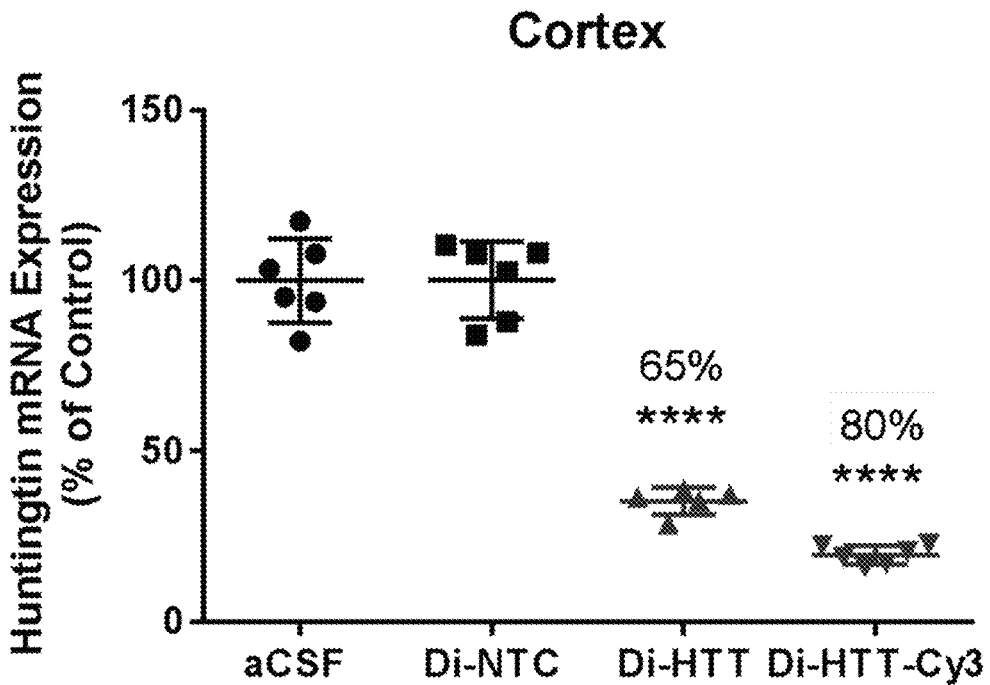
Figure 25:
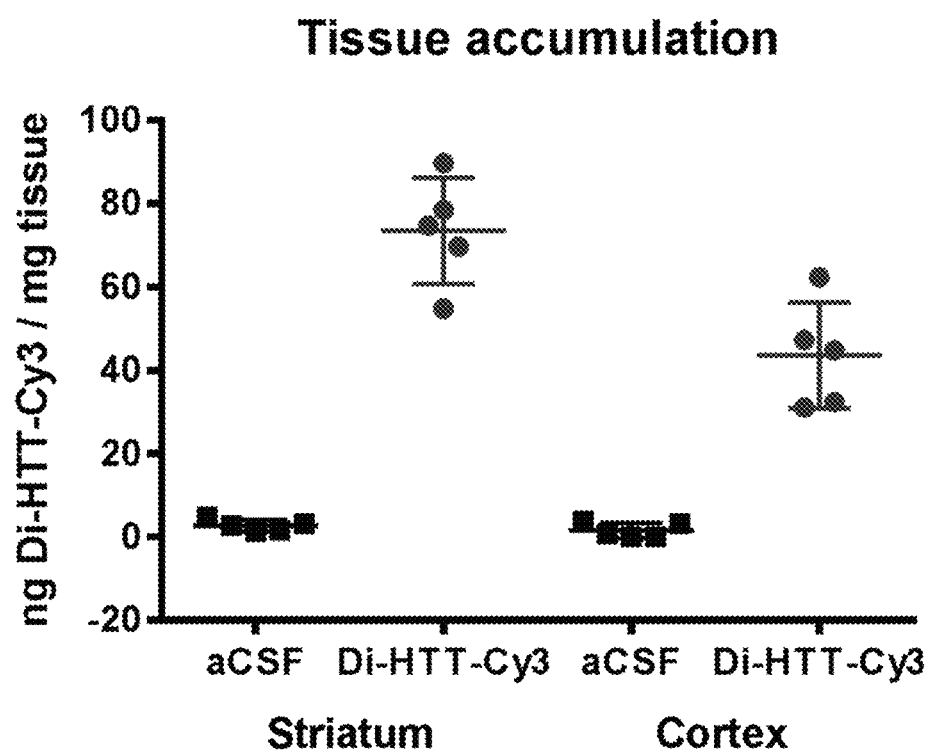
FIG. 25 depicts a scatter dot plot measuring Di-HTT-Cy3 levels in the striatum and cortex. The plot shows that significant levels of Di-HTT-Cy3 are still detectable two weeks post intrastriatal injection.

As shown in FIG. 24, Di-siRNA labeled with Cy3 induces robust silencing in both the striatum and cortex of mouse brain. The mRNA expression levels show that the addition of Cy3 to the branched oligonucleotide compositions enhances silencing as compared to the unlabeled Di-siRNA.

Figure 23A:
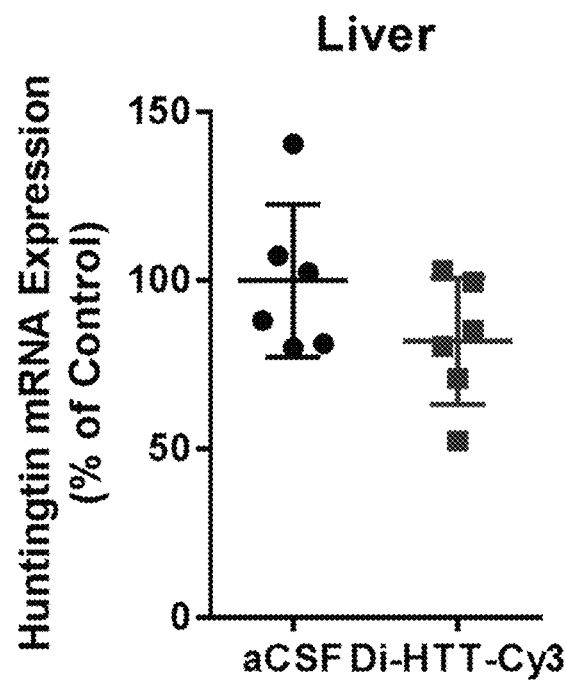
FIGS. 23A-23B show that Di-HTT-Cy3 does not effectively induce silencing in the liver or kidneys following intrastriatal injection.
Figure 23B:
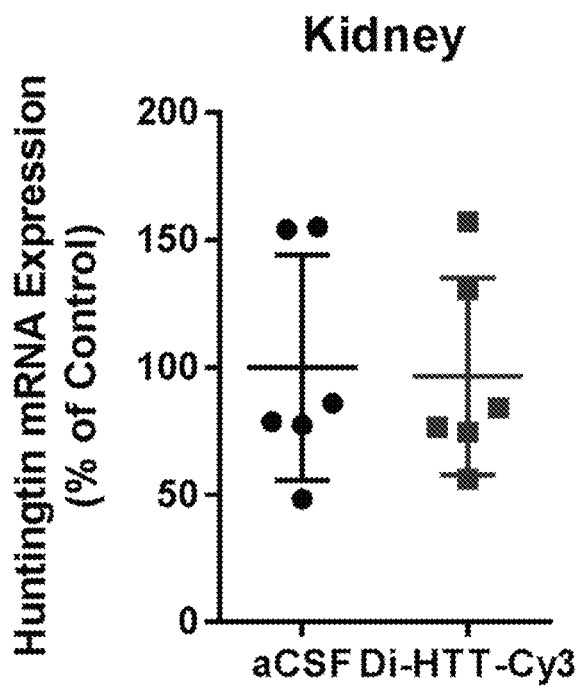

As shown in FIGS. 23-24, a single intrastriatal injection resulted in silencing in both the cortex and striatum of mouse brain but did not result in any significant silencing in the liver or kidney. This demonstrates that branched oligonucleotides can specifically target an organ of interest.

Figure 26A:
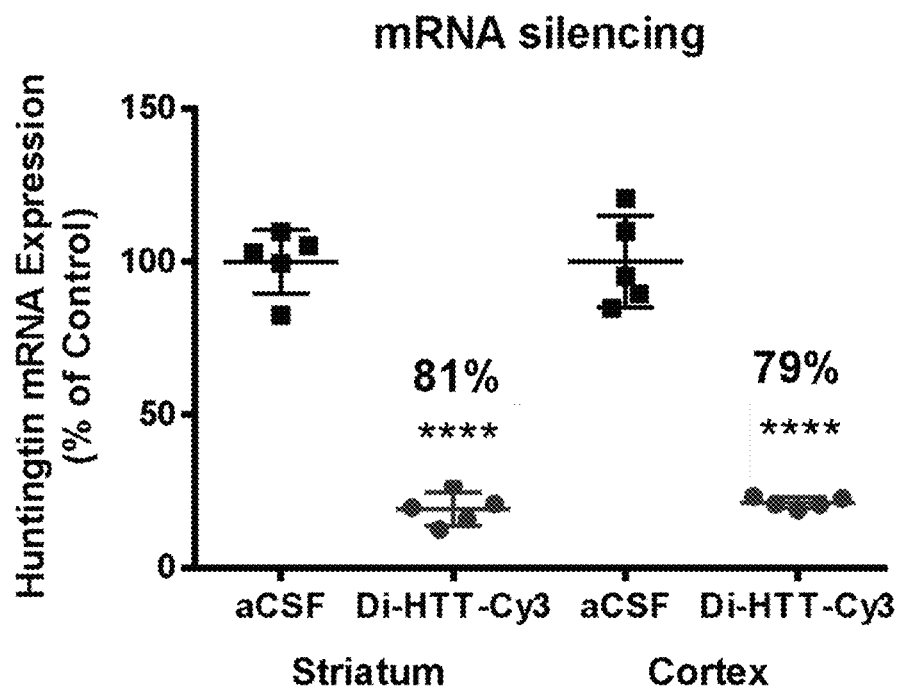
FIGS. 26A-26B show that Di-HTT-Cy3 effectively silences HTT mRNA and protein expression in both the striatum and the cortex two weeks post intrastriatal injection.
Figure 26B:
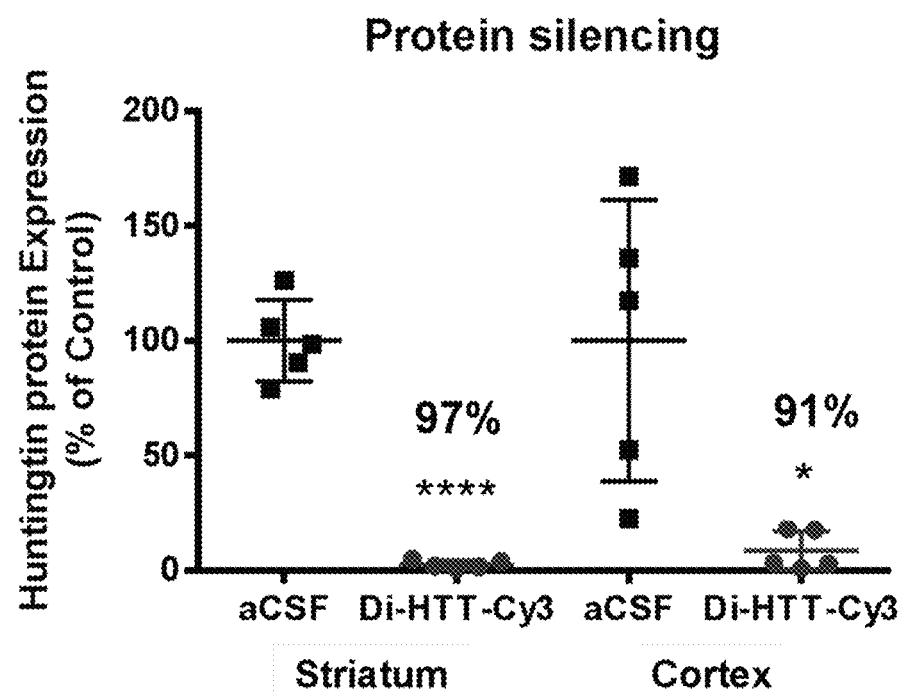

As shown in FIG. 26, a single injection of Di-siRNA continues to maintain robust silencing two weeks after the injection in both the striatum and cortex of mouse brain. Di-siRNA is stable and effective for at least two weeks in vivo.

Figure 33:
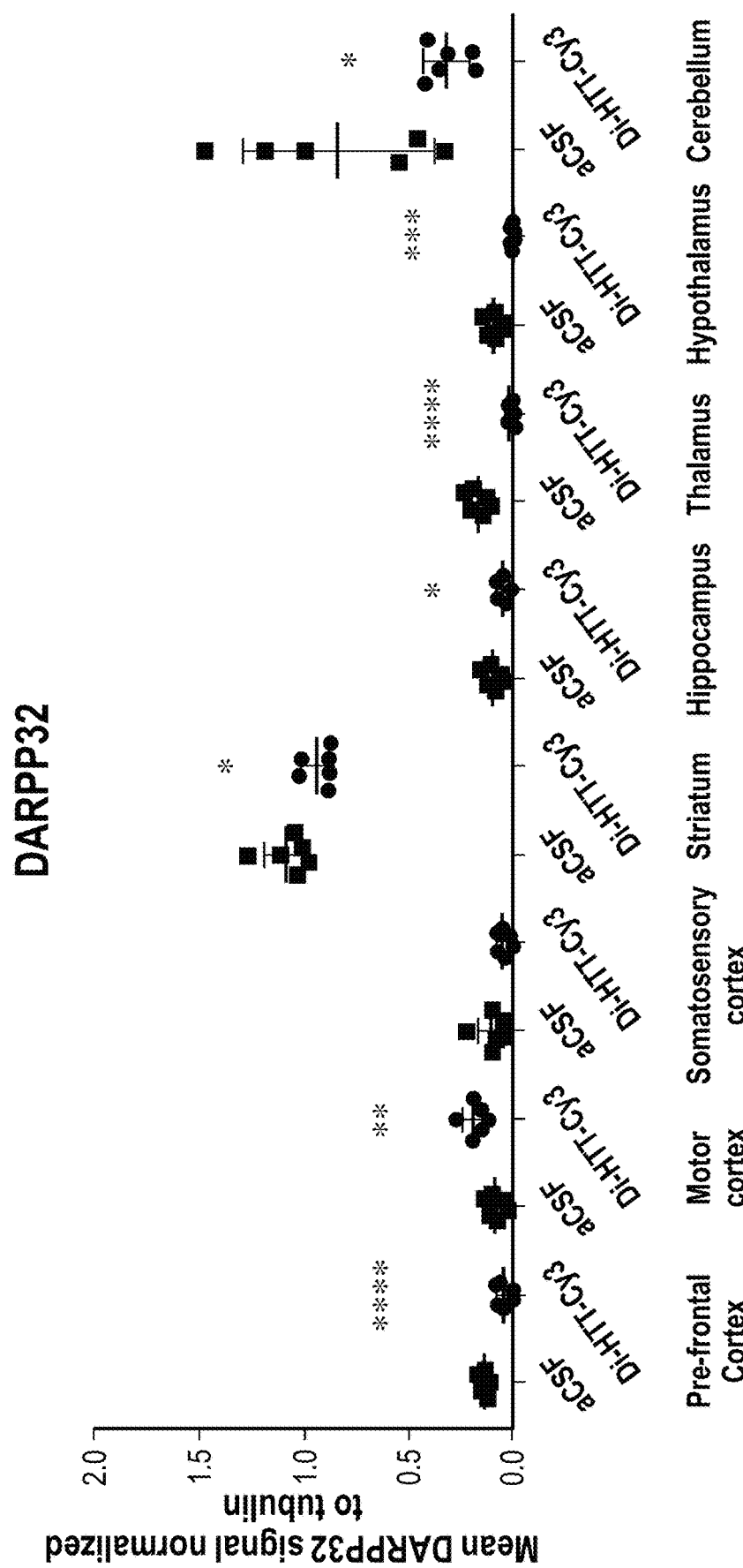
FIG. 33 shows that intracerebroventricular injection of high dose Di-HTT-Cy3 causes minor toxicity in vivo. A scatter dot plot measures DARPP32 signal in multiple regions of the brain following Di-HTT-Cy3 of aCSF injection.
Figure 34:
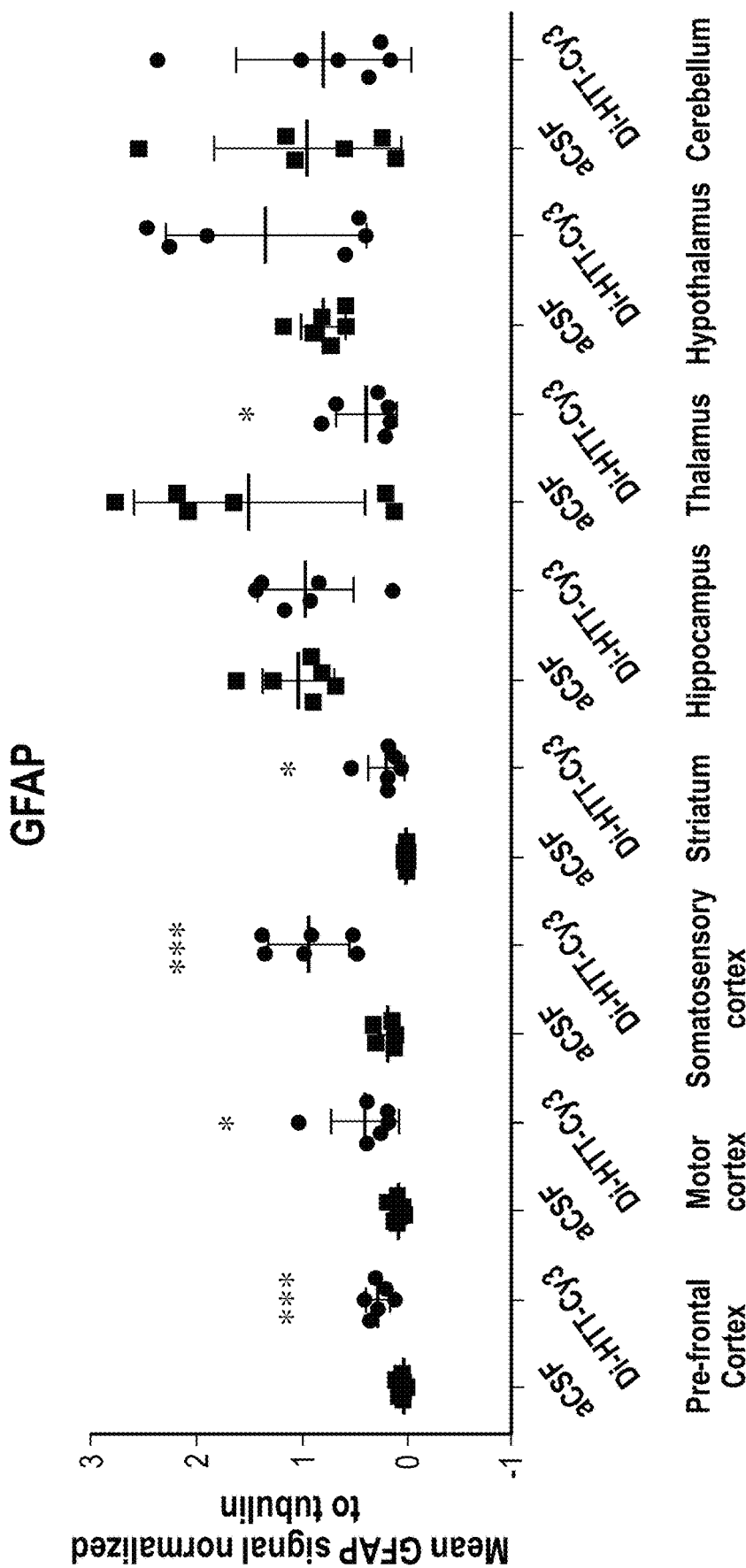
FIG. 34 shows that intracerebroventricular injection of high dose Di-HTT-Cy3 causes significant gliosis in vivo. A scatter dot plot measures DARPP32 signal in multiple regions of the brain following Di-HTT-Cy3 of aCSF injection.

As shown in FIG. 33 and FIG. 34, a therapeutically relevant single injection of Di-siRNA induces significant silencing in multiple areas of the brain. This is the first example of widespread siRNA silencing in the brain following a single therapeutically relevant injection. These results demonstrate that Di-siRNAs are an efficacious option for RNA therapeutics.

Modified RNA Silencing Agents

In certain aspects of the invention, an RNA silencing agent (or any portion thereof) of the invention as described supra may be modified such that the activity of the agent is further improved. For example, the RNA silencing agents described in above may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the invention may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g.

wild-type mRNA), without appreciably affecting the specificity of the RNA silencing agent for a target mRNA (e.g. gain-of-function mutant mRNA).

In preferred embodiments, the RNA silencing agents of the invention are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is preferred because it has relatively minor effect on the stability of the RNA duplex or the duplex formed by the guide strand of the RNA silencing agent and the target mRNA. Exemplary universal nucleotide include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In particularly preferred embodiments, the universal nucleotide is an inosine residue or a naturally occurring analog thereof.

In certain embodiments, the RNA silencing agents of the invention are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destablilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In preferred embodiments, the destabilizing nucleotide is introduced in the same strand or strand portion that contains the specificity-determining nucleotide.

2) Modifications to Enhance Efficacy and Specificity

In certain embodiments, the RNA silencing agents of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. Preferably the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S 5') of said RNA silencing agent.

In one embodiment, the asymmetry of an RNA silencing agent of the invention may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. Preferably, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between the 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). Preferably, the base pair is selected from the group consisting of an I:A, I:U and I:C. In yet another embodiment, the asymmetry of an RNA silencing agent of the invention may be enhanced such that there is at least one base pair comprising a modified nucleotide. In preferred embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a preferred aspect, the invention features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a preferred embodiment of the present invention, the RNA silencing agents may contain at least one modified nucleotide analogue. The nucleotide analogues may be located at positions where the target-specific silencing activity, e.g., the RNAi mediating activity or translational repression activity is not substantially effected, e.g., in a region at the 5'-end and/or the 3'-end of the siRNA molecule. Particularly, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH- group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particularly preferred modifications include 2'-fluoro-cytidine, 2'-fluorouridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moities of the instant invention. Additional modified residues include, deoxy-abasic, inosine, N3-methyl-uridine, N6,N6-dimethyl-adenosine, pseudouridine, purine ribonucleoside and ribavirin. In a particularly preferred embodiment, the 2' moiety is a methyl group such that the linking moiety is a 2-O-methyl oligonucleotide.

In an exemplary embodiment, the RNA silencing agent of the invention comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-O,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the invention comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the invention includes RNA silencing agents having two complementary strands of nucleic acid, wherein the two strands are crosslinked. The invention also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an 0 with an S, in the phosphate backbone, e.g., the provision of a phosphorothioate modification, on the U or the A or both, especially on an antisense strand; e.g., with the replacement of a P with an S; (c) replacement of the U with a C5 amino linker; (d) replacement of an A with a G (sequence changes are preferred to be located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' OMe moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

4) Modifications to Enhance Cellular Uptake

In other embodiments, a compound of the invention may be modified with chemical moieties, for example, to enhance cellular uptake by target cells (e.g., neuronal cells). Thus, the invention includes RNA silencing agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, a compound of the invention is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin D, DHA, DHAg2, EPA, vitamin E, vitamin K, vitamin A, folic acid, or a cationic dye (e.g., Cy3).

5) Tethered Ligands

Other entities can be tethered to a compound of the invention. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are preferably located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, preferably covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of an RNA silencing agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g., cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFα), interleukin-1 beta, or gamma interferon. In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a preferred embodiment, the lipid based ligand binds HSA. A lipid-based ligand can bind HSA with a sufficient affinity such that the conjugate will be preferably distributed to a non-kidney tissue. However, it is preferred that the affinity not be so strong that the HSA-ligand binding cannot be reversed. In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized

EXAMPLES

Example 1

Chemical Synthesis of Di-siRNAs and Vitamin D Conjugated hsiRNAs

Figure 2:
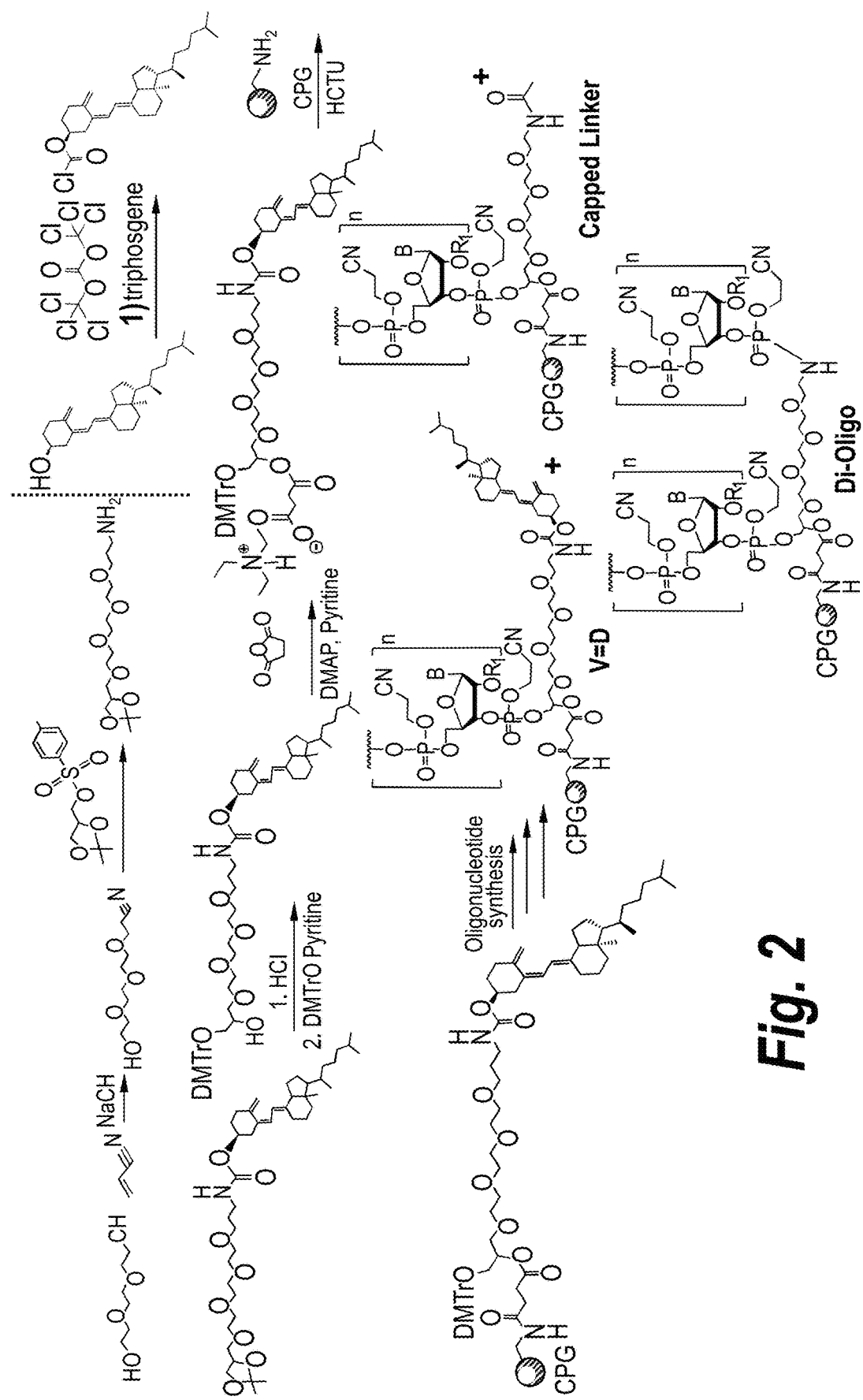
FIG. 2 shows a chemical synthesis, purification and QC of Di-branched siRNAs.

The Di-siRNAs used in the in vitro and in vivo efficacy evaluation were synthesized as follows. As shown in FIG. 2, triethylene glycol was reacted with acrylonitrile to introduce protected amine functionality. A branch point was then added as a tosylated solketal, followed by reduction of the nitrile to yield a primary amine which was then attached to vitamin D (calciferol) through a carbamate linker. The ketal was then hydrolyzed to release the cis-diol which was selectively protected at the primary hydroxyl with dimethoxytrityl (DMTr) protecting group, followed by succinylation with succinic anhydride. The resulting moiety was attached to a solid support followed by solid phase oligonucleotide synthesis and deprotection resulting in the three products shown; VitD, Capped linker, and Di-siRNA. The products of synthesis were then analyzed as described in Example 4.

Example 2

Alternative Synthesis Route 1

Figure 5:
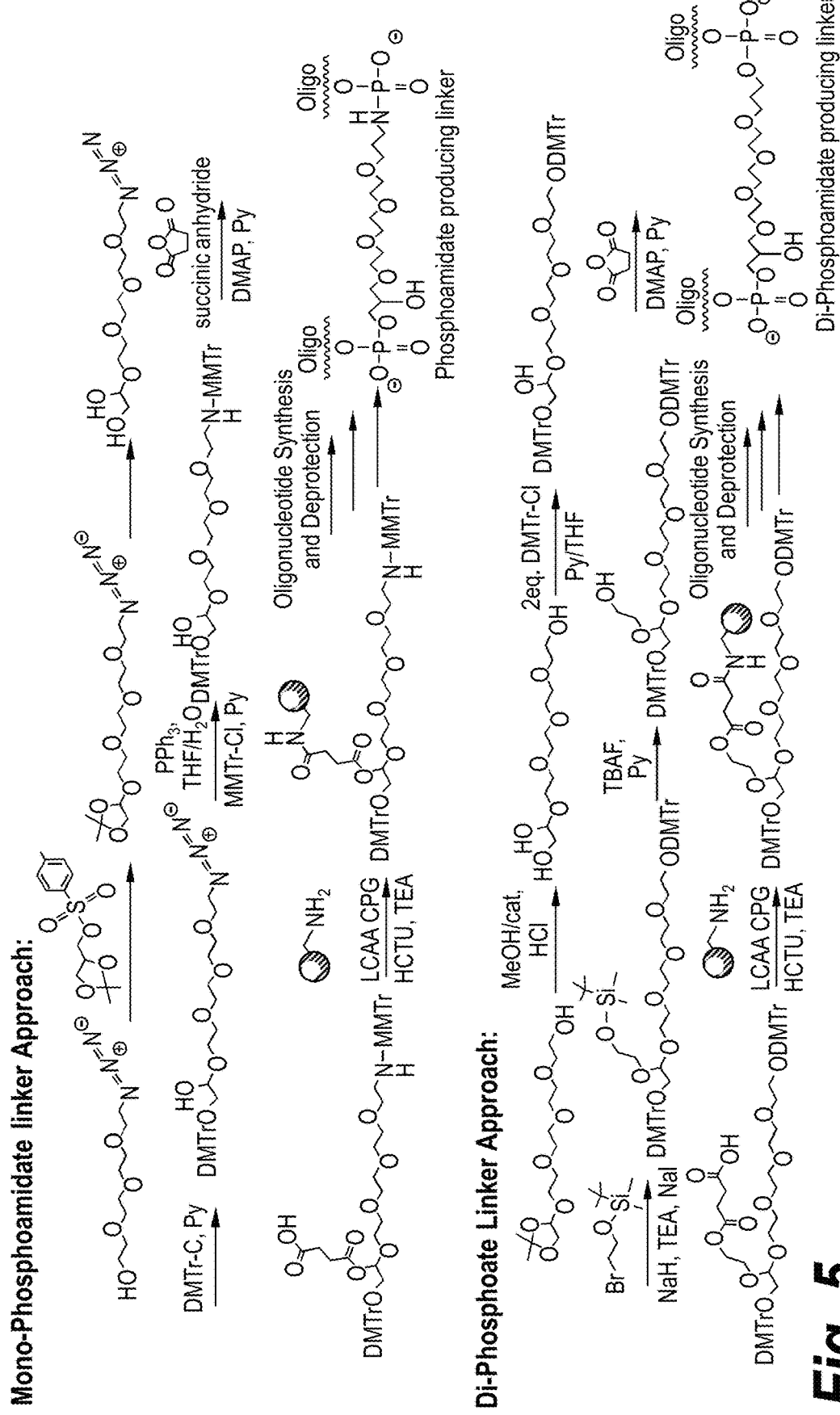
FIG. 5 shows a synthesis of a branched oligonucleotide using alternative chemical routes.

As shown in FIG. 5, the mono-phosphoamidate linker approach involves the following steps: Mono-azide tetraethylene glycol has a branch point added as a tosylated solketal. The ketal is then removed to release the cis-diol which is selectively protected at the primary hydroxyl with dimethoxytrityl (DMTr) protecting group, followed by reduction of the azide by triphenylphosphine to a primary amine, which is immediately protected with a monomethoxy trityl (MMTr) protecting group. The remaining hydroxyl is succinylated with succinic anhydride and coupled to solid support (LCAA CPG). Oligonucleotide synthesis and deprotection affords one main product the, the di-siRNA with a phosphate and phosphoamidate linkage. This example highlights an alternative and direct route of synthesis to produce solely the phosphate and phosphoamidate linker.

Example 3

Alternative Synthesis Route 2

In order to produce a di-phosphate containing moiety, a second alternative synthesis approach was developed. As shown in FIG. 5, the di-phosphoate linker approach involves the following steps: Starting from a solketal-modified teraethylene glycol, the ketal is removed and the two primary hydroxyls are selectively protected with dimethoxy trityl (DMTr). The remaining hydroxyl is extended in length with a silyl protected 1-bromoethanol. The TBDMS is removed, succinylated and attached to solid support. This is followed by solid phase oligonucleotide synthesis and deprotection, producing the Di-siRNA with the diphosphate containing linker.

Example 4

Quality Control of Chemical Synthesis of Di-siRNAs and Vitamin D Conjugated hsiRNAs

HPLC

Figure 3:
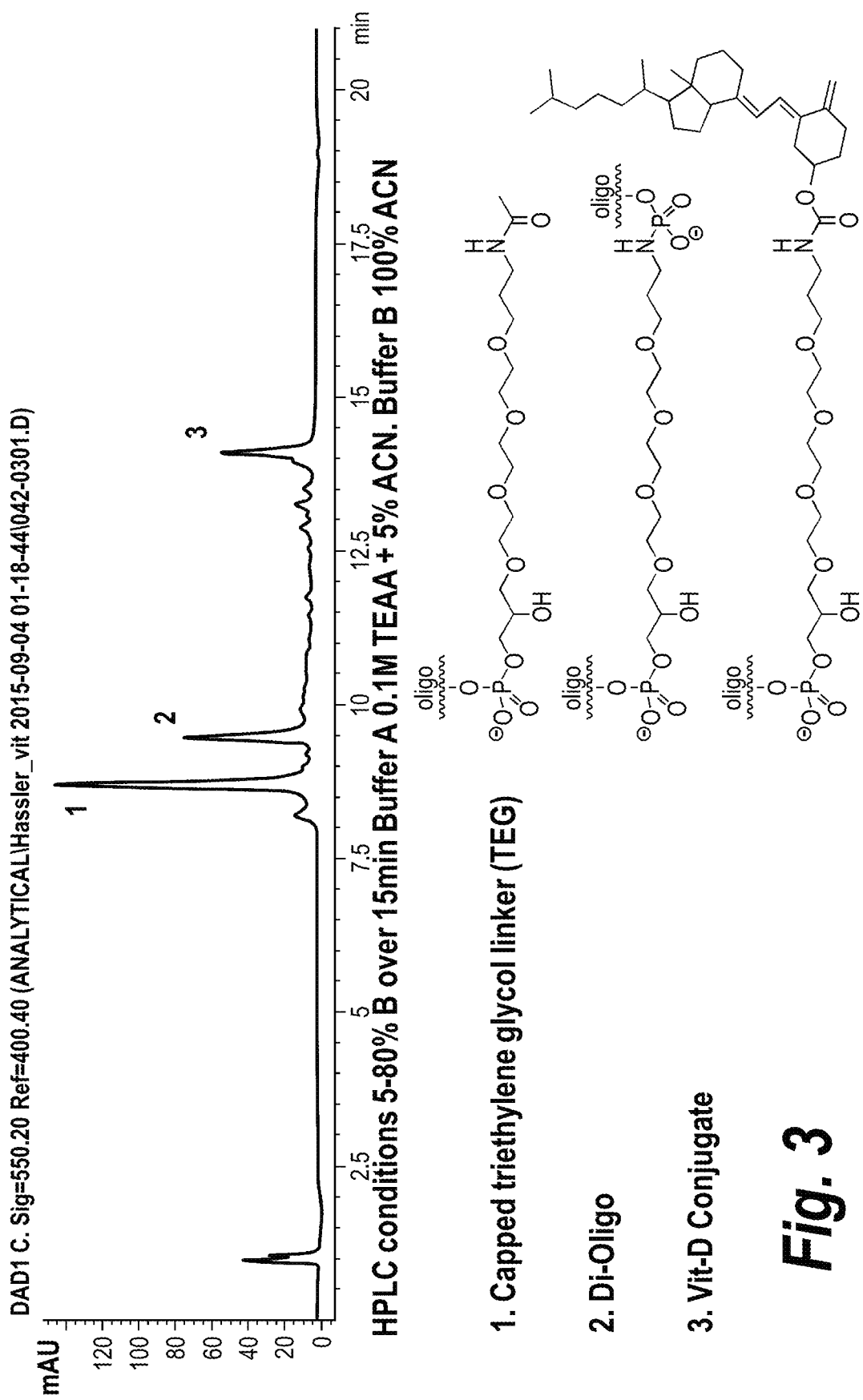
FIG. 3 shows HPLC and QC of compounds produced by the method depicted in FIG. 2. Three major products were identified by mass spectrometry as sense strand with TEG (tetraethylene glycol) linker, di-branched oligo and Vit-D (calciferol) conjugate. All products where purified by HPLC and tested in vivo independently. Only Di branched oligo is characterized by unprecedented tissue distribution and efficacy, indicating that branching structure is essential for tissue retention and distribution.

To assess the quality of the chemical synthesis of Di-siRNAs and Vitamin D conjugated hsiRNAs, analytical HPLC was used to identify and quantify the synthesized products. Three major products were identified: the siRNA sense strand capped with a tryethylene glycol (TEG) linker, the Di-siRNA, and the vitamin D conjugated siRNA sense strand (FIG. 3). Each product was isolated by HPLC and used for subsequent experiments. The chemical structures of the three major products of synthesis are shown in FIG. 3. The conditions for HPLC included: 5-80% B over 15 minutes, Buffer A (0.1 M TEAA+5% ACN), Buffer B (100% ACN).

Mass Spectrometry

Figure 4:
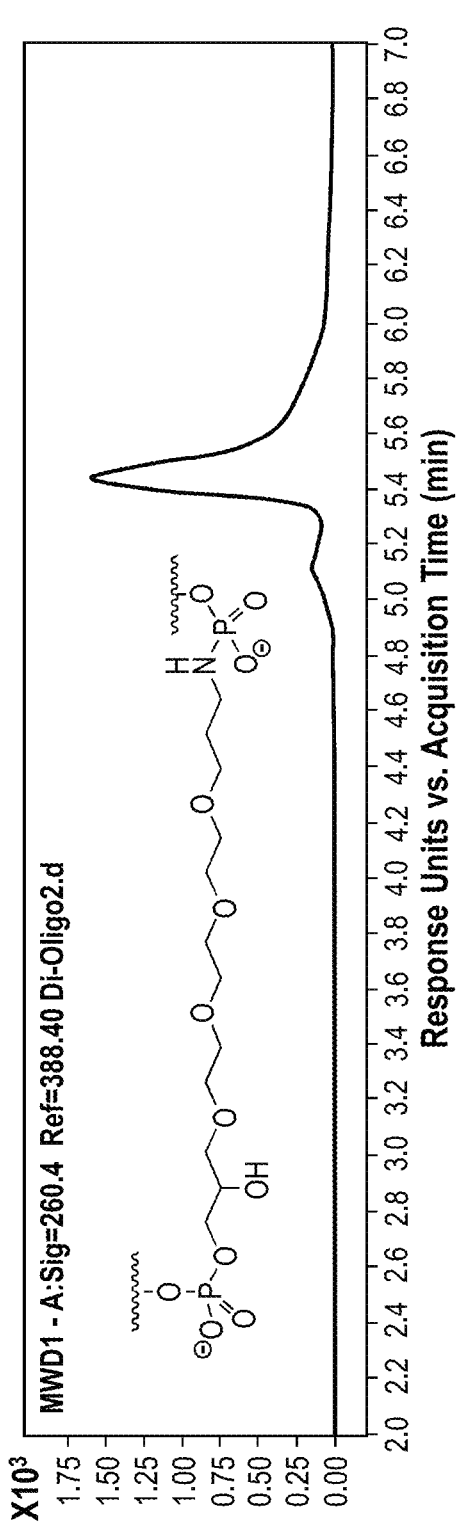
FIG. 4 shows mass spectrometry confirming the mass of the Di-branched oligonucleotide. The observed mass of 11683 corresponds to two sense strands attached through the TEG linker by the 3' ends.
Figure 4:
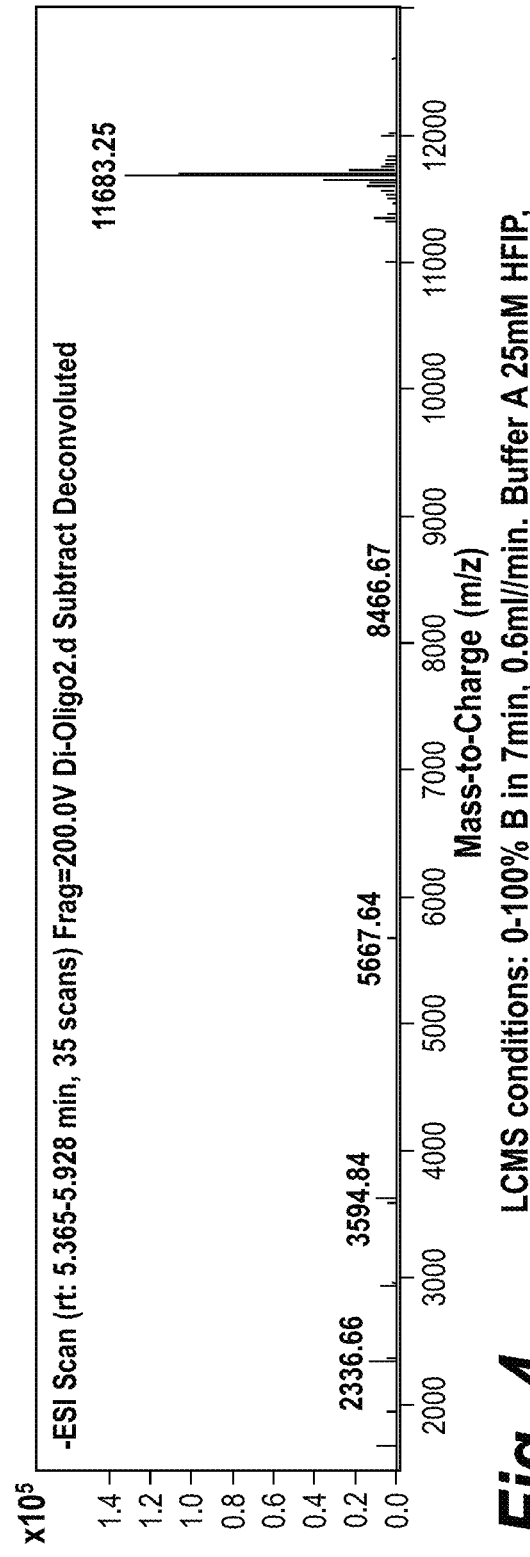

Further quality control was done by mass spectrometry, which confirmed the identity of the Di-siRNA complex. The product was observed to have a mass of 11683 m/z, which corresponds to two sense strands of the siRNA attached at the 3' ends through the TEG linker (FIG. 4). In this specific example the siRNA sense strand was designed to target the Huntingtin gene (Htt). The method of chemical synthesis outlined in Example 1 successfully produced the desired product of a Di-branched siRNA complex targeting the Huntingtin gene. LC-MS conditions included: 0-100% B over 7 minutes, 0.6 mL/min. Buffer A (25 mM HFIP, 15 mM DBA in 20% MeOH), Buffer B (MeOH with 20% Buffer A).

Example 5

Figure 22A:
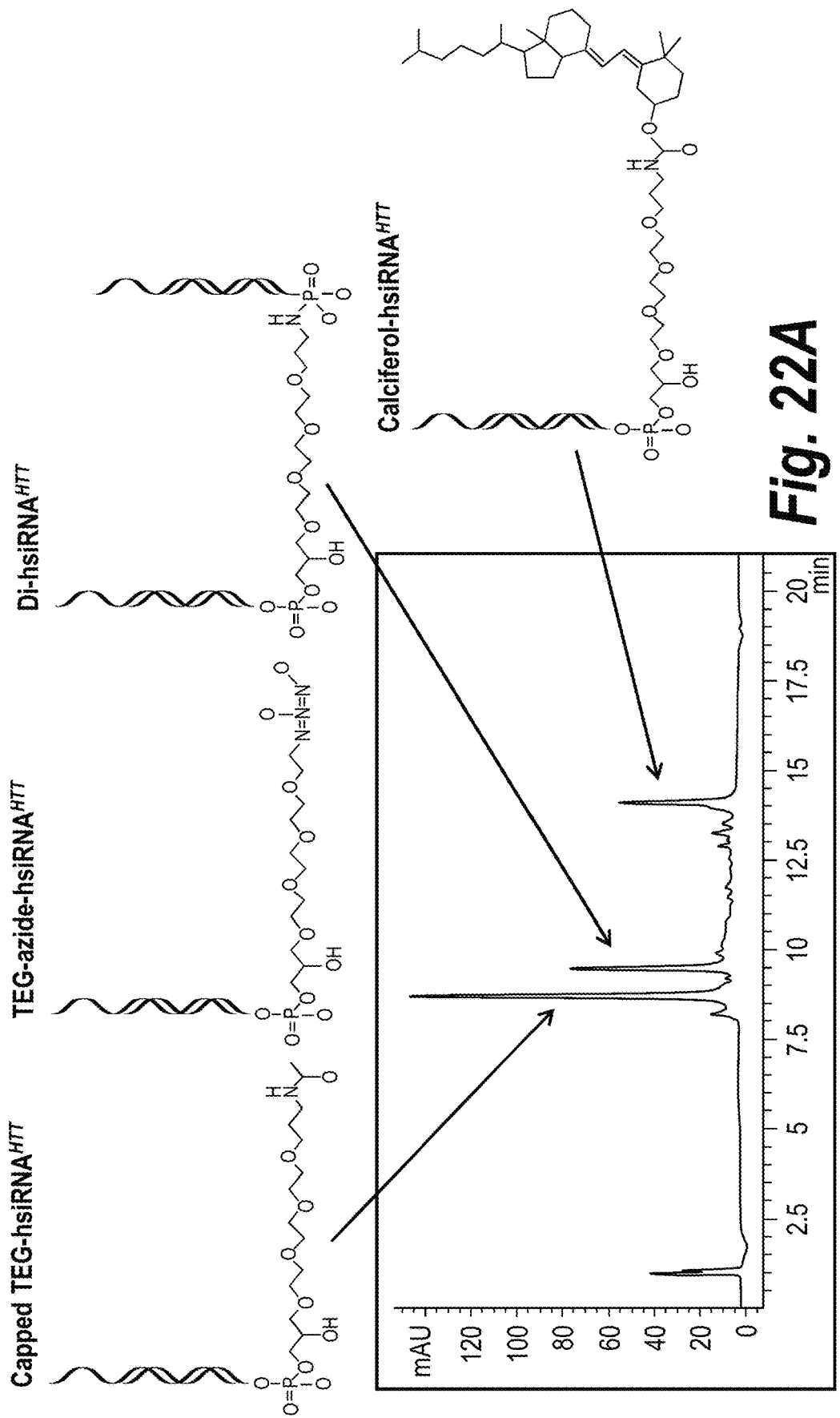
FIGS. 22A-22C depict Di-FM-hsiRNA.
Figure 22B:
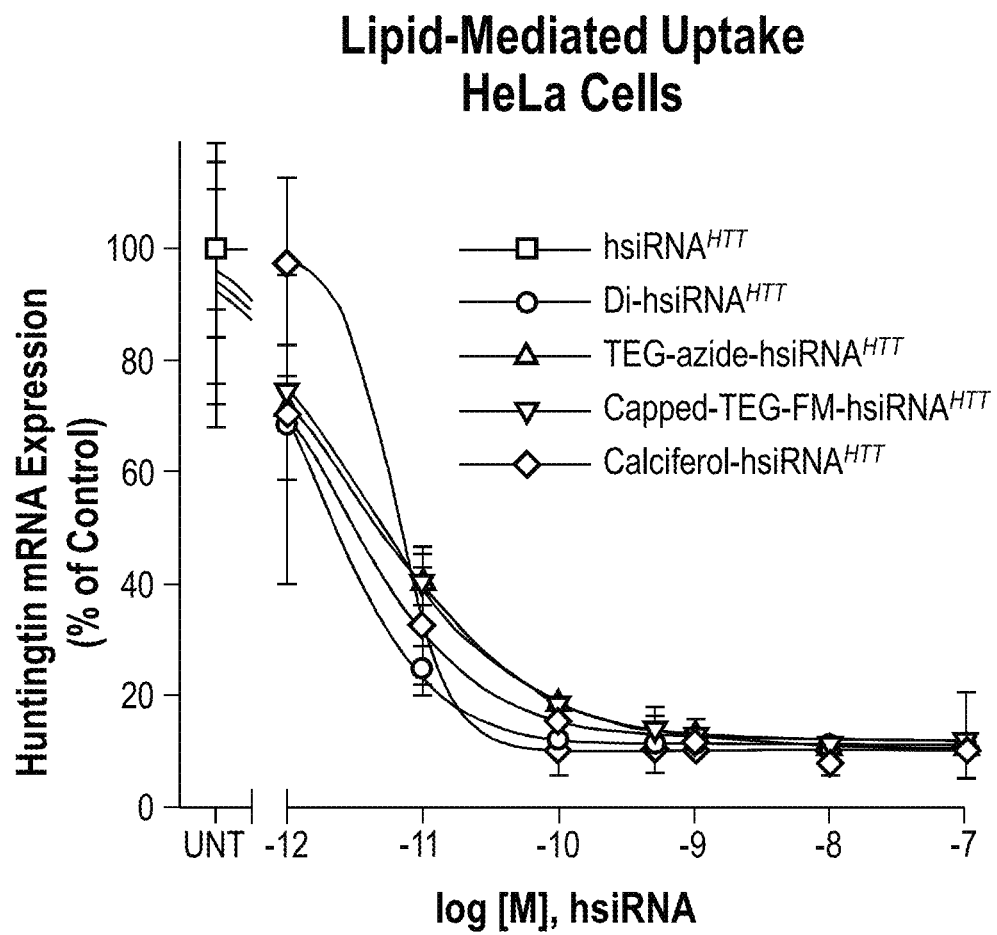
Figure 22C:
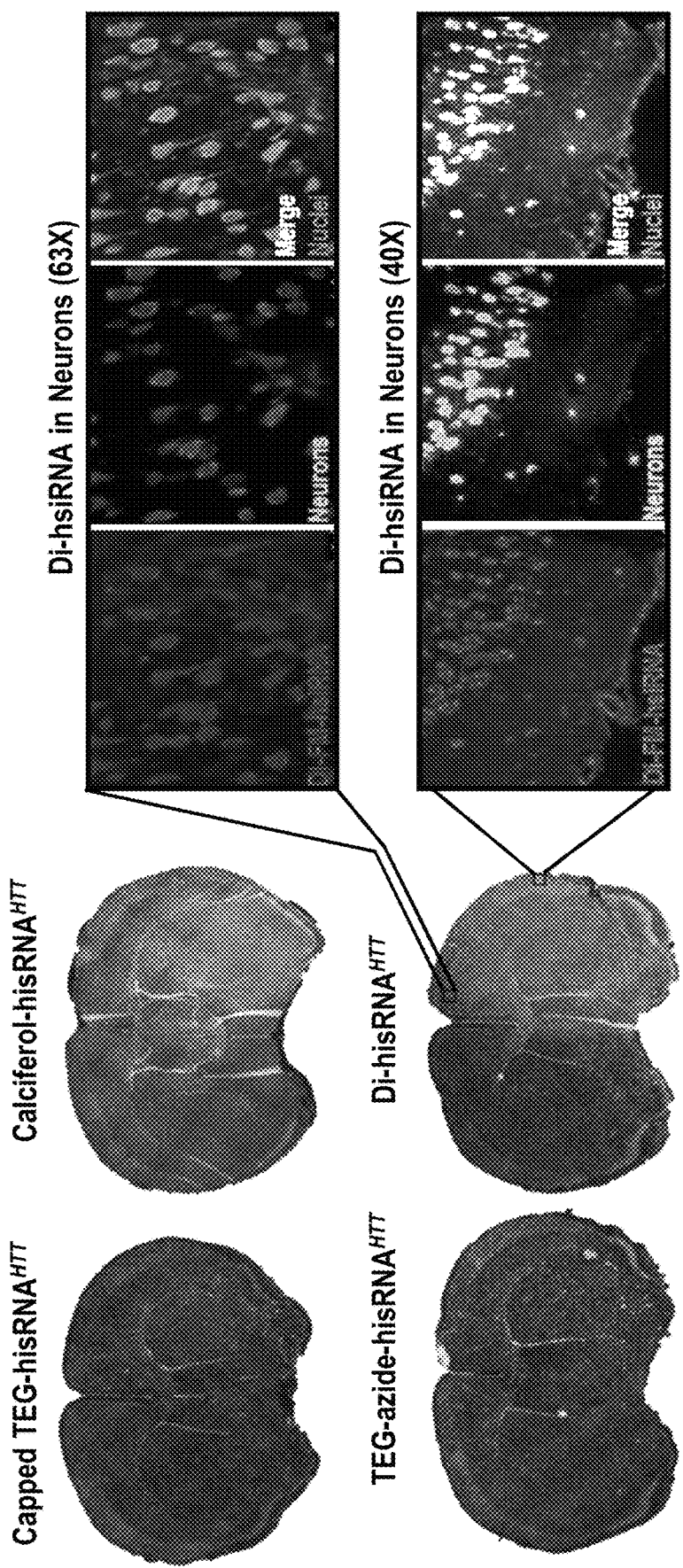

Efficacy and Cellular Uptake of By-products of Chemical Synthesis of Di-siRNAs and Vitamin D Conjugated hsiRNAs To assess the Htt gene silencing efficacy of each HPLC-isolated by-product of the chemical synthesis of Di-siRNAs and Vitamin D conjugated hsiRNAs, HeLa cells were treated with each isolated product by lipid-mediated transfection. Huntingtin mRNA expression was assessed through Affymetrix Quantigene 2.0 and normalized to a housekeeping gene (PPIB). All four by-products resulted in significant Htt gene silencing 72 hours post transfection (FIG. 22). Cellular uptake was tested in vivo by delivering each fluorescently labeled by-product to mice via instrastriatal injection and measuring the uptake by fluorescent imaging. The Di-siRNA product showed dramatically increased uptake in the injected hemisphere of the mouse brain compared to the other three by-products (FIG. 22). Of the four by-products resulting from the chemical synthesis reaction, the Di-siRNA shows both efficient gene-silencing and high levels of cellular uptake in vivo.

Example 6

In Vitro Efficacy of Di-branched siRNA Structure

To determine the in vitro efficacy of Di-branched siRNAs (Di-siRNAs), Di-siRNAs targeting Htt were transfected into HeLa cells using a lipid-mediated delivery system. HeLa cells were transfected with branched oligonucleotides at varying concentrations using RNAiMax. HTT mRNA expression was measured 72 hours after transfection. The Di-siRNAs caused significant silencing of the HTT gene, similar to the effect resulting from single siRNA duplex in HeLa cells (FIG. 10).

To determine efficiency of cellular uptake and gene silencing in primary cortical neurons without lipid mediated delivery, cells were treated passively with Htt-Di-siRNAs at varying concentrations for one week. HTT mRNA expression was measured and normalized to the housekeeping gene PPIB. As shown in FIG. 10, the Di-siRNA structure led to significant silencing of the Htt gene, showing that the Di-branched siRNA structure is efficiently delivered to neurons without the lipid formulation. This demonstrates that the Di-branched structure of the siRNA complex does not hinder RISC loading and the gene silencing effects of known effective siRNAs.

Example 7

Route of Administration of Di-siRNAs and Vitamin D Conjugated hsiRNAs

Figure 27A:
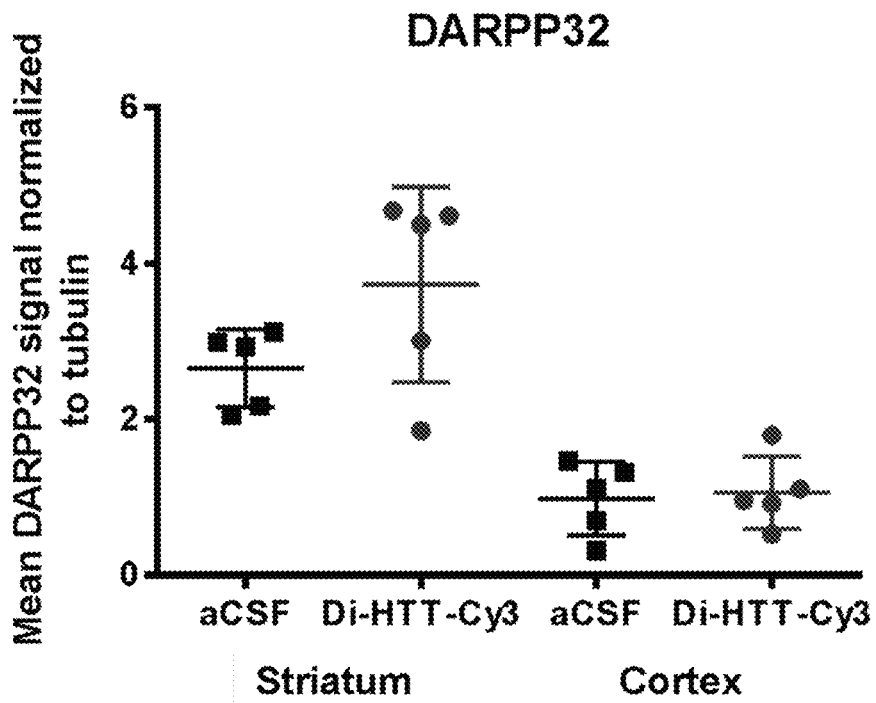
FIGS. 27A-27B show that high dose Di-HTT-Cy3 treatment does not cause significant toxicity in vivo but does lead to significant gliosis in vivo two weeks post intrastriatal injection.
Figure 27B:
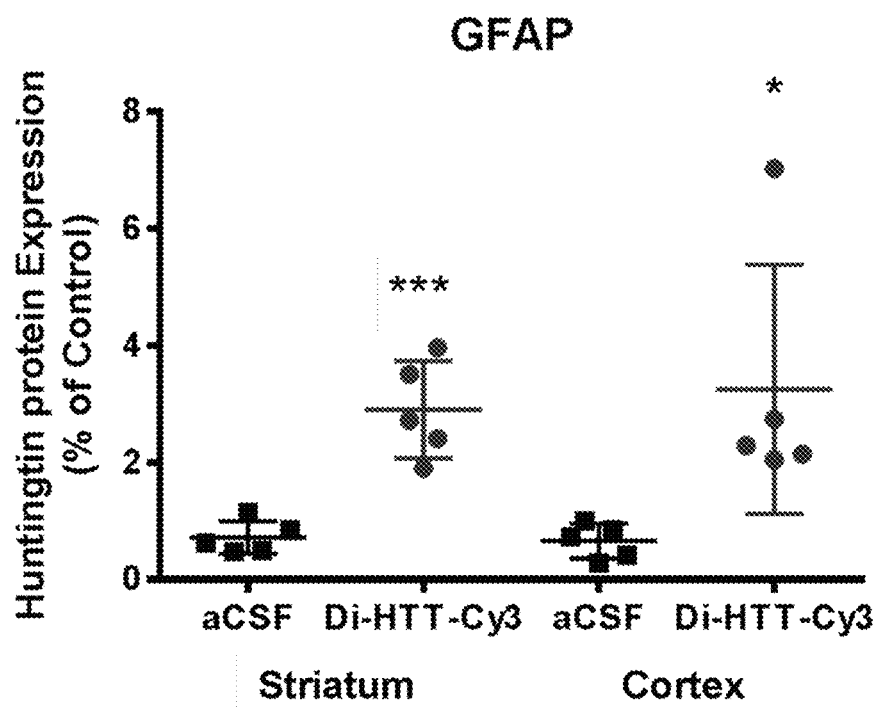

To assess the efficacy of delivery and activity of branched oligonucleotides in vivo in neurons, Di-HTT-Cy3 was delivered to mice via intrastriatal (IS) injection. Di-HTT-Cy3 localized to and accumulated throughout the injected hemisphere of the brain, whereas the single branch HTT-siRNA (tryethylene glycol conjugated siRNA (TEG-siRNA))

showed significantly lower accumulation in the injected hemisphere of the brain (FIG. 11). A single IS injection of Htt-Di-siRNA resulted in significant gene silencing one week post injection (FIG. 13) and the level of gene silencing was maintained two weeks post injection (FIG. 26). Further experiments showed that a single IS injection of Di-HTT-Cy3 did not result in significant toxicity two weeks post injection (FIG. 27A). However, the Htt-Di-siRNAs did cause significant gliosis (FIG. 27B), which is to be expected when the Htt gene is silenced in neurons. Furthermore, the Di-HTT-Cy3 does not accumulate in the liver or kidney two weeks post IS injection (FIG. 13), nor is the Htt mRNA significantly silenced in the liver or kidney following IS injection (FIG. 23). The double-branch structure of the Di-siRNAs significantly improves distribution and neuronal uptake when compared with the TEG-siRNA only; therefore it is likely that the size and/or the structure of the siRNA complex are important for efficacy. The IS injection of Htt-Di-siRNAs leads to significant and stable depletion of Htt, which stays localized to the brain, this level of efficacy has never been demonstrated for non-conjugated siRNAs.

Example 8

Alternative Route of Administration 1

Figure 28:
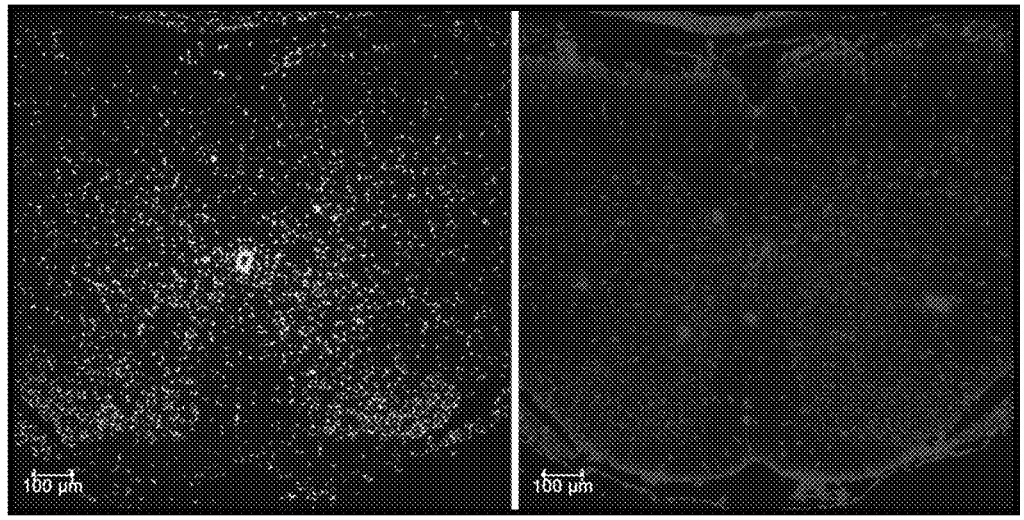
FIG. 28 depicts fluorescent imaging showing that intrathecal injection of Di-HTT-Cy3 results in robust and even distribution throughout the spinal cord.
Figure 28:
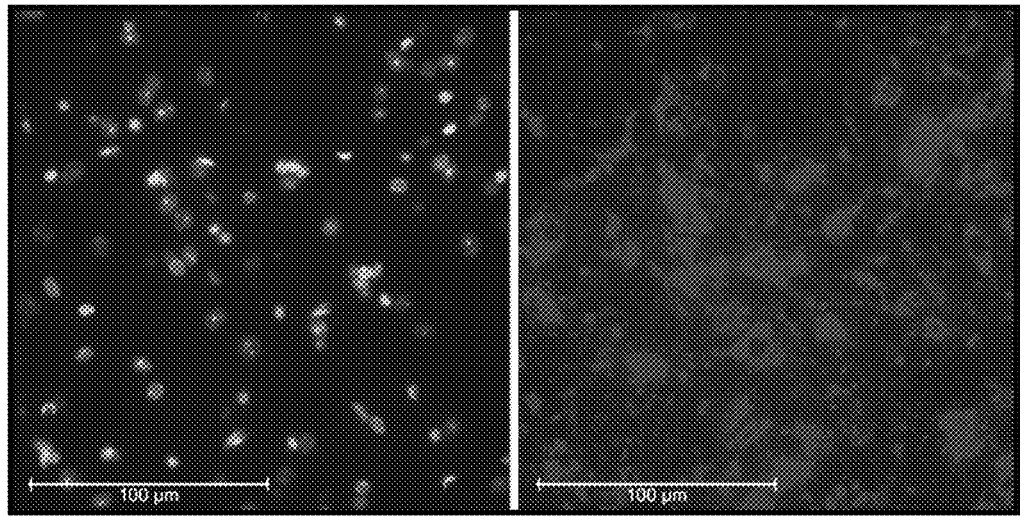
Figure 29:
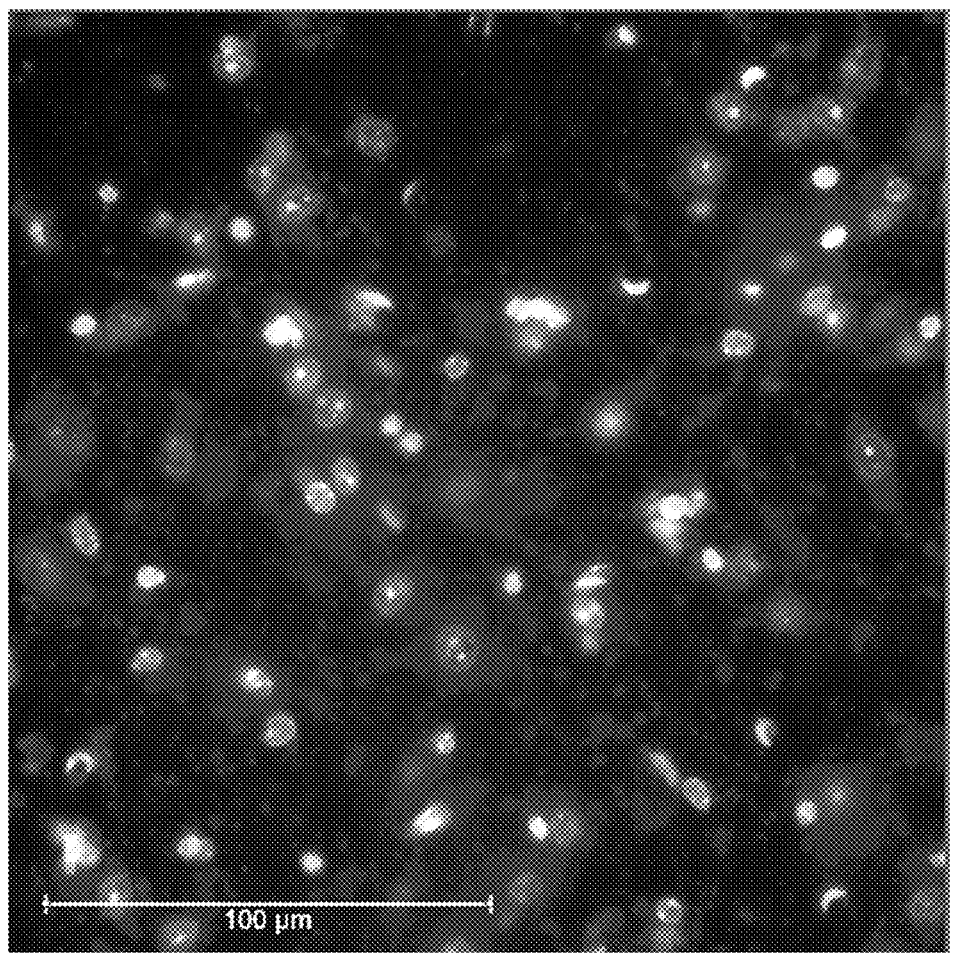
FIG. 29 depicts a merged fluorescent image of FIG. 28B (zoom of spinal cord). Blue-nuclei, red-Di-HTT-Cy3.XXX.

To assess the efficacy of delivery and activity of branched oligonucleotides in the spinal cord, Di-HTT-Cy3 was delivered to mice via intrathecal (IT) injection in the lumbar region of the spinal cord. As shown in FIGS. 14 and 28-29, Di-HTT-Cy3 accumulated in the spinal cord one week post injection. IT injection also led to significant Htt mRNA silencing in the cervical, thoracic, and lumbar regions of the spinal cord one week post injection (FIG. 14). The IT injection of Di-HTT-Cy3 successfully led to significant gene silencing in the spinal cord.

Example 9

Alternative Route of Administration 2

Figure 30A:
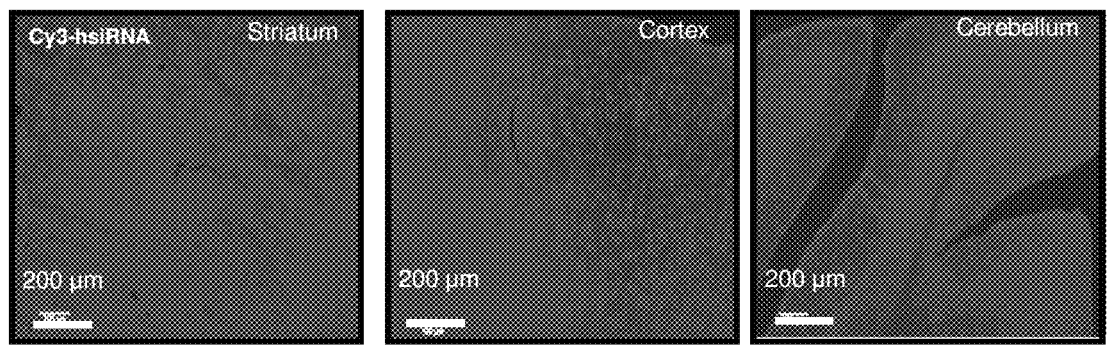
FIGS. 30A-30C show the widespread distribution of Di-HTT-Cy3 48 hours post intracerebroventricular injection.
Figure 30B:
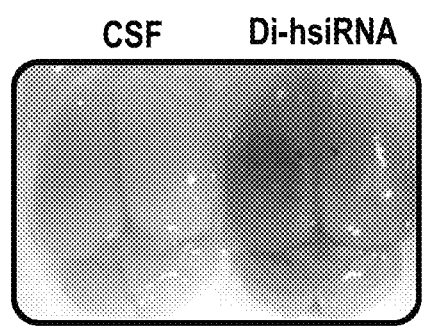
Figure 30C:
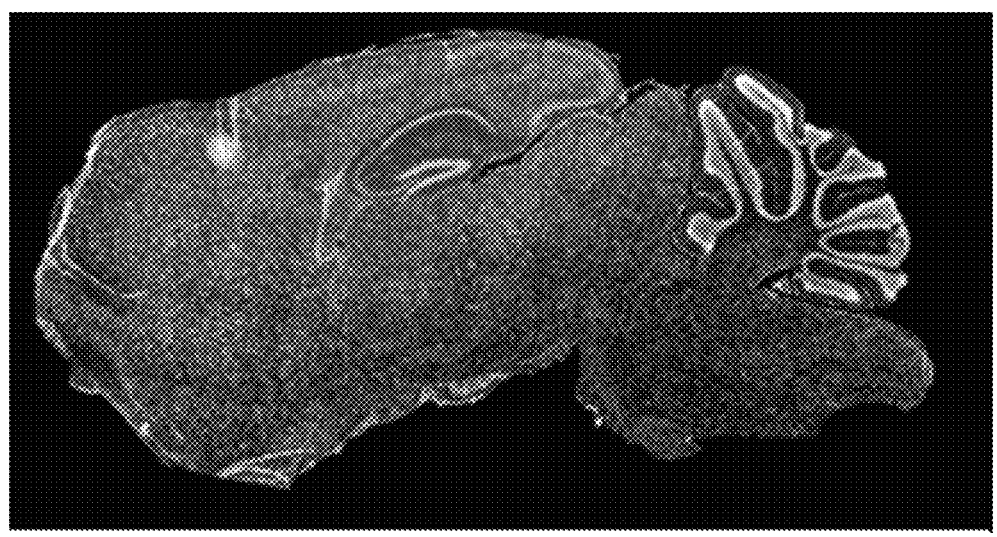

To assess the efficacy of delivery and activity of branched oligonucleotides throughout the brain in a clinically relevant experiment, Di-HTT-Cy3 was delivered to mice via intracerebroventricular (ICV) injection. The Di-siRNAs accumulated throughout the brain at both two days and two weeks post injection (FIGS. 30-31). ICV injection of Di-HTT-Cy3 also significantly silenced Htt mRNA and protein expression two weeks post injection (FIG. 32). Further experiments showed the ICV delivery did not result in significant toxicity two weeks post injection (FIG. 33). However, ICV injection of Di-HTT-Cy3 did result in significant gliosis in multiple areas of the brain, which is an expected result upon silencing of the Htt gene (FIG. 34). The ICV injection directly administers the Di-siRNAs to the cerebrospinal fluid (CSF) in order to bypass the blood brain barrier and this injection is used to treat diseases of the brain.

This result is important for the therapeutic potential of branched oligonucleotides, as ICV injection is a therapeutically relevant injection for neurological diseases. The efficacy and stability of the branched oligonucleotides following ICV administration demonstrates that the invention described herein could be utilized as therapy in a variety of hard to treat neurological diseases, including Huntington's disease.

Example 10

Alternative Route of Administration 3

Figure 35:
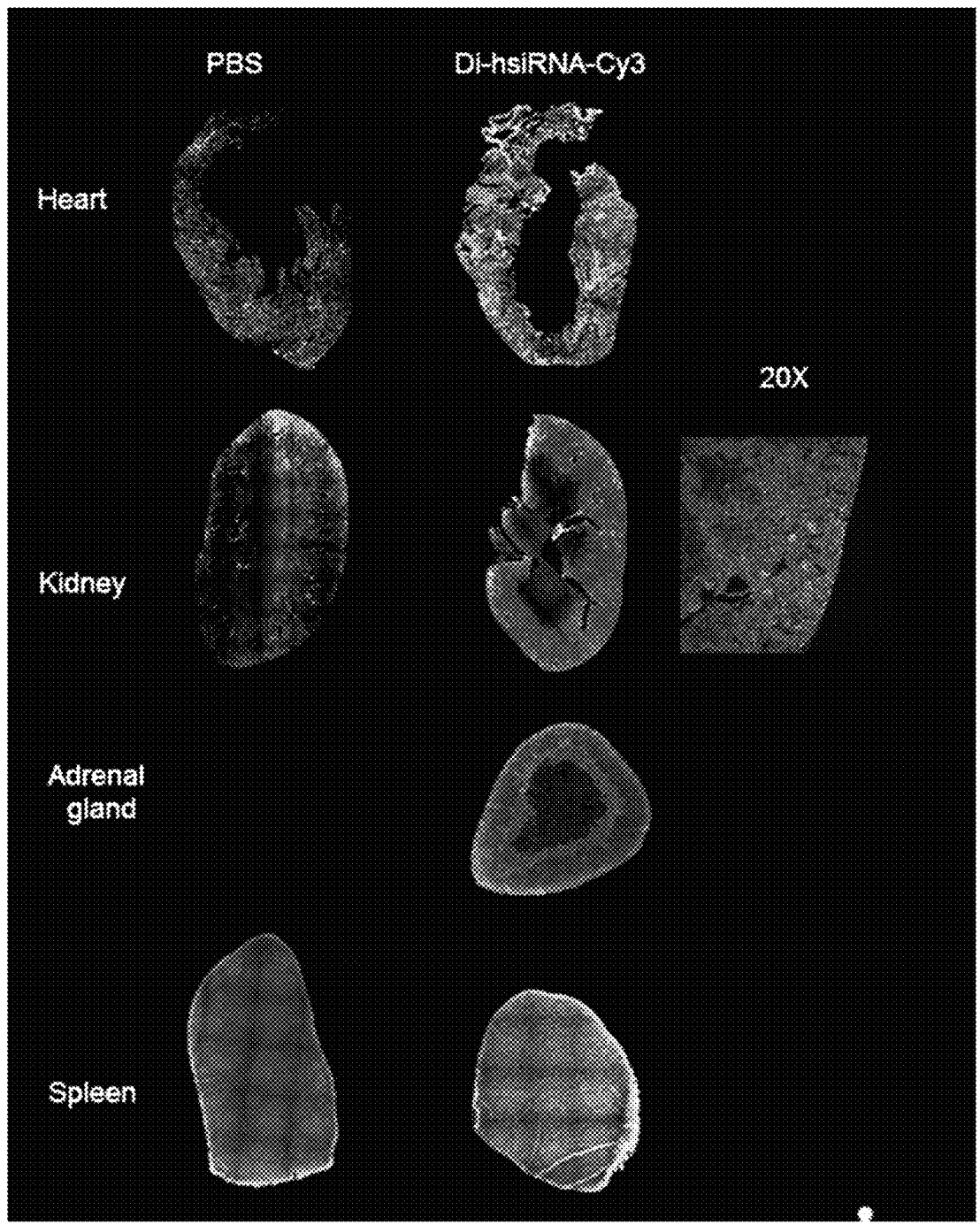
FIG. 35 shows that Di-HTT-Cy3 is distributed to multiple organs following intravenous injection. Fluorescent images depict Di-HTT-Cy3 levels in the heart, kidney, adrenal gland, and spleen following intravenous injection of Di-HTT-Cy3 or a negative control (PBS).
Figure 36:
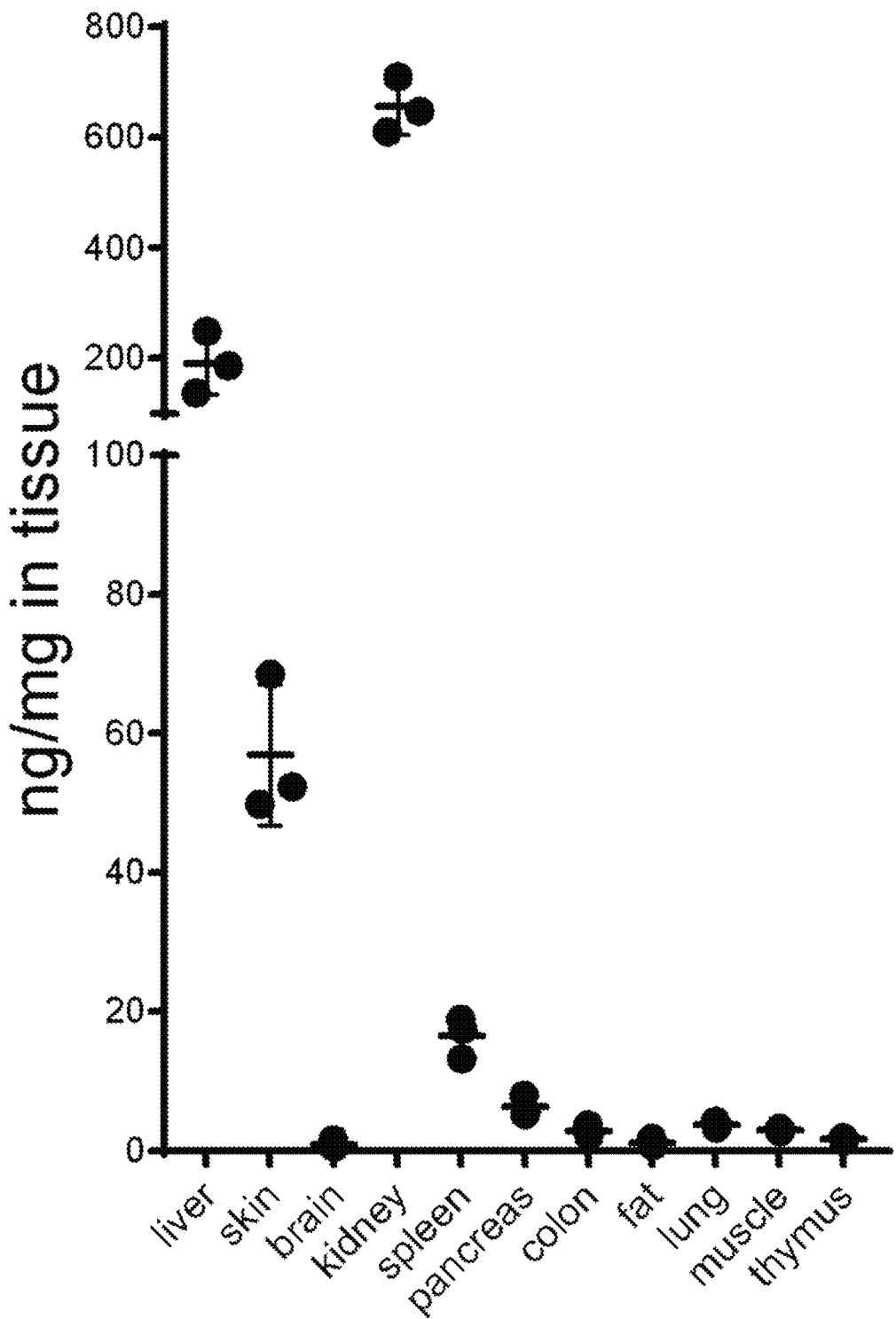
FIG. 36 shows that Di-HTT-Cy3 accumulates in multiple organs following intravenous injection. A scatter dot plot measures the levels of Di-HTT-Cy3 in multiple tissues.

To assess the efficacy of delivery and activity of Di-siRNAs throughout the body, Di-HTT-Cy3 was administered to mice via intravenous (IV) injection. The mice were injected with 20 mg/kg Di-HTT-Cy3 and two consecutive days (total of 40 mg/kg) and were sacrificed 24 hours after the final injection. As shown in FIGS. 35-36, the Di-siRNAs accumulated in multiple organs (including liver, kidney, spleen, pancreas, lung, fat, muscle, thymus, colon, and skin) following IV delivery. The Di-siRNAs also accumulated in the brain, demonstrating the ability of the Di-siRNAs to cross the blood-brain barrier, an unprecedented result using therapeutic siRNAs. The IV injection demonstrates that the Di-siRNA structure is effective and functional in a wide variety of cell types throughout the body.

Example 11

Determination of Toxicity and Gliosis

Toxicity

In order to assess the level of toxicity in the brain following injection of Di-HTT-Cy3, protein levels of DARPP32 were assessed in brain tissue because elevated DARPP32 indicates neuronal death (Jin, H., et al. *DARPP-32 to quantify intracerebral hemorrhage-induced neuronal death in basal ganglia*. Transl Stroke Res. 4(1): 130-134. 2013). Mice were treated with 2 nmols Di-HTT-Cy3 (4 nmols of corresponding antisense HTT strand) via IS or ICV injection. The animals were sacrificed 14 days after injection and tissue punches were taken from 300 µm brain slices from different areas of the brain. DARPP32 protein was quantified by immunoblot. Artificial cerebrospinal fluid (aCSF) was used as a negative control. Neither IS nor ICV injection of high dose Di-HTT-Cy3 resulted in significant toxicity (FIGS. 27 and 33).

Gliosis

In order to assess the level of gliosis in the brain following injection of Di-HTT-Cy3, GFAP protein levels were assessed following high dose of Di-HTT-Cy3. Mice were treated with 2 nmols Di-HTT-Cy3 (4 nmols of corresponding antisense HTT strand) via IS or ICV injection. The animals were sacrificed 14 days after injection and tissue punches were taken from 300 µm brain slices from different areas of the brain. GFAP protein was quantified by immunoblot. Artificial cerebrospinal fluid (aCSF) was used as a negative control. Artificial cerebrospinal fluid (aCSF) was used as a negative control. Both IS and ICV injection of high dose Di-HTT-Cy3 resulted in significant gliosis (FIGS. 27 and 34), however induction of gliosis is an expected result upon near complete silencing of the Huntingtin gene.

Example 12

Determination of Di-HTT-Cy3 Efficacy In Vivo

Distribution and Accumulation

In order to determine the efficacy of distribution of branched oligonucleotides in vivo, mice were treated with Di-HTT-Cy3 via IS, ICV, intrathecal, or IV injections as described above in Examples 7-10. In all Examples, 2 nmols Di-HTT-Cy3 (4 nmols of corresponding antisense HTT strand) was injected and accumulation was quantified by using Cy3-labeled peptide nucleic acids (PNAs) to hybridize to the sense strand. HPLC analysis was then used to quantify ng of Di-HTT-Cy3 per mg of tissue. Artificial cerebrospinal fluid (aCSF) was used as a negative control.

In fluorescent imaging experiments, brain slices were stained with DAPI (blue) imaged using the Cy3 channel to detect accumulation of Di-HTT-Cy3 (red).

Silencing

In order to determine the efficacy of silencing of branched oligonucleotides in vivo, mice were treated with Di-HTT-Cy3 via IS, ICV, intrathecal, or IV injections as described above in Examples 7-10. In all examples, 2 nmols Di-HTT-Cy3 (4 nmols of corresponding antisense HTT strand) was injected and silencing of Htt mRNA was quantified using Affymetrix Quantigene 2.0 as described in Coles, A. et al., *A High-Throughput Method for Direct Detection of Therapeutic Oligonucleotide-Induced Gene Silencing In Vivo*. Nucl Acid Ther. 26 (2), 86-92, 2015. Data was normalized to the housekeeping control, HPRT and artificial cerebrospinal fluid (aCSF) was used as a negative control.

Example 13

Incorporation of a Hydrophobic Moiety in the Branched Oligonucleotide Structure: Strategy 1

Figure 44:
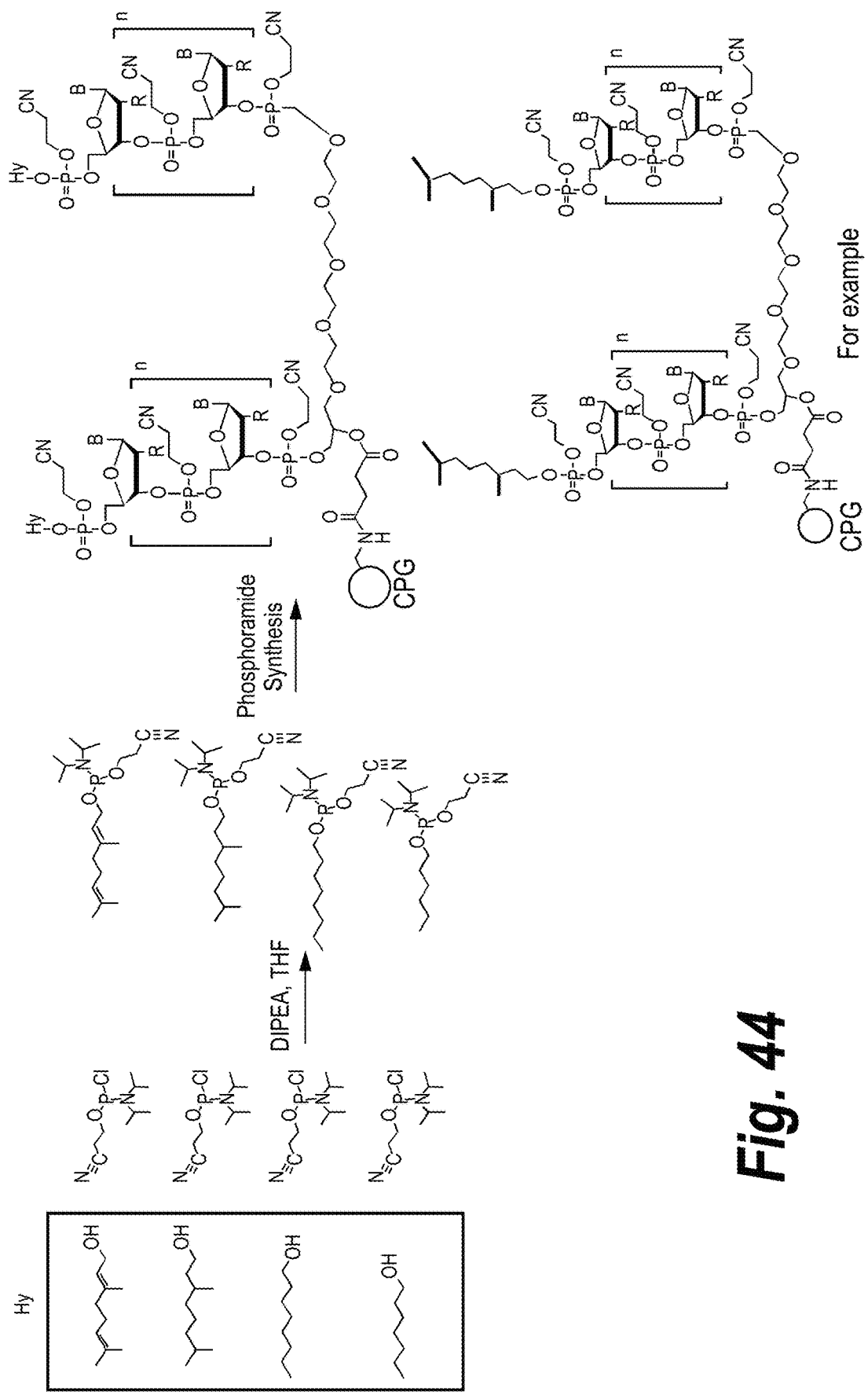
FIG. 44 depicts a first strategy for the incorporation of a hydrophobic moeity into the branched oligonucleotide structures.

In one example, a short hydrophobic alkylene or alkane (Hy) with an unprotected hydroxyl group (or amine) that can be phosphitylated with 2-Cyanoethoxy-bis(N,N-diisopropylamino)phosphine (or any other suitable phosphitylating reagent) is used to produce the corresponding lipophilic phosphoramidite. These lipophilic phosphoramidites can be added to the terminal position of the branched oligonucleotide using conventional oligonucleotide synthesis conditions. This strategy is depicted in FIG. 44.

Example 14

Incorporation of a Hydrophobic Moeity in the Branched Oligonucleotide Structure: Strategy 2

Figure 45:
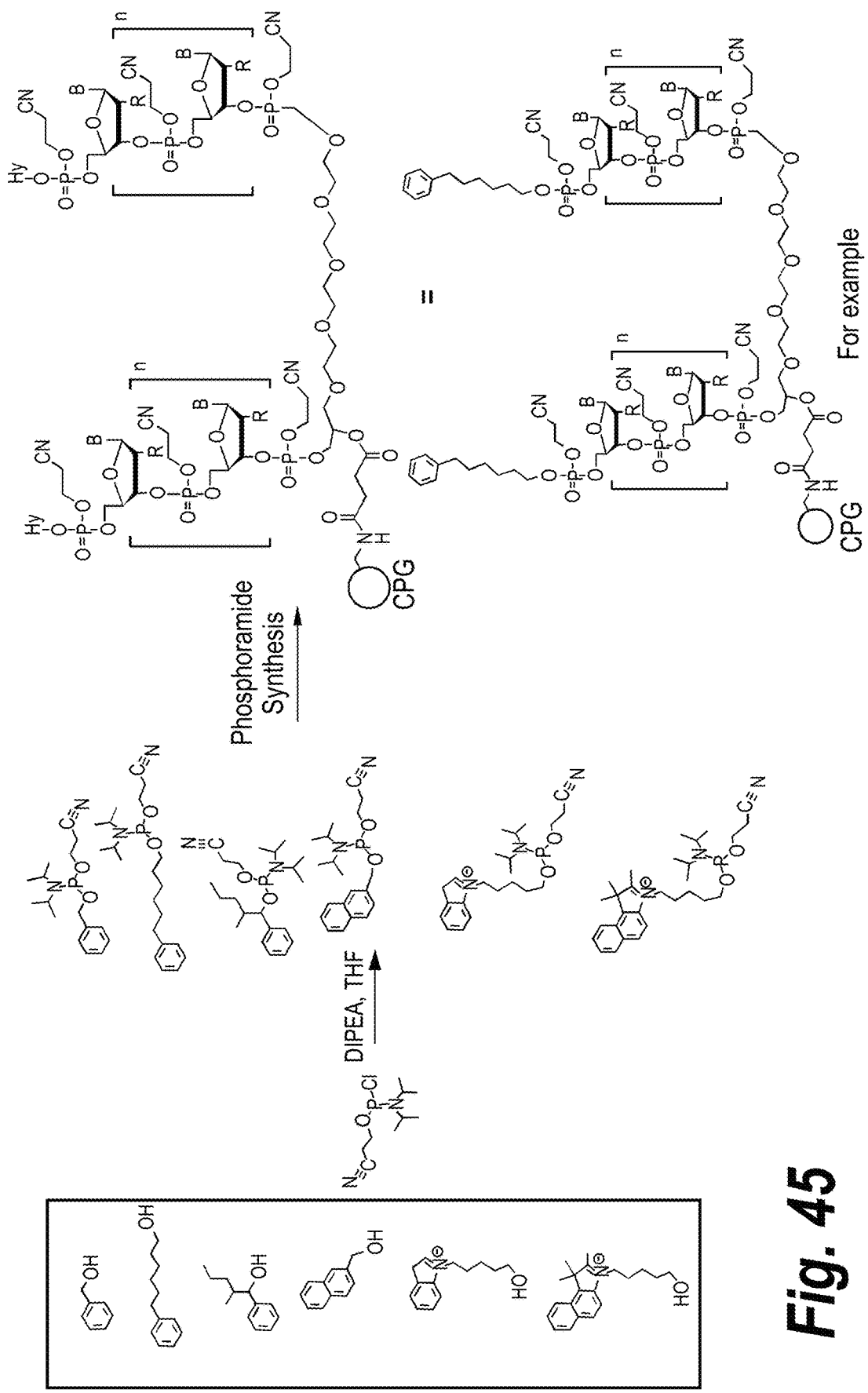
FIG. 45 depicts a second strategy for the incorporation of a hydrophobic moeity into the branched oligonucleotide structures.

In another example, a short/small aromatic planar molecule (Hy) that has an unprotected hydroxyl group with or without a positive charge (or amine) that can be phosphitylated with 2-Cyanoethoxy-bis(N,N-diisopropylamino)phosphine (or any other suitable phosphitylating reagent) is used to produce the corresponding aromatic hydrophobic phosphoramidite. The aromatic moiety can have a positive charge. These lipophilic phosphoramidites can be added to the terminal position of the branched oligonucleotide using conventional oligonucleotide synthesis conditions. This strategy is depicted in FIG. 45.

Example 15

Incorporation of a Hydrophobic Moeity in the Branched Oligonucleotide Structure: Strategy 3

Figure 46:
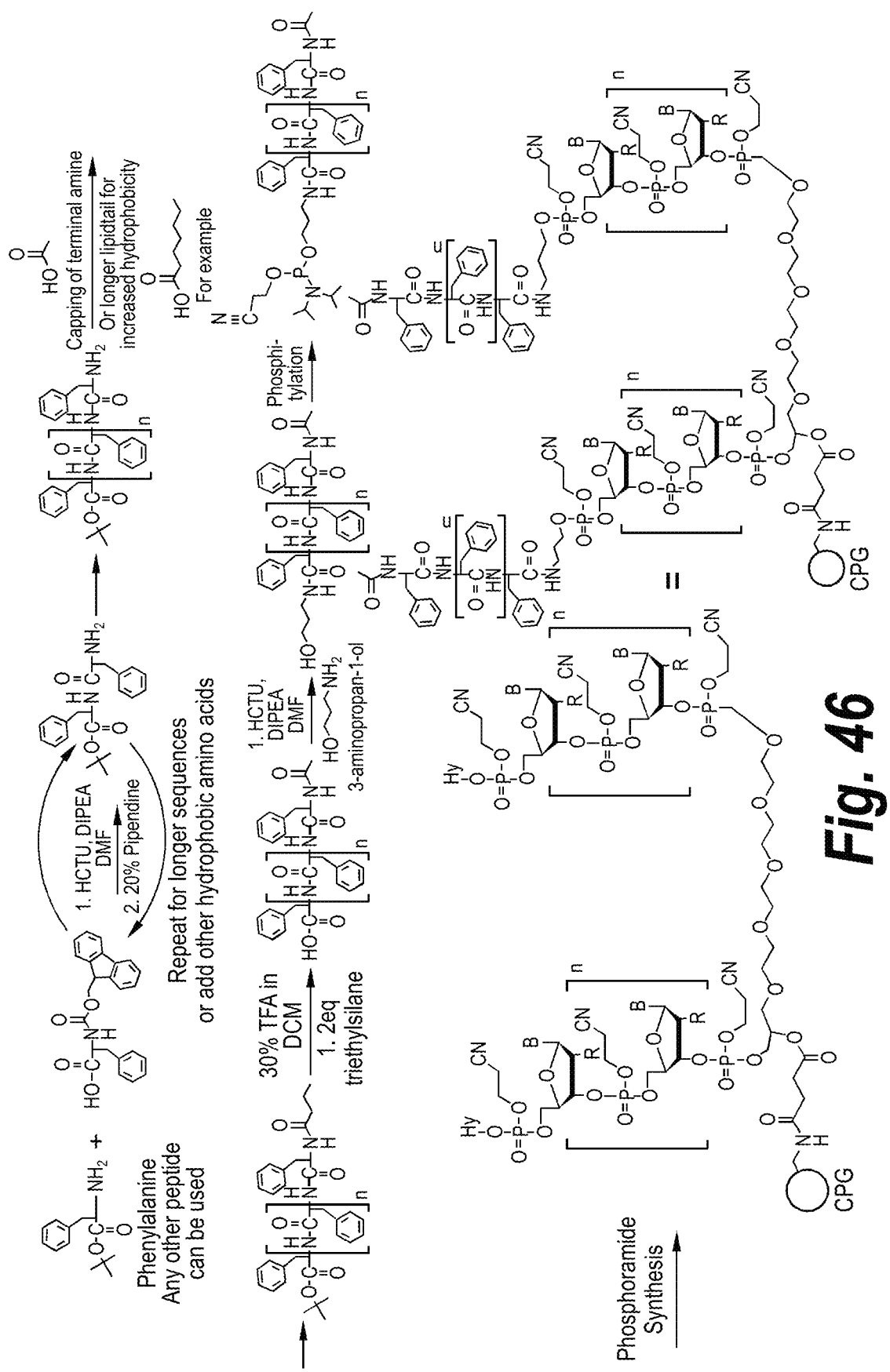
FIG. 46 depicts a third strategy for the incorporation of a hydrophobic moeity into the branched oligonucleotide structures.

To introduce biologically relevant hydrophobic moieties, short lipophilic peptides are made by sequential peptide synthesis either on solid support or in solution (the latter being described here). The short (1-10) amino acid chain can contain positively charged or polar amino acid moieties as well, as any positive charge will reduce the overall net charge of the oligonucleotide, therefore increasing the hydrophobicity. Once the peptide of appropriate length is made it should be capped with acetic anhydride or another short aliphatic acid to increase hydrophobicity and mask the free amine. The carbonyl protecting group is then removed to allow for 3-aminopropan-1-ol to be coupled allowing a free hydroxyl (or amine) to be phosphitylated. This amino acid phosphoramidite can then be added to the terminal 5' position of the branched oligonucleotide using conventional oligonucleotide synthesis conditions. This strategy is depicted in FIG. 46.

The invention claimed is:

1. A method of delivering double-stranded nucleic acids to one or both of the brain and spinal cord of a patient, comprising administering to the patient a branched oligonucleotide compound comprising two siRNA duplexes connected to one another by a linker,
wherein each siRNA duplex comprises a sense strand of at least 15 contiguous nucleotides and an antisense strand of at least 15 contiguous nucleotides having complementarity to the sense strand,
wherein each sense strand and each antisense strand has a 5' end and a 3' end, and
wherein the branched oligonucleotide compound is administered to the patient by intrastriatal (IS) injection, intrathecal (IT) injection, or intracerebroventricular (ICV) injection, thereby delivering the double-stranded nucleic acids to the brain and/or spinal cord of the patient.

2. The method of claim 1, wherein the branched oligonucleotide compound comprises 5-20 phosphorothioated bonds.

3. The method of claim 1, wherein the nucleotides at positions 1-6 from the 3' end of the antisense strand, or positions 1-7 from the 3' end of the antisense strand, are connected to adjacent nucleotides via phosphorothioate linkages.

4. The method of claim 1, wherein the nucleotides at positions 1 and 2 from the 5' end of the sense and antisense strands are connected to adjacent nucleotides via phosphorothioate linkages.

5. The method of claim 1, wherein each siRNA duplex comprises an unpaired overhang of at least 2 nucleotides.

6. The method of claim 5, wherein the nucleotides of the overhang are connected via phosphorothioate linkages.

7. The method of claim 1, wherein each of the sense and antisense strands comprise >80% chemically-modified nucleotides.

8. The method of claim 1, wherein each strand of the siRNA duplex has a length of 16-20 contiguous nucleotides.

9. The method of claim 1, wherein each sense strand of the siRNA duplex has a length of 16 contiguous nucleotides.

10. The method of claim 1, wherein each antisense strand has a length of 20 contiguous nucleotides.

11. The method of claim 1, wherein the nucleic acid further comprises a hydrophobic moiety attached to a 5'end of at least one of the siRNA duplexes.

12. The method of claim 11, wherein the hydrophobic moiety comprises an alkyl, alkenyl, or aryl moiety; a vitamin or cholesterol derivative; a lipophilic amino acid; or a combination thereof.

13. The method of claim 1, wherein the branched oligonucleotide compound is delivered to the brain of the patient.

14. The method of claim 13, wherein the branched oligonucleotide compound is delivered to one or both of the striatum of the brain and the cortex of the brain.

15. The method of claim 1, wherein the branched oligonucleotide compound is delivered to the cerebrospinal fluid (CSF) of the patient.

16. The method of claim 1, wherein the antisense strand has complementarity to a target mRNA in a neuronal cell.

* * * * *

SEQUENCE LISTING

```
<160> NUMBER OF SEQ ID NOS: 5

<210> SEQ ID NO 1
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Backbone-modified-U
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (2)..(2)
<223> OTHER INFORMATION: 2'-deoxy-2'-fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2'-deoxy-2'-fluoro nucleotide
```

```
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2'-deoxy-2'-fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2'-deoxy-2'-fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2'-deoxy-2'-fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: modified_base
<222> LOCATION: (14)..(14)
<223> OTHER INFORMATION: 2'-deoxy-2'-fluoro nucleotide
<220> FEATURE:
<221> NAME/KEY: misc_feature
<222> LOCATION: (14)..(20)
<223> OTHER INFORMATION: Phosphorothioate linkage
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2'-deoxy-2'-fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2'-deoxy-2'-fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2'-deoxy-2'-fluoro nucleotide
<220> FEATURE:
<223> OTHER INFORMATION: See specification as filed for detailed
      description of substitutions and preferred embodiments

<400> SEQUENCE: 1
uuaaucucuu uacugauaua                                              20
```

```
<210> SEQ ID NO 2
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxy-2'-fluoro nucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2'-deoxy-2'-fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2'-deoxy-2'-fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2'-deoxy-2'-fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2'-deoxy-2'-fluoro nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2'-deoxy-2'-fluoro nucleotide
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2'-deoxy-2'-fluoro nucleotide
<220> FEATURE:
<221> NAME/KEY: misc_feature
<222> LOCATION: (13)..(15)
<223> OTHER INFORMATION: Phosphorothioate linkage
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2'-deoxy-2'-fluoro nucleotide

<400> SEQUENCE: 2
caguaaagag auuaa                                                    15
```

```
<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Backbone-modified-U
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (2)..(2)
<223> OTHER INFORMATION: 2'-deoxy-2'-fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2'-deoxy-2'-fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2'-deoxy-2'-fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2'-deoxy-2'-fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2'-deoxy-2'-fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2'-deoxy-2'-fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: modified_base
<222> LOCATION: (14)..(14)
<223> OTHER INFORMATION: 2'-deoxy-2'-fluoro nucleotide
<220> FEATURE:
<221> NAME/KEY: misc_feature
<222> LOCATION: (14)..(20)
<223> OTHER INFORMATION: Phosphorothioate linkage
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2'-deoxy-2'-fluoro nucleotide
```

```
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2'-deoxy-2'-fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2'-deoxy-2'-fluoro nucleotide
<220> FEATURE:
<223> OTHER INFORMATION: See specification as filed for detailed
      description of substitutions and preferred embodiments

<400> SEQUENCE: 3
uuaaucucuu uacugauaua                                              20

<210> SEQ ID NO 4
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxy-2'-fluoro nucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (3)..(3)
<223> OTHER INFORMATION: 2'-deoxy-2'-fluoro nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (5)..(5)
<223> OTHER INFORMATION: 2'-deoxy-2'-fluoro nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (7)..(7)
<223> OTHER INFORMATION: 2'-deoxy-2'-fluoro nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2'-deoxy-2'-fluoro nucleotide
<220> FEATURE:
<221> NAME/KEY: modified_base
<222> LOCATION: (10)..(10)
<223> OTHER INFORMATION: 2'-O-methyl nucleotide
```

```
<220> FEATURE:
<221> NAME/KEY: modified_base
<222> LOCATION: (11)..(11)
<223> OTHER INFORMATION: 2'-deoxy-2'-fluoro nucleotide
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2'-deoxy-2'-fluoro nucleotide
<220> FEATURE:
<221> NAME/KEY: misc_feature
<222> LOCATION: (13)..(20)
<223> OTHER INFORMATION: Phosphorothioate linkage
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2'-deoxy-2'-fluoro nucleotide
<220> FEATURE:
<221> NAME/KEY: modified_base
<222> LOCATION: (16)..(16)
<223> OTHER INFORMATION: 2'-O-methyl nucleotide; a, c, g or u
<220> FEATURE:
<221> NAME/KEY: modified_base
<222> LOCATION: (17)..(17)
<223> OTHER INFORMATION: 2'-deoxy-2'-fluoro nucleotide; a, c, g or u
<220> FEATURE:
<221> NAME/KEY: modified_base
<222> LOCATION: (18)..(18)
<223> OTHER INFORMATION: 2'-O-methyl nucleotide; a, c, g or u
<220> FEATURE:
<221> NAME/KEY: modified_base
<222> LOCATION: (19)..(19)
<223> OTHER INFORMATION: 2'-deoxy-2'-fluoro nucleotide; a, c, g or u
<220> FEATURE:
<221> NAME/KEY: modified_base
<222> LOCATION: (20)..(20)
<223> OTHER INFORMATION: 2'-O-methyl nucleotide; a, c, g or u

<400> SEQUENCE: 4
caguaaagag auuaannnnn                                              20

<210> SEQ ID NO 5
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5'-E-VP-mU
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (2)..(2)
<223> OTHER INFORMATION: 2'-deoxy-2'-fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2'-deoxy-2'-fluoro nucleotide
```

```
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2'-deoxy-2'-fluoro nucleotide
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2'-deoxy-2'-fluoro nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2'-deoxy-2'-fluoro nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2'-deoxy-2'-fluoro nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: modified_base
<222> LOCATION: (14)..(14)
<223> OTHER INFORMATION: 2'-deoxy-2'-fluoro nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2'-deoxy-2'-fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2'-deoxy-2'-fluoro nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2'-deoxy-2'-fluoro nucleotide

<400> SEQUENCE: 5
uuaaucucuu uacugauaua                                            20
```